US008444985B2

(12) United States Patent  
Ibrahim et al.

(10) Patent No.: US 8,444,985 B2  
(45) Date of Patent: May 21, 2013

(54) VACCINE COMPOSITIONS AND METHODS FOR TREATMENT OF MUCORMYCOSIS AND OTHER FUNGAL DISEASES

(75) Inventors: Ashraf S. Ibrahim, Irvine, CA (US); Brad J. Spellberg, Rancho Palos Verdes, CA (US); Yue Fu, Torrance, CA (US); John E. Edwards, Palos Verdes Estates, CA (US)

(73) Assignee: Los Angeles Biomedical Research Institute at Harbor-ULCA Medical Center, Torrance, CA (US)

( * ) Notice: Subject to any disclaimer, the term of this patent is extended or adjusted under 35 U.S.C. 154(b) by 0 days.

(21) Appl. No.: 12/661,609

(22) Filed: Mar. 19, 2010

(65) Prior Publication Data

US 2010/0285024 A1 Nov. 11, 2010

Related U.S. Application Data

(60) Provisional application No. 61/161,614, filed on Mar. 19, 2009.

(51) Int. Cl.
```
A61K 39/395      (2006.01)
A61K 39/00       (2006.01)
C07K 16/00       (2006.01)
```

(52) U.S. Cl.
USPC ............. 424/146.1; 424/139.1; 530/388.26; 530/387.9

(58) Field of Classification Search
None
See application file for complete search history.

(56) References Cited

U.S. PATENT DOCUMENTS

| 6,465,504 | B1 | 10/2002 | Lattmann et al. |
| 6,595,750 | B2 | 7/2003 | Parneix et al. |
| 2009/0172834 | A1* | 7/2009 | Schauwecker et al. ....... 800/278 |

FOREIGN PATENT DOCUMENTS

| EP | 0914118 | 10/2002 |
| RU | 2118899 | 9/1998 |
| WO | WO 2004/035026 | 4/2004 |
| WO | WO 2004/045609 | 6/2004 |
| WO | WO 2004/060903 | 7/2004 |

OTHER PUBLICATIONS

Fu et al. FEMS Microbiol. Lett. 235: 169-176, 2004.*
Campbell AM In: Monoclonal Antibody Technology. Elsevier Science Publishers, The Netherlands, Chapter 1, pp. 1-32, 1984.*
Kuriyama et al. Cell Motility and the Cytoskeleton 30: 171-182, 1995.*
New Riverside University Dictionary. The Riverside Publishing Company, p. 933, 1984.*
Illustrated Stedman's Medical Dictionary. 24th Edition, Williams & Wilkins, Baltimore, p. 707, 1982.*
Abe et al., "Effects of iron and desferrioxamine on Rhizopus infection," *Mycopathologia* 110(2):87-91 (1990).
Artis et al., "A mechanism of susceptibility to mucormycosis in diabetic ketoacidosis: transferrin and iron availability," *Diabetes* 31(12):1109-1114 (1982).
Bearer et al., "Cutaneous zygomycosis caused by Saksenaea vasiformis in a diabetic patient," *J. Clin. Microbiol.* 32(7):1823-1824 (1994).
Boelaert et al., "Deferoxamine augments growth and pathogenicity of Rhizopus, while hydroxypyridinone chelators have no. effect," *Kidney Int.* 45(3):667-671 (1994).
Boelaert et al., "Mucormycosis during deferoxamine therapy is a siderophore-mediated infection. In vitro and in vivo animal studies," *J. Clin. Invest.* 91(5):1979-1986 (1993).
Brul et al., "The antifungal action of 1,10-ophenanthroline and EDTA is mediated through zinc chelation and involves cell wall construction," Food Technology and Biotechnology, 35(4): 267-274 (1997).
Cagatay et al., "Rhinocerebral mucormycosis treated with 32 gram liposomal amphotericin B and incomplete surgery: a case report," *BMC Infect. Dis.* 1:22 (2001).
Cappellini et al.,"A phase 3 study of deferasirox (ICL670), a once-daily oral iron chelator, in patients with beta-thalassemia," *Blood* 107(9):3455-3462 (2006).
Cappellini, M.D., "Iron-chelating therapy with the new oral agent ICL670 (Exjade)," Best Practice and Research Clinical Haematology, 18(2): 289-298 (2005).
Cohen-Abbo et al., "Cunninghamella infections: review and report of two cases of Cunninghamella pneumonia in immunocompromised children," *Clin. Infect. Dis.* 17(2):173-177 (1993).
Dannaoui et al., "In vitro susceptibilities of zygomycetes to conventional and new antifungals," Journal of Antimicrobial Chemotherapy, 51:45-52 (2003).
de Locht et al., "Iron uptake from ferrioxamine and from ferrirhizoferrin by germinating spores of Rhizopus microsporus," *Biochem. Pharmacol.* 47(10):1843-1850 (1994).
Donnelly et al., "Deferasirox as adjunctive therapy for mucormycosis," Journal of Antimicrobial Chemotherapy, 67:519-520 (2012).
Edwards, J., Jr., Zygomycosis, p. 1192-1199. In P. Hoeprich and M. Jordan (ed.), *Infectious Disease*, 4th ed. J.B. Lippincott Co., Philadelphia (1989); Ibrahim et al., (2003).
Ericsson et al., "A case of chronic progressive rhinocerebral mucormycosis treated with liposomal amphotericin B and surgery," *Clin. Infect. Dis.* 16(4):585-586 (1993).

(Continued)

*Primary Examiner* — S. Devi
(74) *Attorney, Agent, or Firm* — Jones Day

(57) ABSTRACT

The present invention provides therapeutic compositions and methods for treating and preventing fungal disease or conditions including mucormycosis. The therapeutic methods and compositions of the invention include vaccine compositions having an FTR polypeptide or an antigenic fragment of the polypeptide; a vector including a nucleotide sequence that is substantially complimentary to at least 18 contiguous nucleotides of FTR sequence; an antisense; a small interfering RNA or an antibody inhibitor of FTR. The vaccine compositions of the invention can further include an adjuvant.

3 Claims, 30 Drawing Sheets

(6 of 30 Drawing Sheet(s) Filed in Color)

OTHER PUBLICATIONS

Espinel-Ingroff, "In vitro fungicidal activities of voriconazole, itraconazole, and amphotericin B against opportunistic moniliaceous and dematiaceous fungi," *J. Clin. Microbiol.* 39(3):954-958 (2001).

Eucker et al., "Mucormycoses," Mycoses 44(7-8):253-260 (2001). (Abstract only).

Fu et al., "Cloning and functional characterization of the Rhizopus oryzae high affinity iron permease (rFTR1) gene," *FEMS Microbiol. Lett.* 235(1):169-176 (2004).

Galanello et al., "Safety, tolerability, and pharmacokinetics of ICL670, a new orally active iron-chelating agent in patients with transfusion-dependent iron overload due to beta-thalassemia," *J. Clin. Pharmacol.* 43(6):565-572 (2003).

Gleissner et al., "Improved outcome of zygomycosis in patients with hematological diseases?" *Leuk. Lymphoma* 45(7):1351-1360 (2004).

Howard, "Acquisition, transport, and storage of iron by pathogenic fungi," *Clin. Microbiol. Rev.* 12(3):394-404 (1999).

Howard, "Iron gathering by zoopathogenic fungi," *FEMS Immunol. Med. Microbiol.* 40(2):95-100 (2004).

Husain et al., "Opportunistic mycelial fungal infections in organ transplant recipients: emerging importance of non-Aspergillus mycelial fungi," *Clin. Infect. Dis.* 37(2):221-229 (2003).

Ibrahim et al., Zygomycosis, p. 241-251, in W.E. Dismukes, P.G. Pappas, and J.D. Sobel (ed.) *Clinical Mycology*, Oxford University Press, New York (2003).

Kamalam and Thambiah, "Cutaneous infection by Syncephalastrum," *Sabouraudia* 18(1):19-20 (1980).

Kattamis et al., "Iron chelation treatment with combined therapy with deferiprone and deferioxamine: a 12-month trial," Blood Cells Mol. Dis. 36(1):21-25 (2006).

Kemna et al., "Cokeromyces recurvatus, a mucoraceous zygomycete rarely isolated in clinical laboratories," *J. Clin. Microbiol.* 32(3):843-845 (1994).

Klimko N. N. And Kolbin A.S., "Perspectives of the Recent Systemic Antimycotics in Paediatry (Review)," Medical Problems mikologii 7(3):C3-11 (2005). (Includes English translation of Abstract).

Kontoyianis et al., "Infections due to *Cunninghamella bertholletiae* in patients with cancer: report of three cases and review," *Clin. Infect. Dis.* 18(6):925-928 (1994).

Kontoyiannis et al., "Zygomycosis in the 1990s in a Tertiary-Care Cancer Center," *Clin. Infect. Dis.* 30(6):851-856 (2000).

Kwon-Chung et al., "Pulmonary mucormycosis caused by Cunninghamella elegans in a patient with chronic myelogenous leukemia," *Am. J. Clin. Pathol.* 64(4):544-548 (1975).

Kwon-Chung, K.J., and J.E. Bennett, *Mucormycosis*, p. 524-559, *Medical Mycology*, Lea & Febiger, Philadelphia (1992).

Lye et al., "Subcutaneous zygomycosis due to Saksenaea vasiformis: rapid isolate identification using a modified sporulation technique," *Pathology* 28(4):364-365 (1996).

Maertens et al., "Mucormycosis in allogeneic bone marrow transplant recipients: report of five cases and review of the role of iron overload in the pathogenesis," *Bone Marrow Transplant* 24(3):307-312 (1999).

Marr et al., "Epidemiology and outcome of mould infections in hematopoietic stem cell transplant recipients," *Clin. Infect. Dis.* 34(7):909-917 (2002).

Marty et al., "Breakthrough zygomycosis after voriconazole treatment in recipients of hematopoietic stem-cell transplants," *N. Engl. J. Med.* 350(9):950-952 (2004).

McDonnell et al., "Antiseptics and Disinfectants: Activity, Action, and Resistance," Clinical Microbiology Reviews, 12(1): 147-179 (1999).

Nick et al., "ICL670A: preclinical profile," *Adv. Exp. Med. Biol.* 509:185-203 (2002).

Nisbet-Brown et al., "Effectiveness and safety of ICL670 in iron-loaded patients with thalassaemia: a randomised, double-blind, placebo-controlled, dose-escalation trial," *Lancet* 361(9369):1597-1602 (2003).

One page from URL: http://dic.academic.ru/dic.nsf/medic/545 (Includes Google Translation of Aspergillosis).

Reed et al., "Deferasirox, an Iron-chelating Agent, as Salvage Therapy for Rhinocerebral Mucormycosis," Antimicrobial Agents and Chemotherapy, 50(11):3968-3969 (2006).

Rees et al., "The epidemiological features of invasive mycotic infections in the San Francisco Bay area, 1992-1993: results of population-based laboratory active surveillance," *Clin. Infect. Dis.* 27(5):1138-1147 (1998).

Ribes et al, "Zygomycetes in human disease," *Clin. Microbiol. Rev.* 13(2):236-301 (2000).

Soman et al., "Deferasirox in mucormycosis; hopefully not defeated," Journal of Antimicrobial Chemotherapy, 67: 783-784 (2012).

Spellberg et al., "The Deferasirox-AmBisome Therapy for Mucormycosis (DEFEAT MUCOR) study: a randomized double-blinded, placebo-controlled trial," Journal of Antimicrobial Chemotherapy, 67:715-722 (2012).

Spellberg et al., "Safety and Outcomes of Open-Label Deferasirox Iron Chelation Therapy for Mucrormycosis," Antimicrobial Agents and Chemotherapy, 53(7):3122-3125 (2009).

Spellberg et al., "Novel perspectives on mucormycosis: pathophysiology, presentation, and management," *Clin. Microbiol. Rev.* 18(3):556-569 (2005).

Spellberg et al., "Combination Therapy with Amphotericin B Lipid Complex and Caspofugin Acetate of Disseminated Zygomycosis in Diabetic Ketacidotic Mice," Antimicrobial Agents and Chemotherapy, 49(2): 830-832 (2005).

Spellberg et al., "Parenchymal organ, and not splenic, immunity correlates with host survival during disseminated candidiasis," *Infect. Immun.* 71(10):5756-5764 (2003).

Sugar, A.M., Agent of Mucormycosis and Related Species, p. 2311-2321. In G. Mandell, J. Bennett, and R. Dolin (ed.), *Principles and Practices of Infectious Diseases*, 4t[th] ed. Churchill Livingstone, New York (1995).

Van Cutsem and Boelaert, "Effects of deferoxamine, feroxamine and iron on experimental mucormycosis (zygomycosis)," *Kidney Int.* 36(6):1061-1068 (1989).

Ventura et al., "Pneumonia with Cunninghamella species in patients with hematologic malignancies. A case report and review of the literature," *Cancer* 58(7):1534-1536 (1986).

Walsh et al., "Safety, tolerance, and pharmacokinetics of high-dose liposomal amphotericin B (AmBisome) in patients infected with Aspergillus species and other filamentous fungi: maximum tolerated dose study," *Antimicrob. Agents Chemother.* 45(12):3487-3496 (2001).

Weinberg, Eugene D., "The Role of Iron in Protozoan and Fungal Infectious Diseases," The Journal of Eukaryotic Microbiology, 46(3): 231-238 (1999).

Weiss et al., "In vitro blood distribution and plasma protein binding of the iron chelator deferasirox (ICL670) and its iron complex Fe-[ICL670]2 for rat, marmoset, rabbit, mouse, dog, and human," Drug Metab. Dispos. 34(6):971-975 (2006).

\* cited by examiner

```
LOCUS       AY344587    1107 bp DNA linear    PLN 25-JUN-2004
DEFINITION  Rhizopus oryzae high-affinity iron permease gene, complete
cds.
ACCESSION   AY344587
VERSION     AY344587.1   GI:33637943

SEQ ID NO:1

1 atgtctcaag atctcttcaa cgtaccgatc ttctttatcc ttttcgtga aacgactgag
  61 gcagccatca ttatttctgt cctcttgtca ttcttgaaga gaatgtttaa tacagaatct
 121 cctgtttata aacgtctcag aaatcaagtc tggattggtg gtgcagctgg tctgttttatc
 181 tgtttatgta tcggtgctgc cttcattgcc gttactaca ctgtccttaa tgacttgtgg
 241 ggaaattctg aagatatctg ggaaggtgtc ttctctctgg ttgctgtgat catgatcact
 301 gccatgggtc ttgctatgct caagactgaa cgtatgcaag aaaagtggaa ggtcaagttg
 361 gctaaagcaa tgcaaaagtc aacagtgaa aagtcatcct taaagaaaa acttcaaaaa
 421 tacgcgttct ttgtcttgcc ttttatcacc gttctcagag aaggacttga agctgttgtc
 481 tttattggtg gtgtctcctt gggtatccaa ggaaaatcaa ttcctattgc tgccatcatg
 541 ggtatcatct gtggttgttt ggtcggtttc cttatttacc gtggtggttc cttgattcaa
 601 cttcgttggt tctttgtgtt ctctactgtc gttctttacc ttgtcgctgc tggtttgatg
 661 gctaaaggtg ttggttacct tgaacaaaat gcttggaatc aagtcattgg tggtgaagct
 721 gctgatgtca ttagttacag agtctcaacc gctgtctggc acgtttcttg gggagaccca
 781 gaagccaaca atgatacctc tggtggttgg caaatcttta cgccattct tggttggaac
 841 aatacggcta cttatggttc tatcatcagt tactgtctct actggctctt tgtctgctgt
 901 tatcttgtct ttagttactt taaggaaaag cgtgctgcta tccgtaaagc cgaggctggt
 961 gaatgggatg atggtgatga agctttggag aatgccaaac aatacattgg taatgatggt
1021 gaattcatcg ttgaagacaa agaatctgat gaagaagcca acaatcatcc caaggaaaaa
1081 atcgaatctg atgctattaa ggcttaa
```

Figure 1

```
LOCUS       AY344587    1107 bp DNA linear    PLN 25-JUN-2004
DEFINITION  Rhizopus oryzae high-affinity iron permease gene, complete
cds.
ACCESSION   AY344587
VERSION     AY344587.1   GI:33637943
protein_id="AAQ24109.1"

SEQ ID NO:2

1 MSQDLFNVPI FFILFRETTE AAIIISVLLS FLKRMFNTES PVYKRLRNQV WIGGAAGLFI
  61 CLCIGAAFIA VYYTVLNDLW GNSEDIWEGV FSLVAVIMIT AMGLAMLKTE RMQEKWKVKL
 121 AKAMQKSNSE KSSFKEKLQK YAFFVLPFIT VLREGLEAVV FIGGVSLGIQ GKSIPIAAIM
 181 GIICGCLVGF LIYRGGSLIQ LRWFFVFSTV VLYLVAAGLM AKGVGYLEQN AWNQVIGGEA
 241 ADVISYRVST AVWHVSWGDP EANNDTSGGW QIFNAILGWN NTATYGSIIS YCLYWLFVCC
 301 YLVFSYFKEK RAAIRKAEAG EWDDGDEALE NAKQYIGNDG EFIVEDKESD EEANNHPKEK
 361 IESDAIKA
```

Figure 2

**Sequence of high affinity iron permeas from *Aspergillus fumigatus***

```
   1 ATGATCGGAG CGTTCTATGG ATATGGTAAG GATCACTTCG CTAGCACGGA GGACCTGTGG
  61 GAGGGCATCT TCTCCCTGAT CGCCAGTGTC ATCATCACCA TTATGGGTGC TGCCCTGCTT
 121 CGTGTCACCA AGTTGCAGGA GAAGTGGCGC GTCAAGCTAG CTCAAGCCCT GGAAGCAAAG
 181 CCGTTGACTG GCGGCACATT CAAAAACAAC CTCAAACTTT GGGCGGAGAA ATACGCCATG
 241 TTTCTCCTCC CCTTCATCAC CGTTCTCCGA GAAGGCCTGG AAGCAGTGGT GTTCATTGGA
 301 GGCGTCAGTC TCAGTTTTCC TGCAACTGCC TTCCCTCTAC CTGTTTTTAC TGGCATTCTC
 361 GCAGGAGTGG CCATTGGGTA CCTACTGTAT CGGTATGTTG AAACCCCTGA ATCAGCTGTC
 421 TTTCTCAAAT AGACCACCAT GCTGATGGTC TGCAGAGGAG GAAACCAAGC CTCCCTCCAG
 481 ATCTTCCTGA TCATCTCCAC TTGCATCCTC TACCTGGTTG CTGCCGGCCT CTTCTCCCGA
 541 GGCGTCTGGT ATCTGGAGAA CAATACTTGG AACCACGTAA TTGGTGGTGA TGCTGCCGAG
 601 ACAGGTGCCG GTCCGGGATC GTATGACATC CGACAGAGCG TCTGGCATGT CAACTGCTGT
 661 AGTCCTCTCG TTAATGGTGG CGGGGGATGG GGTATCTTCA ACGCCATCCT TGGCTGGACA
 721 AACTCGGCAA CCTATGGCTC CGTTCTTTCA TACAACCTTT ACTGGATTGC GGTGATCGTC
 781 TGGTTTGTGG CTATGCGTCA CAAGGAACGC CATGGACGAT TGCCTGTGGT CGACCCTCTG
 841 CTGAATCGGC TGCGAGGCCG AAAGTCTGCC GAACCTGGGA ATGGAGAGCA AGATGTCGAG
 901 GTCAGCACGA TACCATCTGA TTTGCAGACG GAGTCCAAAA TACCGAAAAG CGGAGCATCC
 961 CTTGTCTGA
```

Figure 15

**Sequence of high affinity iron permeas from *Candida guilliermondii***

```
   1 ATGAACTTTG AAGACTACTT CTCGGTTCAA ATCTTCTTTA TAATCCTCCG AGAAACGTTG
  61 GAGACCGCTA TAGTGATTTC GGTTCTTCTT TCGTTCATCA ATCAAAGAAG CCAAGAAGCA
 121 AATGACCGAG GAAATTCTGC TAATGAAGCT GCTCATACTC GAGGATTGCG GGTCCAGGTA
 181 TGGGCCGGGG CCTTAATGGG ATTTGTTGTG TGTTTTGCCA TCGGAGTGGC ATTTGTGGTT
 241 GCATTTTATG TCATTGGAGA GAACTACTGG CTGTATGCTG AAAGACTCTG GGAGGGTATT
 301 TTCTCGCTTC TTTCGAGTAT AATAATCACA GTGATGGGTA TCGGATTGCT ACGTATAAAC
 361 CGCGTGATGA AAGTTAAGTG GTTTGCTAAG TTGGGTGATG CCTTTGATCT GCATTCGCAC
 421 GGTAGAGGCC ATAAAAAGAA GTACTTTCTT GCATTATTAC CATTTATAAC CACACTCAGA
 481 GAAGGCTTGG AGGCCGTGGT ATTCGTGGGT GGAATTGGTC TTTCGCTGCC AGTTTCTTCC
 541 ATCCCATTTT CCATTCTCAG TGGAATCTGT GTGGGATCCA CAATCGGTTA CACTTTGTAC
 601 AAAGGAGGCA ACAAGCTTTC TCTCCAATAC TTCCTCATCT TGCTGACCTG CTTTTTGTAC
 661 ATAGTTCTGG CAGGGCTTAT GAGTAGAGGA GTATGGTTTT TGGAACTCGA GCTGTATGTG
 721 AGAAAATGTG GAGGACTCGA CGTTAGCGAA ACAGGTAGTG GACCTGGATC TTATGATCCT
 781 GCTACAAGCG TGTGGCATGT CAATTGCTGT AACGGACTCA CAGATGGCTG GTGGATGGTT
 841 TTAAATGCTC TTGTTGGCTG GACCAATTCC GCAACTTATG GCAGCGTAGG TGCTTATTGT
 901 GCCTATTGGA TATTGGTCAT TTCATGGCTT GAGATCCGCT TGTACGAAGA GCATCATGGA
 961 CTCTTACCCT TTGTTCCTGT GCGTTGGCAG TTGAAGCGTA TCAGAAAAAA AATCAAATTA
1021 TACGAAGCCC GGGCCAAACA TGGCGCTGCA ATACAGGCTG AAACAGAGGC AGAATTACTC
1081 ATGGAATAA
```

Figure 16

Sequence of high affinity iron permeas from *Aspergillus flavus*

Gene 1

```
  1 AGCCCTCTTT CATTCCTTTC TGAAGCCTCT ACCTTCCACT CAACATGGCA ACCGATGTAT
 61 TTGCAGTTCC CAGTATGCAT TCTTTTCTTG TTATGCCCCA TCTATTAATC AGGAACTAAC
121 TTAGTTTGAC TAACTTATCG AAGTATTCTT CATCTGCTTT CGAGAATGCG TTGAGACCAG
181 CATCATTGTT TCGGTATTAC TTGCCTTCAT CAAGCAGACG CTGGGGTCGG ACACGGATGC
241 CTTTACTCGC AAAAGGCTTA TCAAACAGGT TACTACCATC TTCTCATTCC GTCCCCACCC
301 TATAGAGACA ACATTGACGA TCAATAGGTC TGGTGGGGAG TTGCGGTCGG GCTGTTTATA
361 TGCCTCTGTA TTGGAGGTGG TATGATTGGG GCCTTCTACG GGTATGGCAA GGACCATTTT
421 GCCAGCACGG AGGATTTATG GGAAGGCATC TTTGCTTTAG TCGCCGCCGT CATCATCACA
481 GTCATGGGAG CAGCCCTTCT GCGGGTGAAT AAACTGCAGG AGAAATGGCG TGTCAAGCTG
541 GCCCAGGCAT TGGCGGCAAA ACCTCAACCT CAAGGGAGAA TGACAGACAA GATCAAGCAA
601 TGGTCACAGA AGTATTTCAT GTTCATCTTA CCCTTCATTA CGGTACTTCG GGAGGGTCTA
661 GAGGCTGTGG TGTTTATCGG GGGTGTTAGT CTCAGCTTCC CCGCAAGCGC GTTCCCTCTC
721 CCTGTATTCA CGGGACTCTT GGCTGGTGTG GTAGTTGGTT ATATCATTTA CCGGTGAGTG
781 TGATATGGGC GGCATTGAAA CTGAATCCCA ATGCTGATAG TAGTCTTTGC GATTTATCAT
841 AGGGGCGGGA ATCAAACCTC ACTTCAGATA TTCATGGTCA TCTCGACATG TCTGCTCTAC
901 TTGGTCGCTG CTGGACTTTT GTCCCGAGGC GTCTGGTTCT TGGAGAACAA CACTTGGAGC
961 AACCTCATCG GTGGCGATGC CTCAGAAACG GGAGCT
```

Gene 2

```
   1 ATGGCAAATC AAGTCTTTGC AGTCACTGGT AACTCTCATT ATACTCTCTG AGTCTGCTTT
  61 TGTACAAGAC GACCGTTGCT GACCGTGTAT AGTCTTTTTC ATTTGCTTCC GAGAATGTCT
 121 CGAAAGCAGT ATCATTGTAT CGGTGCTTCT TGCCTTCCTC ACCCAAACTT TGGGTGCTGA
 181 AGGAGACAAG GCAGCTCTGA AGAGATTGCG AATACAGGTG AGTGTCCTTC CCTATTTCTT
 241 TATACCTTTG TTTATCATGA ACATCATTCG ATAATGAGCT GCTAACAATA ACAGGTATGG
 301 TGTGGAGTAG GTTTAGGTCT ATTCTTGTGC CTATGTATCG GTGCAGGTAT GATCGGAGCT
 361 TTCTACGGGT TGGAAAAAGA TACCTTCACG AACACAGAGG ATATCTGGGA AGGCATTTTT
 421 GGCTTTATAG CATCCATCAT TATTTCTATC ATGGGGGCGG GCCTTTTGCG TGTGAACAAA
 481 ATGCGCGAGA AATGGCGCGT CAAGCTCTCC CGTGCCTTGG AGAAAAAGGA AAAGTCTACG
 541 ACCATAATGG GTCGTCTGAA GGACTGGTCC GAGAAATATG TCATGTTCAT CTTGCCATTC
 601 GTTACCGTTC TTCGAGAGGG ACTTGAGGCT ATCGTTTATG TCGGTGGTGT GGGACTGGGA
 661 TTGCCAGCGT CTTCATTCCC CTTGGCCGTG TTCTGTGGCC TTTTGGCTGG TGTTGCAGTA
 721 GGCTATGTGA TGTATCGGTA AGTCTTGTGC GTTACATTCT GTCTACTTTA AGAATCATTA
 781 TCTGCACAGT ATCGTTCGAC GGTGGCTAAC GAATCTTGAT GCAGGGGTGG AAGCTCAACT
 841 TCCTTACAGT ACTTTCTGAT TATATCTACT TGCTTCCTCT ACTTGGTCGC CGCAGGCTTG
 901 TTTTCCCGCG CTGTCTGGTA CCTGGAGAAT AATACCTGGA ACCATGTCAT TGGTGAGAT
 961 GCTTCTGAGA CCGGCTCAGG CCCTGGATCT TACGATATTC GCCAGAGTGT CTGGCATGTA
1021 AACTGCTGTA ACCCAGAGCT TGGCGGTGGT GGTGGTTGGG GTATCTTCAA CGCTCTGTTT
1081 GGGTGGACCA ATTCCGCCAC CTATGGATCA GTGCTATCTT ACAACCTTTA CTGGGTAGTG
1141 ATCATTACCT CATACGTCTG CATGAGGTAC AATGAGAAGC ACGGCTACAT TCCCGTCTTA
1201 ACACCGATCG CAAGGAAGCT GAAGCTTGGT CGATTCAAGA AGGGCTCTGA GGAAGAACAT
1261 GTCCCCGAGG TTGTCGAAGA GAGGAAGGAG GTTAACCATC TGGCCCGGCA AATTGTTACC
1321 AGAACAATGA GTGAAGCATA G
```

Figure 17

Sequence of high affinity iron permeas from *Candida tropicalis*

```
   1 ATGGCACAGA TCGAGGAGTA CTTTTCTGTT CAGATATTCT TTATCATTCT CAGAGAGACT
  61 CTTGAAACAG CTATCATCAT CTCGGTGTTG CTATCCTTCA TCAACCAACG TTCGCACAAG
 121 CATGGCTCCC AGTCTCAGAA CATAGCAGTA TCATCGTCAT CACCATCGAC ATCATCACCT
 181 GGTTCAGTGG ACCCGCCGA TGAGCCACTA CCTTCGAGTT CAACCACTGT CACCCCGGGA
 241 CAGACATCCC ATTTGGAGAA AGTGCATCGT AAGCTTAAAC TTCAAGTATG GGTGGGCGCC
 301 CTTCTTGGGC TTTTCATTTG TTTTGTCATC GGGATGGTAT TTACGTTGAT GTTTTATTTT
 361 GTGGGACAGG ACTACTGGGC ATACACGGAA CGAGTATGGG AAGGTGTGTT CTGCATATTG
 421 TCAAGTGTGA TCATCACTGT GATGGGGATT GGGCTTTTGA GAATCAACAA AGTTATGAAG
 481 ATCAAATGGT GGATCAAGTT GGGAGATGCG TACAATAATG AAGAATACGC AGAAGACGAA
 541 GAGGCAGAAG GCGAGGAAGA GATTGCCAAG TTAGGAGACG ACGATGTGAT GTATGAGGAT
 601 AGTATGGCTA ATTATGGAGG CACCAGGTCG AGCTCAGAGT CAAACACCGT GGAGGAGAAC
 661 ATCCCATTAA CCGGTACGCC TGCTACTCCT GCAACAGCTA GAACCACAAC CACAAAGAAG
 721 AACACACCAA GGAAACAGGG GTTCACCAAG AAATACTACC TTGCTATTTT ACCATTGGTC
 781 ACCACATTGA GAGAAGGGTT AGAAGCGGTT GTGTTCATTG GTGGCTCAGC CATGACGTCC
 841 ACGGTATTTT CGATCATTGT GTCTGTTGTC TGCGGAATTG CATTTGGTTC CTTGATTGGG
 901 TACTTGCTTT ACCAAGGGGG GAACAAACTC TCCCTTCAGT ATTTTCTTAT TTGCTCAACA
 961 TGTTTTCTTT ACATGGTCAG CGCTGGGTTG ATCAGTCGTG GTGTCTGGTT TATGGAGCTT
1021 GAAAGATATG TCCGTGCATG TGGGGGCATG GACGTTAGTG AAACGGGAAG TGGGCCAGGT
1081 TCATATGATA TCGCAACCAG TGTGTGGCAT GTCAACTGTT GTAACGGACT AACTGACGGT
1141 TGGTGGATGG TGTTGAACGC AATTGTCGGC TGGACCAATT CGGCTACATA TGGCAGTGTG
1201 ATTAGTTATA TGGCATACTG GTTGTTGGTA ATTGTGTGGT TGAAAGTTAA GTTGTATGAA
1261 GAGAGGGAAG GTGTGTTGCC TTGGATTCCC GTAAGATGGC AACTCAAGAG AATTAGAAAG
1321 AAGATTAGAT TGTATGAATT GAGGACCCGT CAGCAAGAGC AACAGGAGCA ACAGAGAGGT
1381 GGTAGTGGTA GTGGTAATGA ATTGCCAGAA TCGCAAGGAT TGTTGCAACA GGATTGA
```

Figure 18

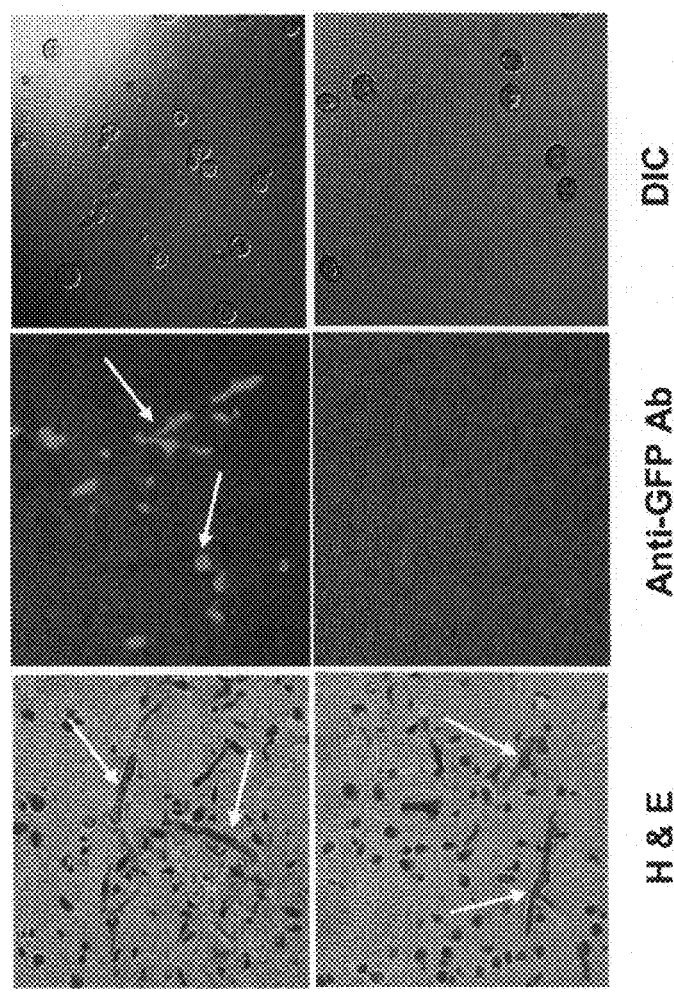

WT FTR1
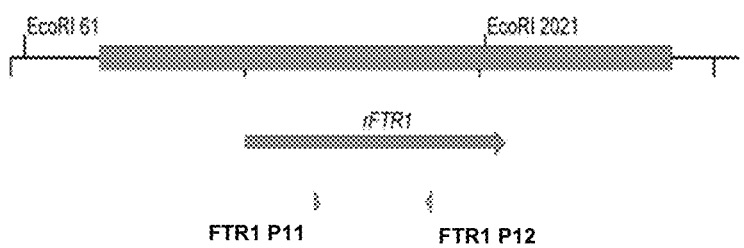
Putative ftr1 null
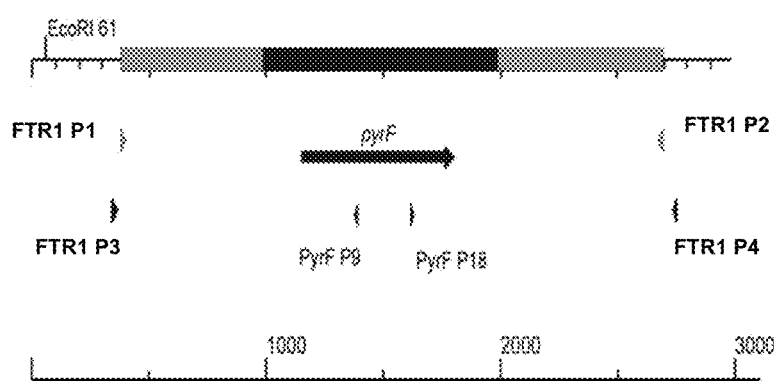
Figure 23A ized to cause disease (mycosis) in man and animal. Some of
VACCINE COMPOSITIONS AND METHODS FOR TREATMENT OF MUCORMYCOSIS AND OTHER FUNGAL DISEASES This application claims the benefit of priority of U.S. Provisional application Ser. No. 61/161,614, filed Mar. 19, 2009, the entire contents of which are incorporated herein by reference.

This invention was made in part with U.S. Government support under NIH grant 011671 awarded by NIAID. The U.S. Government can have certain rights in the invention.

BACKGROUND OF THE INVENTION

This invention generally relates to compositions and methods to vaccinate subjects against infectious diseases and, more particularly, relates to compositions and methods to vaccinate subjects against opportunistic fungal diseases.

About 180 of the 250,000 known fungal species are recognized to cause disease (mycosis) in man and animal. Some of fungi can establish an infection in all exposed subjects, e.g., the systemic pathogens *Histoplasma capsulatum* and *Coccidioides immitis*. Others, such as *Candida, Asergillus* species and Zygomycetes are opportunist pathogens which ordinarily cause disease only in a compromised host. Fungi of the class Zygomycetes, order Mucorales, can cause Mucormycosis, a potentially deadly fungal infection in human. Fungi belonging to the order Mucorales are distributed into at least six families, all of which can cause mucormycosis (Ibrahim et al. *Zygomycosis*, p. 241-251, In W. E. Dismukes, P. G. Pappas, and J. D. Sobel (ed.), *Clinical Mycology*, Oxford University Press, New York (2003); Kwon-Chung, K. J., and J. E. Bennett, *Mucormycosis*, p. 524-559, *Medical Mycology*, Lea & Febiger, Philadelphia (1992), and Ribes et al. *Zygomycetes in Human Disease, Clin Microbiol Rev* 13:236-301 (2000)). However, fungi belonging to the family Mucoraceae, and specifically the species *Rhizopus oryzae (Rhizopus arrhizus)*, are by far the most common cause of infection (Ribes et al., supra). Increasing cases of mucormycosis have been also reported due to infection with *Cunninghamella* spp. in the Cunninghamellaceae family (Cohen-Abbo et al., *Clinical Infectious Diseases* 17:173-77 (1993); Kontoyianis et al., *Clinical Infectious Diseases* 18:925-28 (1994); Kwon-Chung et al., *American Journal of Clinical Pathology* 64:544-48 (1975), and Ventura et al., *Cancer* 58:1534-36 (1986)). The remaining four families of the Mucorales order are less frequent causes of disease (Bearer et al., *Journal of Clinical Microbiology* 32:1823-24 (1994); Kamalam and Thambiah, *Sabouraudia* 18:19-20 (1980); Kemna et al., *Journal of Clinical Microbiology* 32:843-45 (1994); Lye et al., *Pathology* 28:364-65 (1996), and Ribes et al., (supra)).

The agents of mucormycosis almost uniformly affect immunocompromised hosts (Spellberg et al., *Clin. Microbiol. Rev.* 18:556-69 (2005)). The major risk factors for mucormycosis include uncontrolled diabetes mellitus in ketoacidosis known as diabetes ketoacidosis (DKA), other forms of metabolic acidosis, treatment with corticosteroids, organ or bone marrow transplantation, neutropenia, trauma and burns, malignant hematological disorders, and deferoxamine chelation-therapy in subjects receiving hemodialysis.

Recent reports have demonstrated a striking increase in the number of reported cases of mucormycosis over the last two decades (Gleissner et al., *Leuk. Lymphoma* 45(7):1351-60 (2004)). There has also been an alarming rise in the incidence of mucormycosis at major transplant centers. For example, at the Fred Hutchinson Cancer Center, Man et al. have described a greater than doubling in the number of cases from 1985-1989 to 1995-1999 (Man et al., *Clin. Infect. Dis.* 34(7):909-17 (2002)). Similarly, Kontoyiannis et al. have described a greater than doubling in the incidence of mucormycosis in transplant subjects over a similar time-span (Kontoyiannis et al, *Clin. Infect. Dis.* 30(6):851-6 (2000)). Given the increasing prevalence of diabetes, cancer, and organ transplantation in the aging United States population, the rise in incidence of mucormycosis is anticipated to continue unabated for the foreseeable future.

Available therapies for invasive mucormycosis include attempts to reverse the underlying predisposing factors, emergent, wide-spread surgical debridement of the infected area, and adjunctive antifungal therapy (Edwards, J., Jr., Zygomycosis, p. 1192-1199. In P. Hoeprich and M. Jordan (ed.), *Infectious Disease*, 4th ed. J. B. Lippincott Co., Philadelphia (1989); Ibrahim et al., (2003), supra; Kwon-Chung and Bennett, supra; Sugar, A. M., Agent of Mucormycosis and Related Species, p. 2311-2321. In G. Mandell, J. Bennett, and R. Dolin (ed.), *Principles and Practices of Infectious Diseases*, 4th ed. Churchill Livingstone, New York (1995)).

Currently, Amphotericin B (AmB) remains the only antifungal agent approved for the treatment of invasive mucormycosis (Id.). Because the fungus is relatively resistant to AmB, high doses are required, which frequently cause nephrotoxicity and other adverse effects (Sugar, supra). Also, in the absence of surgical removal of the infected focus (such as excision of the eye in subjects with rhinocerebral mucormycosis), antifungal therapy alone is rarely curative (Edwards, J. (1989), supra; Ibrahim et al., (2003), supra). Even when surgical debridement is combined with high-dose AmB, the mortality associated with mucormycosis exceeds 50% (Sugar, supra). In subjects with disseminated disease mortality approaches 100% (Husain et al., *Clin Infect Dis* 37:221-29 (2003)). Because of this unacceptably high mortality rate, and the extreme morbidity of highly disfiguring surgical therapy, it has been imperative to develop new strategies to treat and prevent invasive mucormycosis.

One of the underlying factors in predisposition to fungal infection is elevated serum iron levels. Subjects who have elevated available serum iron are hypersusceptible to mucormycosis. Iron is required by virtually all microbial pathogens for growth and virulence. In mammalian hosts, very little serum iron is available to microorganisms because it is highly bound to carrier proteins such as transferrin. Although sequestration of serum iron is a major host defense mechanism against pathogenic fungi, subjects treated with exogenous iron chelators e.g., deferoxamine have a markedly increased incidence of invasive mucormycosis, which is associated with a mortality of >80%. While deferoxamine is a chelator from the perspective of the human host, it predisposes subjects to mucormycosis by acting as a siderophore, supplying previously unavailable iron to the pathogenic fungi.

Therefore, there exists a need for compounds and methods that can reduce the risk of mucormycosis pathogenesis and provide effective therapies without adverse effects. The present invention satisfies this need and provides related advantages as well.

SUMMARY OF THE INVENTION

In accordance with the embodiments outlined in this disclosure, the present invention provides a vaccine composition, including an FTR polypeptide, or an antigenic fragment of the polypeptide, and a pharmaceutically acceptable carrier. In addition, the invention provides a vaccine composition, including a vector having a nucleotide sequence that is substantially complimentary to at least 18 contiguous nucleotides of FTR sequence, a transcription promoter, and a transcription terminator; wherein the promoter is operably linked to the FTR nucleotide sequence, and wherein the FTR nucleotide sequence is operably linked to the transcription terminator, and a pharmaceutically acceptable carrier. The vaccine compositions of the present invention can further include an adjuvant.

In addition, the invention provides a pharmaceutical composition for treating or preventing a fungal condition in a subject in need thereof, including an antisense, a small interfering RNA or an antibody inhibitor of FTR selected from the group consisting of a nucleotide sequence that is substantially complimentary to a portion of an FTR sequence; a nucleotide sequence that is substantially complimentary to at least 12 contiguous nucleotide bases of FTR sequence; a nucleotide RNAi sequence that is substantially complimentary to at least 18 contiguous nucleotide bases of FTR sequence; an antibody or antibody fragment thereof that specifically binds to an FTR polypeptide or a fragment thereof; and a pharmaceutically acceptable excipient or carrier.

In addition, the invention provides a method of treating or preventing a fungal condition, including administering to a subject having, or susceptible to having, a fungal condition an immunogenic amount of an FTR polypeptide, or an immunogenic fragment thereof In addition, the invention provides a method for treating or preventing a fungal condition in a subject in need thereof, including exposing said fungi to an antisense, a small interfering RNA or an antibody inhibitor of FTR.

BRIEF DESCRIPTION OF THE DRAWINGS

This patent or application file contains at least one color photograph. Copies of this patent or patent application publication with the color photographs will be provided by the Patent & Trademark Office upon request and payment of the necessary fee.

FIG. 1 shows *Rhizopus oryzae* high affinity iron permease nucleotide sequence (SEQ ID NO: 1), with Genbank cDNA accession NO. AY344587.

FIG. 2 shows *Rhizopus oryzae* high affinity iron permease polypeptide sequence (SEQ ID NO:2), with Genbank protein ID. No. AAQ24109.1.

FIG. 15 shows *Aspergillus fumigatus* high affinity iron permease nucleotide sequence (SEQ ID NO:40).

FIG. 16 shows *Candida guilliermondii* high affinity iron permease nucleotide sequence (SEQ ID NO:41).

FIG. 17 shows *Aspergillus flavus* high affinity iron permease nucleotide sequences (SEQ ID NOS: 42 and 43).

FIG. 18 shows *Candida tropicalis* high affinity iron permease nucleotide sequence (SEQ ID NO:44).

DETAILED DESCRIPTION OF THE INVENTION

This invention is directed to the use of compositions and methods that directly and/or indirectly inhibit the high affinity iron permease (FTR) of pathogenic fungi, specifically those involved in the onset of mucormycosis. High affinity iron permease is a molecule responsible for the uptake of iron in fungi; targeting and inhibition of this molecule, therefore, will impede the ability of the fungi to uptake and/or use the iron available in the surrounding environment. Inhibition of high affinity iron permease will result in iron-starvation in fungal pathogens hampering their growth and/or virulence. The FTR polypeptide in, for example, R. oryzae has little or no homology with any known human proteins. For example, homology search of the human proteome identified five open reading frames with extremely limited homology to R. oryzae's FTR protein with an alignment score of 30.4, e=9.0 for all of the five proteins. Three of these proteins are coiled-coil domain containing 82 (i.e., EAW66982; AAH33726.1; and NP_079001.2), one is a CCDC82 protein (i.e., AAH18663.1) and an unnamed protein (i.e., BAB15683.1) As a benchmark, the standard BLAST search e value for identification of unique sequences from fungi compared to other organisms has been set at $10^{-8}$, indicating that rFtr1p has no significant homology to the human proteome. Therefore, the compositions and methods of the current invention in targeting and inhibiting FTR will only affect the iron levels in the fungal pathogen not the host, which constitutes an effective and targeted therapy against mucormycosis.

In one embodiment, the invention is directed to an immunogenic composition such as a vaccine. The immunogenic composition includes an effective dose of fungal FTR polypeptide or an antigenic fragment thereof that confer protection against mucormycosis in a subject. The vaccine composition of the invention induces host humoral and/or cell mediated immune response against fungal FTR. In another embodiment, a composition of the invention further includes an adjuvant that can boost the immunogenecity of the vaccine composition.

In yet another embodiment, the invention includes an inhibitor of FTR molecule such as siRNA, for example. The FTR inhibitor includes a vector expressing one or more siRNAs that include sequences sufficiently complementary to a portion of the FTR molecule for inhibiting FTR transcription or translation levels. For example as described in Example 9, interfering RNAs against FTR of R. oryzae were prepared, which were shown to inhibit FTR expression in these fungi. In DKA mice, it was demonstrated that R. oryzae transformants harboring anti-FTR siRNAs were less virulent than the wild type R. oryzae.

Figure 3:
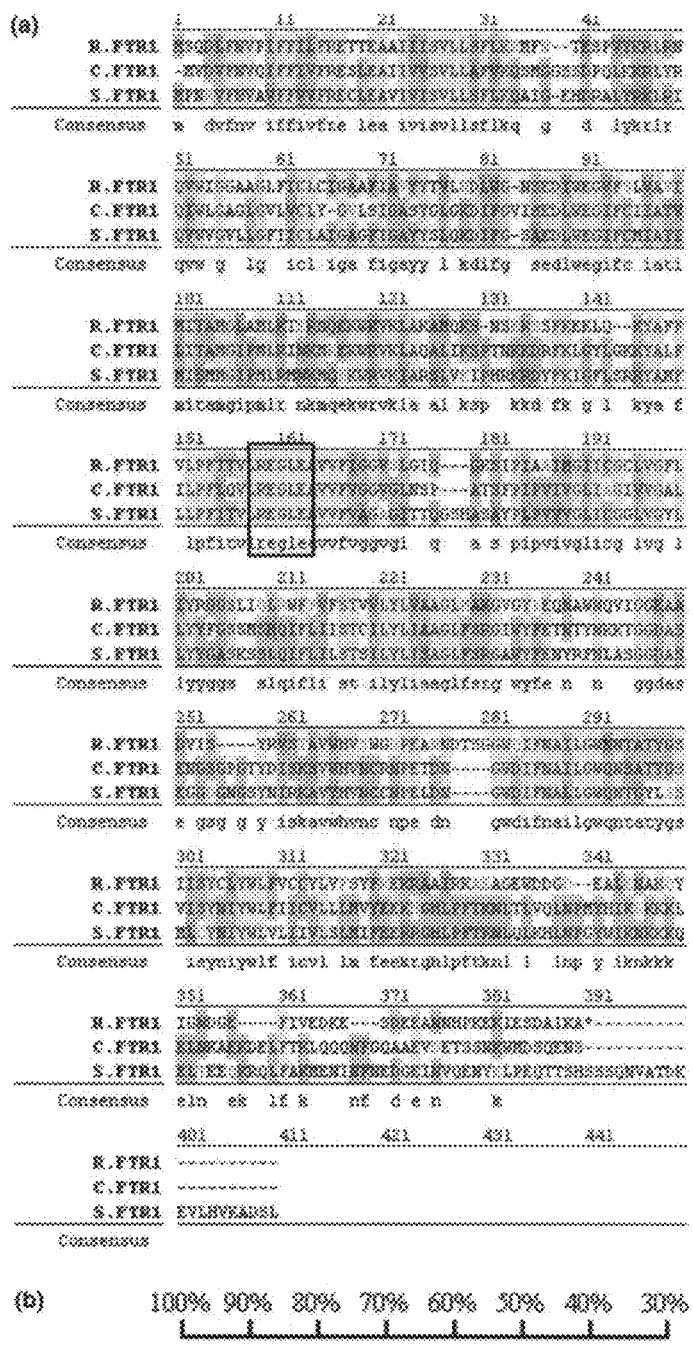
FIG. 3 shows amino acid sequence alignment (a) and dendrogram (b) for FTR of *R. oryzae* (SEQ ID NO:37) having 46% and 44% identity with FTR of *C. albicans* (SEQ ID NO:38) and *S. cerevisiae* (SEQ ID NO:39), respectively. Box on amino acid sequence alignment indicates the conserved REGLE motif (SEQ ID NO:3) involved in a direct interaction with iron.

As used herein, the term "FTR" refers to high affinity iron permease, a membrane protein responsible for iron transport in pathogenic fungi, such as, but not limited to FTR in R. oryzae, A. fumigatus, C. guilliermondii, A flavus, and C. tropicalis; and the nucleic acids encoding the same. As shown in FIG. 3 and described in Example 1, for example, FTRs from R. oryzae, C. albicans and S. cerevisiae share percent identities of 39% or more with multiple regions of protein sequence homology. The nucleotide sequence of FTR in, for example, R. oryzae is shown in FIG. 1 (SEQ ID NO:1), and the corresponding amino acid sequence is shown in FIG. 2 (SEQ ID NO:2). The nucleotide sequence of FTR, in A. fumigatus is shown in FIG. 15; in C. guilliermondii is shown in FIG. 16; in A flavus is shown in FIG. 17; and in C. tropicalis is shown in FIG. 18. Throughout the present specification, the terms "FTR expression" or "expressing FTR" can be employed to designate indifferently expression of an FTR nucleic acid or an FTR polypeptide.

Generally, nucleic acid is an RNA, for example, mRNA or pre-mRNA, or DNA, such as cDNA and genomic DNA. An FTR nucleic acid, for example, refers to a nucleic acid molecule (RNA, mRNA, cDNA, or genomic DNA, either single- or double-stranded) corresponding to FTR polypeptide or an immunogenic fragment thereof DNA molecules can be doubled-stranded or singled-stranded; single stranded RNA or DNA can be either the coding or sense strand, or the non-coding or antisense strand. The nucleic acid molecule or nucleotide sequence can include all or a portion of the coding sequence of the gene and can further include additional non-coding sequences such as introns and non-coding 3' and 5' sequences (including promoter, regulatory, poly-A stretches or enhancer sequences, for example). In addition, the nucleic acid molecule or nucleotide sequence can be fused to another sequence, for example, a label, a marker or a sequence that encodes a polypeptide that assists in isolation or purification of the polypeptide. Such sequences include, but are not limited to, those that encode a selection marker (e.g. an antibiotic resistance gene, or a reporter sequence), those that encode a repetition of histidine (HIS tag) and those that encode a glutathione-S-transferase (GST) fusion protein. The nucleic acid molecule or nucleotide sequence can include a nucleic acid molecule or nucleotide sequence which is synthesized chemically or by recombinant means, such nucleic acid molecule or nucleotide sequence is suitable for use in recombinant DNA processes and within genetically engineered protein synthesis systems.

The term "polypeptide" refers to a chain of two or more amino acids covalently linked by a peptide bond. Particular polypeptides of interest in the context of this invention are amino acid subsequences having antigenic epitopes. Antigenic epitopes are well known in the art and include sequence and/or structural determinants substantially responsible for the immunogenic properties of a polypeptide and being capable of evoking an immune response. Functional domains of the FTR polypeptide are also considered to fall within the scope of the invention. For example, the REGLE (SEQ ID NO: 3) motif which interacts with iron is one exemplary functional domain of the invention. Another exemplary functional domain is the cell surface EXXE (SEQ ID NO: 45) motif of FTR which is required for full function of FTR in Saccharomyces cerevisiae (Stearman et al., Science 271: 1552-1557 (1996)). Polypeptides also undergo maturation or post-translational modification processes that can include, for example, glycosylation, proteolytic cleavage, lipidization, signal peptide cleavage, propeptide cleavage, phosphorylation, and such like.

The term "immunogenic" or "antigenic" as it is used herein refers to a portion of a protein that is recognized by a T-cell and/or B-cell antigen receptor. The immunogenic portion generally includes at least 5 amino acid residues, preferably at least 10, more preferably at least 20, and still more preferably at least 30 amino acid residues of an FTR polypeptide or a variant thereof. Preferred immunogenic portions can contain a small N- and/or C-terminal fragment (e.g., 5-30 amino acids, preferably 10-25 amino acids).

A variant polypeptide contains at least one amino acid change compared to the target polypeptide. Polypeptide variants of FTR can exhibit at least about 39%, more preferably at least about 50%, and even more preferably at least about 70% identity to the FTR polypeptide. A polynucleotide variant includes a substantially homologous polynucleotide that deviates in some bases from the identified polynucleotide, usually caused by mutations such as substitution, insertion, deletion or transposition. Polynucleotide variants preferably exhibit at least about 60% (for fragments with 10 or more nucleotides), more preferably at least about 70%, 80% or 90%, and even more preferably at least about 95%, 98% or 99% identity to the identified polynucleotide.

The term "fragment" as used herein with reference to an FTR polypeptide is intended to refer to a polypeptide having a portion of FTR amino acid sequence. Useful fragments include those that retain one or more of the biological activities of the polypeptide. Such biologically active fragments can have a wide range of lengths including, for example, 4, 6, 10, 15, 20, 25, 30, 40, 50, 100, or more amino acid in length. In addition to activity, biologically active fragments also can be characterized by, for example, a motif, domain, or segment that has been identified by analysis of the polypeptide sequence using methods well known in the art. Such regions can include, for example, a signal peptide, extracellular domain, transmembrane segment, ligand binding region, zinc finger domain and/or glycosylation site.

The term "vaccine", as used herein, refers to a composition that can be administered to an animal to protect the animal against an infectious disease. Vaccines protect against diseases by inducing or increasing an immune response in an animal against the infectious disease. An exemplary infectious disease amenable to treatment with the vaccines of the invention is mucormycosis. The vaccine-mediated protection can be humoral and/or cell mediated immunity induced in host when a subject is challenged with, for example, FTR or an immunogenic portion or fragment thereof.

The term "adjuvant" is intended to mean a composition with the ability to enhance an immune response to an antigen generally by being delivered with the antigen at or near the site of the antigen. Ability to increase an immune response is manifested by an increase in immune mediated protection. Enhancement of humoral immunity can be determined by, for example, an increase in the titer of antibody raised to the antigen. Enhancement of cellular immunity can be measured by, for example, a positive skin test, cytotoxic T-cell assay, ELISPOT assay for IFN-gamma or IL-2. Adjuvants are well known in the art. Exemplary adjuvants include, for example, Freud's complete adjuvant, Freud's incomplete adjuvant, aluminum adjuvants, MF59 and QS21.

The term "antibody" as used herein refers to immunoglobulin molecules and immunologically active portion of immunoglobulin molecules. Antibodies can be prepared by any of a variety of techniques known to those skilled in the art (see, for example, Harlow and Lane, *Antibodies: A Laboratory Manual*, Cold Spring Harbor Laboratories, Cold Spring Harbor, N.Y., 1988). The present invention provides polyclonal and monoclonal antibodies that bind specifically to a polypeptide of the invention or fragment or variant thereof. Monoclonal antibodies of the invention, for example, include a population of antibody molecules that contain only one species of antigen binding site capable of immunoreacting with a particular epitope of a polypeptide of the invention or a fragment or variant thereof. Monoclonal antibodies can be coupled to one or more therapeutic agents. Suitable agents in this regard include differentiation inducers, drugs, toxins, and derivatives thereof. A therapeutic agent can be coupled (e.g., covalently bonded) to a suitable monoclonal antibody either directly or indirectly (e.g., via a linker group).

The terms "vector", "cloning vector" and "expression vector" mean the vehicle by which a nucleic acid can be introduced into a host cell. The vector can be used for propagation or harboring a nucleic acid or for polypeptide expression of an encoded sequence. A wide variety of vectors are known in the art and include, for example, plasmids, phages and viruses Exemplary vectors can be found described in, for example, Sambrook et al., *Molecular Cloning: A Laboratory Manual*, Third Ed., Cold Spring Harbor Laboratory, New York (2001); Ausubel et al., *Current Protocols in Molecular Biology*, John Wiley and Sons, Baltimore, Md. (1999).

The term "antibody inhibitor" as used herein refers to an antibody that reduces the biological activity or function of the target antigen (i.e., FTR). Such reduction in activity or function can be, for example, in connection with a cellular component (e.g., membrane localization), or in connection with a cellular process (e.g., iron transport), or in connection with an overall process of a cell (e.g., cell growth or survival). In reference to cell growth, the inhibitory effects can be fungicidal (killing of fungi) or fungistatic (i.e., stopping or at least slowing fungal growth). The latter slows or prevents fungal growth such that fewer fungi are produced relative to uninhibited fungi over a given time period. From a molecular standpoint, such inhibition can equate with a reduction in the level of, or elimination of, the transcription and/or translation of FTR molecule, or reduction or elimination of activity of FTR molecule.

The term "treating" or "treatment," as it is used herein is intended to mean an amelioration of a clinical symptom indicative of a fungal condition. Amelioration of a clinical symptom includes, for example, a decrease or reduction in at least one symptom of a fungal condition in a treated individual compared to pretreatment levels or compared to an individual with a fungal condition. The term "treating" also is intended to include the reduction in severity of a pathological condition, a chronic complication or an opportunistic fungal infection which is associated with a fungal condition. Such pathological conditions, chronic complications or opportunistic infections are exemplified below with reference to mucormycosis. Mucormycosis and other such pathological conditions, chronic complications and opportunistic infections also can be found described in, for example, Merck Manual, Sixteenth Edition, 1992, and Spellberg et al., *Clin. Microbio. Rev.* 18:556-69 (2005).

The term "preventing" or "prevention," as it is used herein is intended to mean a forestalling of a clinical symptom indicative of a fungal condition. Such forestalling includes, for example, the maintenance of normal physiological indicators in an individual at risk of infection by a fungus or fungi prior to the development of overt symptoms of the condition or prior to diagnosis of the condition. Therefore, the term "preventing" includes the prophylactic treatment of individuals to guard them from the occurrence of a fungal condition. Preventing a fungal condition in an individual also is intended to include inhibiting or arresting the development of the fungal condition. Inhibiting or arresting the development of the condition includes, for example, inhibiting or arresting the occurrence of abnormal physiological indicators or clinical symptoms such as those described above and/or well known in the art. Therefore, effective prevention of a fungal condition would include maintenance of normal body temperature, weight, psychological state as well as lack of lesions or other pathological manifestations in an individual predisposed to a fungal condition. Individuals predisposed to a fungal condition include, for example, an individual with AIDS, azotemia, diabetes mellitus, bronchiectasis, emphysema, TB, lymphoma, leukemia, or burns, or an individual with a history of susceptibility to a fungal condition. Inhibiting or arresting the development of the condition also includes, for example, inhibiting or arresting the progression of one or more pathological conditions, chronic complications or susceptibility to an opportunistic infection associated with a fungal condition.

The term "fungal condition" as used herein refers to fungal diseases, infection, or colonization including superficial mycoses (i.e., fungal diseases of skin, hair, nail and mucous membranes; for example, ringworm or yeast infection), subcutaneous mycoses (i.e., fungal diseases of subcutaneous tissues, fascia and bone; for example, mycetoma, chromomycosis, or sporotichosis), and systemic mycoses (i.e., deep-seated fungal infections generally resulting from the inhalation of air-borne spores produced by causal moulds; for example, zygomycosis, mucormycosis, coccidioidomycosis, blastomycosis, histoplasmosis, or paracoccidioidomycosis).

As used herein, the term "zygomycosis" is intended to mean a fungal condition caused by fungi of the class Zygomycetes, comprised of the orders Mucorales and Entomophthorales. The Entomophthorales are causes of subcutaneous and mucocutaneous infections known as entomophthoromycosis, which largely afflict immunocompetent hosts in developing countries. Zygomycosis is also referred to as mucormycosis and the two terms are used interchangeably to refer to similar types of fungal infections.

As used herein, the term "mucormycosis" is intended to mean a fungal condition caused by fungi of the order Mucorales. Mucormycosis is a life-threatening fungal infection almost uniformly affecting immunocompromised hosts in either developing or industrialized countries. Fungi belonging to the order Mucorales are distributed into at least six families, all of which can cause cutaneous and deep infections. Species belonging to the family Mucoraceae are isolated more frequently from patients with mucormycosis than any other family. Among the Mucoraceae, *Rhizopus oryzae* (*Rhizopus arrhizus*) is a common cause of infection. Other exemplary species of the Mucoraceae family that cause a similar spectrum of infections include, for example, *Rhizopus microsporus* var. *rhizopodiformis, Absidia corymbifera, Apophysomyces elegans, Mucor* species, *Rhizomucor pusillus* and *Cunninghamella* spp (Cunninghamellaceae family). Mucormycosis is well known in the art and includes, for example, rinocerebral mucormycosis, pulmonary mucormycosis, gastrointestinal mucormycosis, disseminated mucormycosis, bone mucormycosis, mediastinum mucormycosis, trachea mucormycosis, kidney mucormycosis, peritoneum mucormycosis, superior vena cava mucormycosis or external otitis mucormycosis.

Fungi belonging to the order Mucorales are currently distributed into the families of Choanephoraceae; Cunninghamellaceae; Mucoraceae; Mycotyphaceae; Phycomycetaceae; Pilobolaceae; Saksenaeaceae; Syncephalastraceae; and Umbelopsidaceae. Each of these fungi families consists of one or more genera. For example, fungi belonging to the order Mucorales, family Mucoraceae, are further classified into the genera of *Absidia* (e.g., *A. corymbifera*); *Actinomucor* (e.g., *A. elegans*); *Amylomyces* (e.g., *A. rouxii*); *Apophysomyces; Backusella* (e.g., *B. circina*); *Benjaminiella* (e.g., *B. multispora*); *Chaetocladium* (e.g., *C. brefeldii*); *Circinella* (e.g., *C. angarensis*); *Cokeromyces* (e.g., *C. recurvatus*); *Dicranophora* (e.g., *D. fulva*); *Ellisomyces* (e.g., *E. anomalus; Helicostylum* (e.g., *H. elegans*); *Hyphomucor* (e.g., *H. assamensis*); *Kirkomyces* (e.g., *K. cordensis*); *Mucor* (e.g., *M amphibiorum*); *Parasitella* (e.g., *P. parasitica*); *Philophora* (e.g., *P. agaricina*); *Pilaira* (e.g., *P. anomala*); *Pirella* (e.g., *P. circinans*); *Rhizomucor* (e.g., *R. endophyticus*); *Rhizopodopsis* (e.g., *R. javensis*); *Rhizopus; Sporodiniella* (e.g., *S. umbellata*); *Syzygites* (e.g., *S. megalocarpus*); *Thamnidium* (e.g., *T. elegans*); *Thermomucor* (e.g., *T. indicae-seudaticae*); and *Zygorhynchus* (e.g., *Z. californiensis*). The genus *Rhizopus*, for example, consists of *R. azygosporus; R. caespitosus; R. homothallicus; R. oryzae*; and *R. schipperae* species.

The Choanephoraceae family consists of fungi genera *Blakeslea* (e.g., *B. monospora*), *Choanephora* (e.g., *C. cucurbitarum*), *Gilbertella* (e.g., *G. hainanensis*), and *Poitrasia* (e.g., *P. circinans*). The Cunninghamellaceae family consists of genera *Chlamydoabsidia* (e.g., *C. padenii*); *Cunninghamella* (e.g., *C. antarctica*); *Gongronella* (e.g., *G. butleri*); *Halteromyces* (e.g., *H. radiatus*); and *Hesseltinella* (e.g., *H. vesiculosa*). The Mycotyphaceae family consists of fungi genus *Mycotypha* (e.g., *M. africana*). The Phycomycetaceae family consists of fungi genus *Phycomyces* (e.g., *P. blakesleeanus*) and *Spinellus* (e.g., *S. chalybeus*). The Pilobolaceae family consists of fungi genera *Pilobolus* (e.g., *P. longipes*) and *Utharomyces* (e.g., *U. epallocaulus*). The Saksenaeaceae family consists of fungi genera *Apophysomyces* (e.g., *A. elegans*) and *Saksenaea* (e.g., *S. vasiformis*). The Syncephalastraceae family consists of fungi genera *Dichotomocladium* (e.g., *D. elegans*); *Fennellomyces* (e.g., *F. gigacellularis*); *Mycocladus* (e.g., *M. blakesleeanus*); *Phascolomyces* (e.g., *P. articulosus*); *Protomycocladus* (e.g., *P. faisalabadensis*); *Syncephalastrum* (e.g., *S. monosporum*); *Thamnostylum* (e.g., *T. lucknowense*); *Zychaea* (e.g., *Z. mexicana*). Finally, the Umbelopsidaceae family consists of fungi genus *Umbelopsis* (e.g., *U. angularis*).

As used herein, the term "pharmaceutically acceptable carrier" includes any and all pharmaceutical grade solvents, buffers, oils, lipids, dispersion media, coatings, isotonic and absorption facilitating agents and the like that are compatible with the active ingredient. These pharmaceutically acceptable carriers can be prepared from a wide range of pharmaceutical grade materials appropriate for the chosen mode of administration, e.g., injection, intranasal administration, oral administration, etc. For the purposes of this invention, the terms "pharmaceutical" or "pharmaceutically acceptable" further refer to compositions formulated by known techniques to be non-toxic and, when desired, used with carriers or additives that can be safely administered to humans. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

The term "immunogenic amount" as used herein refers an effective amount of a particular epitope of a polypeptide of the invention or a fragment or variant thereof that can induce the host immune response against the polypeptide or the infectious agent expressing the polypeptide. This amount is generally in the range of 20 µg to 10 mg of antigen per dose of vaccine and depends on the subject to be treated, capacity of the subject's immune system to synthesize antibodies, and the degree of protection desired. The precise amount of immunogen required can be calculated by various methods such as, for example, antibody titration. The term effective amount refers to an amount of a compound or compositions that is sufficient to provide a desired result. Thus, as used to describe a vaccine, an effective amount refers to an amount of a compound or composition (e.g., an antigen) that is sufficient to produce or elicit a protective immune response. An effective amount with respect to an immunological composition is an amount that is sufficient to elicit an immune response, whether or not the response is protective.

The present invention, in part, relates to the discovery that FTR gene product is required for full virulence of a fungal pathogen such as R. oryzae in hematogenous dissemination or mucormycosis. Moreover, inhibition of FTR polypeptide formation in a host having mucormycosis conferred prolonged survival. As described herein, abrogation of FTR1 function resulted in diminished iron uptake and diminished virulence in vivo, and passive immunization with anti-Ftr1p antibody significantly improved survival in infected mice. As disclosed herein, [assive immunotherapy against FTR1 is a viable strategy to improve outcomes of these deadly infections.

Accordingly, different compositions are disclosed herein fpr effective inhibition of FTR molecule and/or its function in treating mucormycosis or other fungal diseases. These inhibitory compositions include vaccines, antisense, siRNA, antibodoy or any other compositions capable of effectively targeting and inhibiting the function of FTR. Such compositions will reduce and/or prevent the growth of the fungus in the infected tissues and will cause organism death. The compositions of the invention also are useful in prophylactic settings to decrease onset and/or prevent infection from occurring. In addition, any of the FTR inhibitory compositions disclosed herein can further be supplemented and/or combined with other known antifungal therapies including, for example, Amphotericin B or iron chelators. Exemplary iron chelators include Deferiprone and Deferasirox.

In one aspect, the invention provides a vaccine composition having an FTR polypeptide or an antigenic fragment or variant of the polypeptide. The vaccine composition also can include an adjuvant. In certain embodiments, the vaccine composition of the invention has an FTR polypeptide (SEQ ID NO: 2) shown in FIG. 2 or an antigenic fragment of the FTR polypeptide (e.g., REGLE (SEQ ID NO: 3) motif), a pharmaceutically acceptable carrier and/or an adjuvant. Similarly, the vaccine composition has an FTR polypeptide corresponding to the nucleotides shown in FIGS. 15-18. The formulation of the vaccine composition of the invention is effective in inducing protective immunity in a subject by stimulating both specific humoral (neutralizing antibodies) and effector cell mediated immune responses against fungal pathogens' FTRs. The vaccine composition of the invention is also used in the treatment or prophylaxis of fungal infections such as, for example, mucormycosis.

The vaccine of the present invention will contain an immunoprotective quantity of FTR antigens and is prepared by methods well known in the art. The preparation of vaccines is generally described in, for example, M. F. Powell and M. J. Newman, eds., "Vaccine Design (the subunit and adjuvant approach)," Plenum Press (1995); A. Robinson, M. Cranage, and M. Hudson, eds., "Vaccine Protocols (Methods in Molecular Medicine)," Humana Press (2003); and D. Ohagan, ed., "Vaccine Ajuvants: Preparation Methods and Research Protocols (Methods in Molecular Medicine)," Humana Press (2000).

FTR polypeptide, and peptide fragments or variants thereof can include immunogenic epitopes, which can be identified using methods known in the art and described in, for example, Geysen et al. Proc. Natl. Acad. Sci. USA 81: 3998 (1984)). Briefly, hundreds of overlapping short peptides, e.g., hexapeptides, can be synthesized covering the entire amino acid sequence of the target polypeptide (i.e., FTR). The peptides while still attached to the solid support used for their synthesis are then tested for antigenicity by an ELISA method using a variety of antisera. Antiserum against FTR protein can be obtained by known techniques, Kohler and Milstein, Nature 256: 495-499 (1975), and can be humanized to reduce antigenicity, see, for example, U.S. Pat. No. 5,693,762, or produced in transgenic mice leaving an unrearranged human immunoglobulin gene, see, for example, U.S. Pat. No. 5,877,397. Once an epitope bearing hexapeptide reactive with antibody raised against the intact protein is identified, the peptide can be further tested for specificity by amino acid substitution at every position and/or extension at both C and/or N terminal ends. Such epitope bearing polypeptides typically contain at least six to fourteen amino acid residues of SEQ ID NO: 2, and can be produced, for example, by polypeptide synthesis using methods well known in the art or by fragmenting an FTR polypeptide. With respect to the molecule used as immunogens pursuant to the present invention, those skilled in the art will recognize that the FTR polypeptide can be truncated or fragmented without losing the essential qualities as an immunogenic vaccine. For example, FTR polypeptide can be truncated to yield an N-terminal fragment by truncation from the C-terminal end with preservation of the functional properties of the molecule as an immunogen. Similarly, C-terminal fragments can be generated by truncation from the N-terminal end with preservation of the functional properties of the molecule as an immunogen. Other modifications in accord with the teachings and guidance provided herein can be made pursuant to this invention to create other FTR polypeptide functional fragments, immunogenic fragments, variants, analogs or derivatives thereof, to achieve the therapeutically useful properties described herein with the native protein.

The vaccine compositions of the invention further contain conventional pharmaceutical carriers. Suitable carriers are well known to those of skill in the art. These vaccine compositions can be prepared in liquid unit dose forms. Other optional components, e.g., pharmaceutical grade stabilizers, buffers, preservatives, excipients and the like can be readily selected by one of skill in the art. However, the compositions can be lyophilized and reconstituted prior to use. Alternatively, the vaccine compositions can be prepared in any manner appropriate for the chosen mode of administration, e.g., intranasal administration, oral administration, etc. The preparation of a pharmaceutically acceptable vaccine, having due regard to pH, isotonicity, stability and the like, is within the skill of the art.

The immunogenicity of the vaccine compositions of the invention can further be enhanced if the vaccine further comprises an adjuvant substance. Various methods of achieving adjuvant effect for the vaccine are known. General principles and methods are detailed in "The Theory and Practical Application of Adjuvants", 1995, Duncan E. S. Stewart-Tull (ed.), John Wiley & Sons Ltd, ISBN 0-471-95170-6, and also in "Vaccines: New Generationn Immunological Adjuvants", 1995, Gregoriadis G et al. (eds.), Plenum Press, New York, ISBN 0-306-45283-9, both of which are hereby incorporated by reference herein.

Preferred adjuvants facilitate uptake of the vaccine molecules by antigen presenting cells (APCs), such as dendritic cells, and activate these cells. Non-limiting examples are selected from the group consisting of an immune targeting adjuvant; an immune modulating adjuvant such as a toxin, a cytokine, and a mycobacterial derivative; an oil formulation; a polymer; a micelle forming adjuvant; a saponin; an immunostimulating complex matrix (ISCOM® matrix); a particle; DDA (dimethyldioctadecylammonium bromide); aluminium adjuvants; DNA adjuvants; and an encapsulating adjuvant. Liposome formulations are also known to confer adjuvant effects, and therefore liposome adjuvants are included according to the invention.

Another aspect of the invention relates to a vaccine composition having a vector containing a nucleotide sequence that is substantially complimentary to at least 12 contiguous nucleotides of FTR sequence (e.g., SEQ ID NO: 1) shown in FIGS. 1, 15-18, a transcription promoter, and a transcription terminator; wherein the promoter is operably linked to the FTR nucleotide sequence, and wherein the FTR nucleotide sequence is operably linked to the transcription terminator. The preparation of DNA vaccines is generally described in, for example, M. Saltzman, H. Shen, and J. Brandsma, eds., "DNA Vaccines (Methods in Molecular Medicine)," Humana Press (2006); H. Ertl, ed., "DNA Vaccines," Kluwer Academic/Plenum Publishers (2003). In one embodiment, the vaccine composition further contains pharmaceutically acceptable carrier and/or adjuvant. Combination of DNA vaccines with adjuvants have been shown to induce a stronger and more specific immune response in human (Hokey et al. *Springer Semin Immun* 28:267-279 (2006)). In general, the potency of DNA vaccines increases when combined with adjuvants that can provide additional immune stimuli. For example, chemokines such as, for example, MIP-1α when used as adjuvants for DNA vaccines have the ability to recruit a variety of cells including professional antigen presenting cells (APCs) to the immunization site. The requirement of APCs to the sites such as muscle where there are relatively low levels of APCs will greatly increase the potency of DNA vaccines for intramuscular injections. Cytokines such as, for example, GM-CSF when used as adjuvant for DNA vaccines can recruit dendritic cells and promote their survival at the immunization site. Molecular adjuvants such as, for example, Fas that induce cell death can also increase the potency and efficacy of DNA vaccines. Adjuvant-mediated apoptosis and necrosis have been shown to provide more antigens to APCs. Other molecules such as for example, poly(lactide-co-glycolide) (PLG) and heat shock proteins have also been shown to act as adjuvants for DNA vaccines. It is well known to those skilled in the art that adjuvants can be combined with DNA vaccines as intact molecules such as, for example, intact molecules, or as vectors expressing such molecules; for example, plasmids expressing GM-CSF.

In addition to vaccination of subjects susceptible to fungal infections such as mucormycosis, the vaccine compositions of the present invention can be used to treat, immunotherapeutically, subjects suffering from a variety of fungal infections. Accordingly, vaccines that contain one or more of FTR polynucleotides, polypeptides and/or antibody compositions described herein in combination with adjuvants, and that act for the purposes of prophylactic or therapeutic use, are also within the scope of the invention. In an embodiment, vaccines of the present invention will induce the body's own immune system to seek out and inhibit fungal FTR molecules.

Another aspect of the invention relates to a pharmaceutical composition for treating or preventing a fungal condition having an antisense, a small interfering RNA or antibody inhibitor of FTR selected from the group consisting of a nucleotide sequence that is substantially complimentary to a portion of an FTR sequence; a nucleotide sequence that is substantially complimentary to at least 12 contiguous nucleotide bases of FTR sequence; a nucleotide RNAi sequence that is substantially complimentary to at least 18 contiguous nucleotide bases of FTR sequence; an antibody or antibody fragment thereof that specifically binds to an FTR nucleotide sequence, polypeptide or a fragment thereof; and a pharmaceutically acceptable excipient or carrier. In one embodiment, the pharmaceutical composition further includes an adjuvant.

Antisense nucleic acid molecules of the invention can be designed using the nucleotide sequences of SEQ ID NO: 1, FIGS. 15-18, their complementary strands, and/or a portion or variant thereof, constructed using enzymatic ligation reactions by procedures known in the art of the genetic engineering. For example, an antisense nucleic acid molecule (e.g., an antisense oligonucleotide) can be chemically synthesized using naturally occurring nucleotides or variously modified nucleotides designed to hybridize with a control region of a gene (e.g., promoter, enhancer, or transcription initiation region) to inhibit the expression of the FTR gene through triple-helix formation. Alternatively, the antisense nucleic acid molecule can be designed to hybridize with the transcript of a gene (i.e., mRNA), and thus inhibit the translation of FTR by inhibiting the binding of the transcript to ribosomes. The antisense methods and protocols are generally described in, for example, C. Stein, A. Krieg, eds., "Applied Antisense Oligonucleotide Technology" Wiley-Liss, Inc. (1998); or U.S. Pat. Nos. 5,965,722; 6,339,066; 6,358,931; and 6,359,124.

The present invention also provides, as antisense molecules, nucleic acids or nucleotide sequences that contain a fragment, portion or variant that hybridizes under high stringency conditions to a nucleotide sequence including a nucleotide sequence selected from SEQ ID NO: 1, FIGS. 15-18, or their complementary strands. The nucleic acid fragments of the invention are at least about 12, generally at least about 15, 18, 21, or 25 nucleotides, and can be 40, 50, 70, 100, 200, or more nucleotides in length. Longer fragments, for example, 30 or more nucleotides in length, which encode antigenic polypeptides described hereinafter, are particularly useful, such as for the generation of antibodies.

Particular small nucleic acid molecules that are of use in the invention are short stretches of double stranded RNA that are known as short interfering RNAs (siRNAs). These interfering RNA (RNAi) allow for the selective inhibition of FTR gene function in vivo. In the present invention, RNAi has been used to knock-down FTR expression in a DKA mouse model of mucormycosis infection, and in doing so it demonstrates a dramatic effect on survival and protection against the infection. The RNAi approach relies on an innate cellular response to combat viral infection. In this process, double stranded mRNAs are recognized and cleaved by the dicer RNase resulting in 21-23 nucleotide long stretches of RNAi. These RNAis are incorporated into and unwound by the RNA-inducing silencing complex (RISC). The single antisense strand then guides the RISC to mRNA containing the complementary sequence resulting in endonucleolytic cleavage of the mRNA, see Elbashir et al. (Nature 411; 494-498 (2001)). Hence, this technique provides a means for the targeting and degradation of FTR mRNA in vivo in fungal pathogen infecting a subject.

The present invention further provides inhibitory antibodies (monoclonal or polyclonal) and antigen-binding fragments thereof, that are capable of binding to and inhibition of FTR function. The antibody inhibitors of the present invention can bind to FTR, or a portion, fragment, variant thereof, and interfere with or inhibit the protein function, i.e., iron transportation. Furthermore, such antibodies can bind to FTR and interfere with or inhibit the proper localization or conformation of the protein within the fungal membrane. An antibody, or antigen-binding fragment thereof, is said to "specifically bind," "immunologically bind," and/or is "immunologically reactive" to an FTR polypeptide of the invention if it reacts at a detectable level with the FTR polypeptide, and does not react detectably with unrelated polypeptides under similar conditions.

In addition, recombinant antibodies, such as chimeric and humanized antibodies, including both human and non-human portions, which can be made using standard recombinant DNA techniques, are within the scope of the invention. Also included within the term "antibody" are fragments, such as the Fab, F(ab'). The FTR specific monoclonal antibodies of the invention have specific binding activity to FTR, or a functional fragment thereof, in pathogenic fungi responsible for mucormycosis.

Monoclonal antibodies can be prepared using methods such as, for example, hybridoma, recombinant, phage display, and combinatorial antibody technologies or a combination thereof. The techniques and protocols for production of monoclonal antibodies are generally described in, for example, Harlow and lane, eds., "Antibodies: A laboratory Manual," Cold Spring harbor Laboratory Press (1999); Harlow et al., *Using Antibodies: A Laboratory Manual*, Cold Spring harbor Laboratory Press (1999); C. Borrebaeck, ed., *Antibody Engineering: A Practical Guide*, W.H. Freeman and Co., Publishers, pp. 130-120 (1991).

Moreover, portions or fragments or variants of the FTR nucleotide sequence identified herein (and the corresponding complete gene sequence) can be used in various ways as polynucleotide reagents. For example, these sequences can be used to identify and express recombinant polypeptides for analysis, characterization, or therapeutic use. The sequences can additionally be used as reagents in the screening and/or diagnostic assays described hereinafter, and can also be included as components of kits (e.g., diagnostic kits) for use in the screening and/or diagnostic assays.

The compositions of the present invention in inhibiting FTR can be applied to subjects who are suffering from a wide variety of fungal infections including zygomycosis and mucormycosis. The compositions of the invention can further be supplemented with other antifungal agents (e.g., Amphotericin, Deferiprone, Deferasirox). Alternatively, the compositions of the invention can be applied prophylactically to all subjects who are at high risk of developing mucormycosis or other fungal infections (e.g., via active immunization). This would not be considered an over treatment giving the high mortality and morbidity of mucormycosis in view of the current antifungal and surgical debridement treatment.

Further, the invention is also directed to host cells in which immunogenic FTR polypeptides or FTR inhibitory nucleotides (e.g., RNAi, antisense molecules) can be produced. The term "host cell" is understood to refer not only to the particular subject cell but also to the progeny or potential progeny of the foregoing cell. A host cell can be any prokaryotic (e.g., *E. coli*) or eukaryotic cell (e.g., yeast, insect cells, or mammalian cells, such as CHO or COS cells). Other suitable host cells are known to those skilled in the art. Vectors expressing such immunogenic inhibitory molecules can be introduced into prokaryotic or eukaryotic cells via conventional transfection or transformation techniques (see, Sambrook et al., *Molecular Cloning: A Laboratory Manual*, Cold Spring Harbor Laboratories, Cold Spring Harbor, N.Y., 1989).

According to another aspect of the present invention, any of the above-described compositions can be used for treating or prevention of a fungal condition. A fungal condition is an aberrant condition or infection causes by a pathogenic fungus. Symptoms of a fungal condition that can be ameliorated by a method of the invention include, for example, fever, chills, night sweats, anorexia, weight loss, malaise, depression and lung, skin or other lesions. Other symptoms or characteristic manifestations include, for example, dissemination from a primary focus, acute or subacute presentations, progressive pneumonia, fungemia, manifestations of extrapulmonary dissemination, chronic meningitis, progressive disseminated histoplasmosis as a generalized involvement of the reticuloendothelial system (liver, spleen, bone marrow) and blastomycosis as single or multiple skin lesions. Effective treatment of an individual with a fungal condition, for example, will result in a reduction one or more of such symptoms in the treated individual. Numerous other clinical symptoms of fungal conditions are well known in the art and also can be used as a measure of amelioration or reduction in the severity of a fungal condition using the methods of the invention described herein.

Diagnosis of a fungal condition can be confirmed by isolating causative fungi from, for example, sputum, urine, blood, bone marrow, or specimens from infected tissues. For example, fungal infections can be diagnosed histopathologically with a high degree of reliability based on distinctive morphologic characteristics of invading fungi and/or by immunohistochemistry and the like selective for identifying antigens. Assessment of the activity of the infection also can be based on cultures taken from many different sites, fever, leukocyte counts, clinical and laboratory parameters related to specific involved organs (eg, liver function tests), and immunoserologic tests. The clinical significance of positive sputum cultures also can be corroborated by confirmation of tissue invasion.

Fungal infection, or mycoses, of humans and animals include, for example, superficial fungal infections that affect the outer layers of skin; fungal infections of the mucous membranes including the mouth (thrush), vaginal and anal regions, such as those caused by *Candida albicans*, and fungal infections that affect the deeper layers of skin and internal organs are capable of causing serious, often fatal illness, such as those caused by, for example, *Rhizopus oryzae*. Fungal infections are well known in the art and include, for example, zygomycosis, mucormycosis, aspergillosis, cryptococcosis, candidiasis, histoplasmosis, coccidiomycosis, paracoccidiomycosis, fusariosis (hyalohyphomycoses), blastomycosis, penicilliosis or sporotrichosis. These and other fungal infections can be found described in, for example, Merck Manual, Sixteenth Edition, 1992, and in Spellberg et al., *Clin. Microbio. Rev.* 18:556-69 (2005).

The fungal conditions caused by fungi of the genus *Candida*, candidiasis, can occur, for example, in the skin and mucous membranes of the mouth, respiratory tract and/or vagina as well as invade the bloodstream, especially in immunocompromised individuals. Candidiasis also is known in the art as candidosis or moniliasis. Exemplary species of the genus *Candida* include, for example, *Candida albicans, Candida krusei, Candida tropicalis, Candida glabrata* and *Candida parapsilosis*.

The fungal diseases caused by the genus *Aspergillus* include, for example, allergic aspergillosis, which affects asthma, cystic fibrosis and sinusitis patients; acute invasive aspergillosis, which shows increased incidence in patients with weakened immunity such as in cancer patients, patients undergoing chemotherapy and AIDS patients; disseminated invasive aspergillosis, which is widespread throughout the body, and opportunistic *Aspergillus* infection, which is characterized by inflammation and lesions of the ear and other organs. *Aspergillus* is a genus of around 200 fungi. *Aspergillus* species causing invasive disease include, for example, *Aspergillus fumigatus* and *Aspergillus flavus*. *Aspergillus* species causing allergic disease include, for example, *Aspergillus fumigatus* and *Aspergillus clavatus*. Other exemplary *Aspergillus* infectious species include, for example, *Aspergillus terreus* and *Aspergillus nidulans*.

The fungal conditions such as, for example, zygomycosis and mucormycosis which are caused by saprophytic mould fungi include rinocerebral mucormycosis, pulmonary mucormycosis, gastrointestinal mucormycosis, disseminated mucormycosis, bone mucormycosis, mediastinum mucormycosis, trachea mucormycosis, kidney mucormycosis, peritoneum mucormycosis, superior vena cava mucormycosis or external otitis mucormycosis. Infectious agents causing mucormycosis are of the order Mucorales which include species from *Rhizopus* genus such as, for example, *Rhizopus oryzae* (*Rhizopus arrhizus*), *Rhizopus microsporus* var. *rhizopodiformis*; or species from *Absidia* genus such as, for example, *Absidia corymbifera*; or species from *Apophysomyces* genus such as, for example, *Apophysomyces elegans*; or species from Mucor genus such as, for example, *Mucor amphibiorum*; or species from *Rhizomucor* genus such as, for example, *Rhizomucor pusillus*; or species from *Cunninghamell* genus (in the Cunninghamellaceae family) such as, for example, *Cunninghamella bertholletiae*.

Various methods are described herein for effective inhibition of FTR molecule and/or its function in treatment of mucormycosis and other fungal diseases. These inhibiting methods involve vaccines, antisense, siRNA, antibody, or any other compositions capable of effectively targeting and inhibiting the function of FTR. Such methods will reduce or prevent the growth of the fungus in the infected tissues by inhibiting the main iron transporter that functions in supplying the pathogenic organism with iron. An immunotherapeutic inhibition of iron transportation using a soluble FTR polypeptide or functional fragment or a variant thereof is useful in this context because: (i) the morbidity and mortality associated with mucormycosis, for example, continues to increase, even with currently available antifungal therapy; (ii) a rising incidence of antifungal resistance is associated with the increasing use of antifungal agents; iii) the population of patients at risk for serious zygomycosis, mucormycosis, candidosis, or aspergillosis, for example, is well-defined and very large, and includes, e.g., post-operative patients, transplant patients, cancer patients, low birth weight infants, subjects with diabetes ketoacidosis (DKA) and other forms of metabolic acidosis, subjects receiving treatment with corticosteroids, subjects with neutropenia, trauma, burns, and malignant hematological disorders, and subjects receiving deferoxamine chelation-therapy or hemodialysis; and iv) a high percentage of the patients who develop serious fungal infections are not neutropenic, and thus can respond to a vaccine or a competitive polypeptide or compound inhibitor. For these reasons, Zygomycetes or *Candida*, for example, are fungal targets for passive immunotherapy, active immunotherapy or a combination of passive or active immunotherapy.

Figure 4:
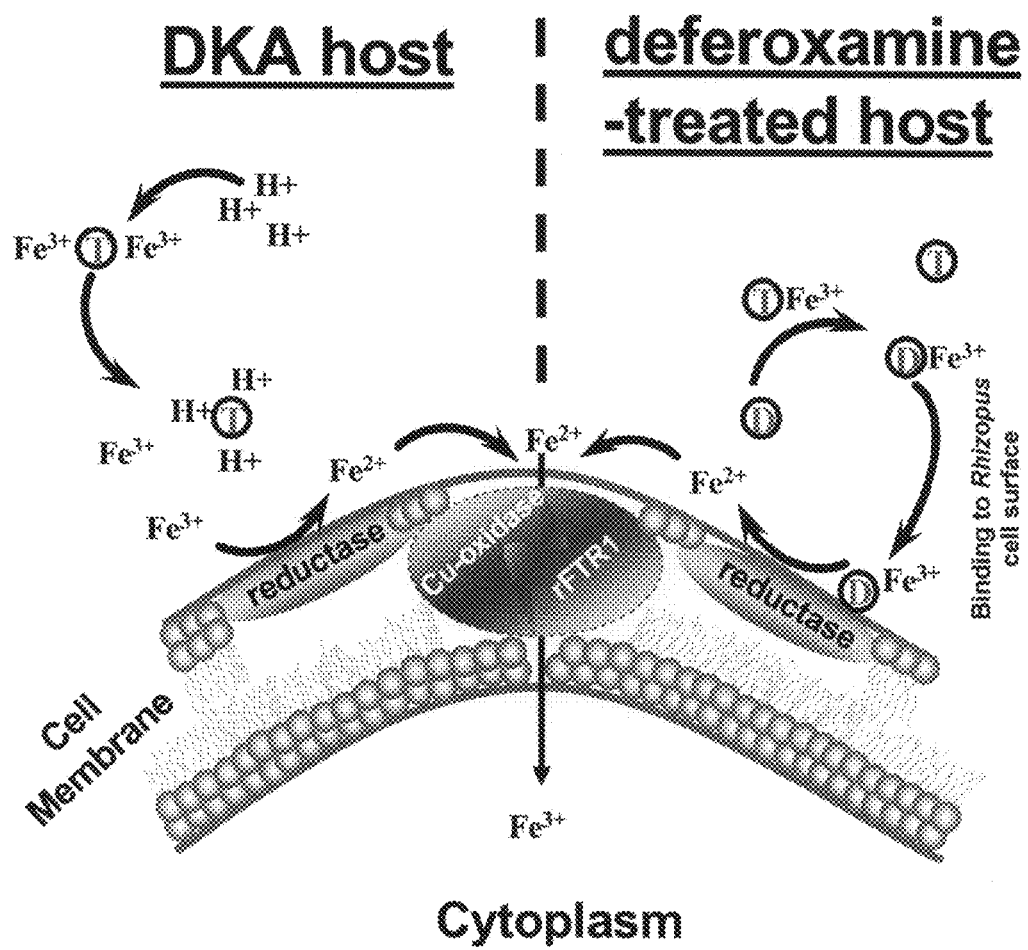
FIG. 4 shows mechanisms of iron uptake by Zygomycetes in conditions of elevated available serum iron.

Mechanistically, FTR polypeptide physically complexes with copper oxidase in yeast, transports ferric iron nearly simultaneously to the oxidation step. In subjects with DKA, low pH conditions cause proton-mediated displacement of ferric iron ($Fe^{3+}$) from serum carrier molecules, including transferrin (T). See FIG. 4. $Fe^{3+}$ is then reduced at the cell surface to ferrous iron ($Fe^{2+}$). In contrast, deferoxamine (D) directly chelates iron from transferrin, resulting in ferrioxamine (iron-deferoxamine complex). Ferrioxamine then binds to unidentified receptor(s) on the surface of fungi, e.g., Zygomycetes. The fungus then liberates ferrous iron from ferrioxamine by reduction at the cell surface. In both cases, ferrous iron is reoxidized back to ferric iron by copper oxidase (Cu-oxidase).

Therefore, the methods of the present invention in inhibiting FTR can be applied to subjects who are suffering from a wide variety of fungal infections including zygomycosis and mucormycosis. The methods of the invention can further be supplemented with other antifungal agents (e.g., Amphotericin, Deferiprone, Deferasirox). Alternatively, the methods of the invention can be applied prophylactically to all subjects who are at high risk of developing mucormycosis or other fungal infections (e.g., via active immunization). This would not be considered an over treatment giving the high mortality and morbidity of mucormycosis in view of the current antifungal and surgical debridement treatment.

Accordingly, in one aspect, the invention provides a method of treating or preventing disseminated mucormycosis or other fungal diseases. The method includes administering an immunogenic amount of a vaccine having an FTR polypeptide (SEQ ID NO: 2) shown in FIG. 2, or an antigenic or immunogenic fragment of the polypeptide or a variant thereof in a pharmaceutically acceptable medium. The preparation of vaccines is generally described in, for example, M. F. Powell and M. J. Newman, eds., "Vaccine Design (the subunit and adjuvant approach)," Plenum Press (1995); A. Robinson, M. Cranage, and M. Hudson, eds., "Vaccine Protocols (Methods in Molecular Medicine)," Humana Press (2003); and D. Ohagan, ed., "Vaccine Ajuvants: Preparation Methods and Research Protocols (Methods in Molecular Medicine)," Humana Press (2000).

The FTR polypeptide, or an antigenic or immunogenic fragment of the polypeptide or a variant thereof can be derived from different pathogenic fungal species of *Zygomycetes* such as *Rhizopus oryzae* (*Rhizopus arrhizus*), *Rhizopus microsporus* var. *rhizopodiformis*, *Absidia corymbifera*, *Apophysomyces elegans, Mucor* species, *Rhizomucor pusillus* and *Cunninghamella* spp (Cunninghamellaceae family); or from different *Candida* species such as *Candida albicans, Candida krusei, Candida tropicalis, Candida glabrata,* and *Candida parapsilosis*; or from different *Aspergillus* species such as *Aspergillus fumigatus, Aspergillus niger, Aspergillus flavus, Aspergillusterreus,* and *Aspergillus nidulans*. Administration of a vaccine of the invention will result in inhibition of the growth and/or virulence of fungal pathogen in a subject.

The sequence homology of, for example, FTR of *R. oryzae* with that of *S. cerevisiae* and *C. albicans* are described further below in Example I. Given the teachings and guidance provided herein, those skilled in the art will understand that the vaccines and methods of the invention can be applied to the treatment of mucormycosis or other fungal infections alike. Similarly, given the teachings and methods described herein, those skilled in the art also will understand that the vaccines and methods of the invention also can be applied to other pathogens having iron permease polypeptides with similar immunogenicity, sequence and/or structural homology to the FTR protein described herein, including fungus, bacteria and the like.

The vaccine compositions are administrated in a manner compatible with the dosage formulation and in such amount as will be prophylactically effective with or without an adjuvant. The quantity to be administered, which is generally in the range of 1 to 10 mg, preferably 1 to 1000 µg of antigen per dose, depends on the subject to be treated, capacity of the subject's immune system to synthesize antibodies, and the degree of protection desired. Precise amounts of active ingredient required to be administered can depend on the judgement of the practitioner and can be peculiar to each subject. Moreover, the amount of polypeptide in each vaccine dose is selected as an immunogenic amount which induces an immunoprotective response. Particularly useful immunogenic amounts include an amount of FTR polypeptide that also is devoid of significant, adverse side effects. Such amount will vary depending upon the immunogenic strength of an FTR polypeptide selected for vaccination. Useful immunogenic amounts of an FTR polypeptide or immunogenic fragment thereof include, for example, doses ranging from about 1-1000 μg. In certain embodiments, useful immunogenic amounts of an FTR polypeptide or immunogenic fragment thereof include about 2-100 μg, and particularly useful dose ranges can range from about 4-40 μg, including for example, 5, 6, 7, 8, 9, 10, 12, 15, 20, 25, 30, 35 and 40 μg as well as all values in between the above exemplified amounts. An optimal immunogenic amount for a selected FTR polypeptide vaccine of the invention can be ascertained using methods well known in the art such as determination of antibody titres and other immune responses in subjects as exemplified previously. Following an initial vaccination, subjects receive a boost in about 3-4 weeks. Vaccine delivery methods is further described, for example, in S. Cohen and H. Bernstein, eds., "Microparticulate Systems for the Delivery of Proteins and Vaccines (Drugs and The Pharmaceutical Sciences)," Vol. 77, Marcel Dekker, Inc. (1996). Encapsulation within liposomes is described, for example, by Fullerton, U.S. Pat. No. 4,235,877. Conjugation of proteins to macromolecules is disclosed, for example, by Likhite, U.S. Pat. No. 4,372,945 and by Armor et al., U.S. Pat. No. 4,474,757.

Furthermore, the vaccine compositions of the present invention include DNA vaccines encoding antigenic FTR molecules. As mentioned earlier, the preparation of DNA vaccines is generally described in, for example, M. Saltzman, H. Shen, and J. Brandsma, eds., "DNA Vaccines (Methods in Molecular Medicine)," Humana Press (2006); H. Ertl, ed., "DNA Vaccines," Kluwer Academic/Plenum Publishers (2003). DNA vaccines can be introduced into the host cells of the subject by a variety of expression systems. These expression systems include prokaryotic, mammalian, and yeast expression systems. For example, one approach is to utilize a viral vector, such as vaccinia virus incorporating the new genetic material, to innoculate the host cells. Alternatively, the genetic material can be incorporated in a vector or can be delivered directly to the host cells as a "naked" polynucleotide, i.e. simply as purified DNA. In addition, the DNA can be stably transfected into attenuated bacteria such as *Salmonella typhimurium*. When a subject is orally vaccinated with the transformed *Salmonella*, the bacteria are transported to Peyer's patches in the gut (i.e., secondary lymphoid tissues), which then stimulate an immune response. In addition, DNA vaccines can be delivered by variety of well-known delivery vehicles such as, for example, lipid monolayers, bilayers, or vesicles such as liposomes. Agents such as saponins and block-copolymers, which are commonly used to permeabilize cells, can also be used with DNA vaccines. As described earlier, DNA vaccine compositions of the invention can include pharmaceutically acceptable carriers and/or adjuvants.

The DNA vaccine compositions as described herein can be administered by a variety of routes contemplated by the present invention. Such routes include intranasal, oral, rectal, vaginal, intramuscular, intradermal and subcutaneous administration.

The DNA vaccine compositions for parenteral administration include sterile aqueous or non-aqueous solutions, suspensions or emulsions, the protein vaccine, and an adjuvant as described herein. The composition can be in the form of a liquid, a slurry, or a sterile solid which can be dissolved in a sterile injectable medium before use. The parenteral administration is preferably intramuscular. Intramuscular inoculation involves injection via a syringe into the muscle. This injection can be via a syringe or comparable means. The vaccine composition can contain a pharmaceutically acceptable carrier and/or an adjuvant. Alternatively, the present vaccine compositions can be administered via a mucosal route, in a suitable dose, and in, a liquid form. For oral administration, the vaccine composition can be administered in liquid, or solid form with a suitable carrier.

The invention also provides a method of treating or preventing a fungal condition in a subject in need thereof, including exposing said fungi to an antisense against FTR. In one embodiment, the antisense includes a nucleotide sequence that is substantially complimentary to a portion of an FTR nucleotide sequence. In another embodiment the nucleotide sequence of the antisense is substantially complimentary to at least 12 contiguous nucleotide bases of FTR sequence.

The antisense oligonucleotides used in accordance with this invention can be conveniently and routinely made through the well-known technique of solid phase synthesis. Equipment for such synthesis is sold by several vendors including Applied Biosystems. Any other means for such synthesis can also be employed, however the actual synthesis of the oligonucleotides are well within the talents of those skilled in the art. It is also well known to use similar techniques to prepare other oligonucleotides such as the phosphorothioates and alkylated derivatives. As described earlier, an antisense nucleic acid molecule (e.g., an antisense oligonucleotide) can be chemically synthesized using naturally occurring nucleotides or variously modified nucleotides designed to hybridize with a control region of a gene (e.g., promoter, enhancer, or transcription initiation region) to inhibit the expression of the FTR gene through triple-helix formation. Alternatively, the antisense nucleic acid molecule can be designed to hybridize with the transcript of FTR (i.e., mRNA), and thus inhibit the translation of FTR by inhibiting the binding of the transcript to ribosomes. The antisense methods and protocols are generally described in, for example, C. Stein, A. Krieg, eds., "Applied Antisense Oligonucleotide Technology" Wiley-Liss, Inc. (1998); or U.S. Pat. Nos. 5,965,722; 6,339,066; 6,358,931; and 6,359,124.

The antisense compositions of the invention can be delivered to a subject in need thereof with variety of means known in the art. For example, microparticles such as polystyrene microparticles, biodegradable particles, liposomes or microbubbles containing the antisense compositions in releasable form can be used for direct delivery of the compositions into tissues via injection. In some embodiments of the invention, the antisense oligonucleotides can be prepared and delivered in a viral vector such as hepatitis B virus (see, for example, Ji et al., J. Viral Hepat. 4:167 173 (1997)); in adenoassociated virus (see, for example, Xiao et al. Brain Res. 756:76 83 (1997)); or in other systems including but not limited to an HVJ (Sendai virus)-liposome gene delivery system (see, for example, Kaneda et al. Ann. N.Y. Acad. Sci. 811:299 308 (1997)); a "peptide vector" (see, for example, Vidal et al. CR Acad. Sci III 32):279 287 (1997)); as a gene in an episomal or plasmid vector (see, for example, Cooper et al. Proc. Natl. Acad. Sci. U.S.A. 94:6450 6455 (1997), Yew et al. Hum Gene Ther. 8:575 584 (1997)); as a gene in a peptide-DNA aggregate (see, for example; Niidome et al. J. Biol. Chem. 272:15307 15312 (1997)); as "naked DNA" (see, for example, U.S. Pat. No. 5,580,859 and U.S. Pat. No. 5,589, 466); in lipidic vector systems (see, for example, Lee et al. Crit Rev Ther Drug Carrier Syst. 14:173 206 (1997)); polymer coated liposomes (Marin et al., U.S. Pat. No. 5,213,804 issued Can 25, 1993; Woodle et al., U.S. Pat. No. 5,013,556 issued Can 7, 1991); cationic liposomes (Epand et al., U.S. Pat. No. 5,283,185 issued Feb. 1, 1994; Jessee, J. A. U.S. Pat. No. 5,578,475 issued Nov. 26, 1996; Rose et al, U.S. Pat. No. 5,279,833 issued Jan. 18, 1994; Gebeyehu et al., U.S. Pat. No. 5,334,761 issued Aug. 2, 1994); gas filled microspheres (Unger et al., U.S. Pat. No. 5,542,935 issued Aug. 6, 1996), ligand-targeted encapsulated macromolecules (Low et al. U.S. Pat. No. 5,108,921 issued Apr. 28, 1992; Curiel et al., U.S. Pat. No. 5,521,291 issued Can 28, 1996; Groman et al., U.S. Pat. No. 5,554,386 issued Sep. 10, 1996; Wu et al., U.S. Pat. No. 5,166,320 issued Nov. 24, 1992).

The invention also provides a method of treating or preventing a fungal condition in a subject in need thereof, including exposing said fungi to a small interfering RNA against FTR. In one embodiment, a nucleotide RNAi sequence that is substantially complimentary to at least 18 contiguous nucleotide bases of FTR sequence is used that is capable of binding to an FTR nucleotide sequence or a fragment thereof.

Double-stranded RNA (dsRNA) also known as small-interfering RNA (siRNA) induces sequence-specific post-transcriptional gene silencing in many organisms by a process known as RNA interference (RNAi). In the present invention, as described in Example 9, RNAi has been prepared and used to knock-down FTR expression in a DKA mouse model of mucormycosis infection, and in doing so it demonstrates a dramatic effect on survival and protection against the infection.

The siRNA is usually administered as a pharmaceutical composition. The administration can be carried out by known methods, wherein a nucleic acid is introduced into a desired target cell in vitro or in vivo. Commonly used gene transfer techniques include calcium phosphate, DEAE-dextran, electroporation and microinjection and viral methods (Graham et al. Virol. 52, 456 (1973); McCutchan et al. J. Natl. Cancer Inst. 41, 351(1968); Chu et al. Nucl. Acids Res. 15, 1311 (1987); Fraley et al. J. Biol. Chem. 255, 10431 (1980); Capecchi, Cell 22, 479 (1980); and cationic liposomes (Feigner et al. Proc. Natl. Acad. Sci USA 84, 7413 (1987)). Commercially available cationic lipid formulations are e.g. Tfx 50™ (Promega) or Lipofectamin2000™ (Invitrogen).

The invention also provides a method of treating or preventing a fungal condition in a subject in need thereof, including an antibody inhibitor of FTR. In one embodiment, the antibody inhibitor of FTR is an antibody or antibody fragment that specifically binds to an FTR nucleotide polypeptide or a fragment thereof.

As described earlier the antibody inhibitors of FTR are are capable of binding to and inhibition of FTR function. The antibody inhibitors of the present invention can bind to FTR, a portion, fragment, or variant thereof, and interfere with or inhibit the protein function, i.e., iron transportation. These antibodies can inhibit FTR by negatively affecting, for example, the protein's proper membrane localization, folding or conformation, its substrate binding ability.

The antibodies of the present invention can be generated by any suitable method known in the art. Polyclonal antibodies against FTR can be produced by various procedures well known in the art. For example, an FTR peptide antigenic can be administered to various host animals including, but not limited to, rabbits, mice, rats, etc. to induce the production of sera containing polyclonal antibodies specific for the antigen. Various adjuvants can be used to increase the immunological response, depending on the host species, and include but are not limited to, Freund's (complete and incomplete), mineral gels such as aluminum hydroxide, alum (ALHYDROGEL), surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*. Such adjuvants are also well known in the art.

FTR peptide antigens suitable for producing antibodies of the invention can be designed, constructed and employed in accordance with well-known techniques. See, e.g., ANTIBODIES: A LABORATORY MANUAL, Chapter 5, p. 75-76, Harlow & Lane Eds., Cold Spring Harbor Laboratory (1988); Czernik, *Methods In Enzymology,* 201: 264-283 (1991); Merrifield, *J. Am. Chem. Soc.* 85: 21-49 (1962)). Monoclonal antibodies of the present invention can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563-681 (Elsevier, N.Y., 1981) (said references incorporated by reference in their entireties).

The antibodies of the present invention can also be generated using various phage display methods known in the art. In phage display methods, functional antibody domains are displayed on the surface of phage particles which carry the polynucleotide sequences encoding them. In a particular embodiment, such phage can be utilized to display antigen binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include those disclosed in U.S. Pat. Nos. 5,698,426; 5,223, 409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

The antibodies of the invention can be assayed for immunospecific binding by any method known in the art. The immunoassays which can be used include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art. See, e.g., Sambrook, Fitsch & Maniatis, *Molecular Cloning: A Laboratory Manual*, Second Edition Cold Spring Harbor Laboratory Press, Cold Spring Harbor, N.Y. (1989).

Specific binding can be determined by any of a variety of measurements known to those skilled in the art including, for example, affinity ($K_a$ or $K_d$), association rate ($k_{on}$), dissociation rate ($k_{off}$), avidity or a combination thereof Antibodies of the present invention can also be described or specified in terms of their binding affinity to FTR. Preferred binding affinities include those with a dissociation constant or $K_d$ less than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10 \times^{-5}$ M, $5 \times 10^{-6}$ M, $10^{-6}$ M, $5 \times 10^{-7}$ M, $10^{7}$ M, $5 \times 10^{-8}$ M, $10^{-8}$ M, $5 \times 10^{-9}$ M, $10^{-9}$ M, $5 \times 10^{-10}$ M, $10 \times^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, or $10^{-15}$ M.

An exemplary approach in which the antibodies of the present invention can be used as FTR inhibitors includes binding to and inhibiting FTR polypeptides locally or systemically in the body or by direct cytotoxicity of the antibody, e.g. as mediated by complement (CDC) or by effector cells (ADCC). The antibodies of this invention can be advantageously utilized in combination with other monoclonal or chimeric antibodies, or with lymphokines or hematopoietic growth factors (such as, e.g., IL-2, IL-3 and IL-7), for example, which serve to increase the number or activity of effector cells which interact with the antibodies.

The antibodies of the invention can be administered alone or in combination with other types of treatments such as, for example, anti-fungal therapies. In one embodiment, FTR inhibitor antibodies are administered to a human patient for therapy or prophylaxis.

Various delivery systems are known and can be used to administer the antibody inhibitors of the invention, e.g., encapsulation in liposomes, microparticles, microcapsules, recombinant cells capable Methods of introduction include but are not limited to intradermal, intramuscular, intraperitoneal, intravenous, subcutaneous, intranasal, epidural, and oral routes. The compounds or compositions can be administered by any convenient route, for example by infusion or bolus injection, by absorption through epithelial or mucocutaneous linings (e.g., oral mucosa, rectal and intestinal mucosa, etc.) and can be administered together with other biologically active agents. Administration can be systemic or local. Pulmonary administration can also be employed, e.g., by use of an inhaler or nebulizer, and formulation with an aerosolizing agent.

For antibodies, the dosage administered to a subject is typically 0.1 mg/kg to 100 mg/kg of the subject's body weight. Preferably, the dosage administered to a subject is between 0.1 mg/kg and 20 mg/kg of the subject's body weight, more preferably 1 mg/kg to 10 mg/kg of the subject's body weight. Generally, humanized or human antibodies have a longer half-life within the human body than antibodies from other species due to the immune response to the foreign polypeptides. Thus, lower dosages of humanized antibodies and less frequent administration is often possible. Further, the dosage and frequency of administration of antibodies of the invention can be reduced by enhancing uptake and tissue penetration (e.g., into the brain) of the antibodies by modifications such as, for example, lipidation.

In pharmaceutical dosage forms, the compositions of the invention including vaccine, antisense, siRNA and antibodies can be used alone or in appropriate association, as well as in combination, with each other or with other pharmaceutically active compounds. Administration of the agents can be achieved in various ways, including oral, buccal, nasal, rectal, parenteral, intraperitoneal, intradermal, transdermal, subcutaneous, intravenous, intra-arterial, intracardiac, intraventricular, intracranial, intratracheal, and intrathecal administration, etc., or otherwise by implantation or inhalation. Thus, the subject compositions can be formulated into preparations in solid, semi-solid, liquid or gaseous forms, such as tablets, capsules, powders, granules, ointments, solutions, suppositories, enemas, injections, inhalants and aerosols. The following methods and excipients are merely exemplary and are in no way limiting.

Any of treatment modalities disclosed herein can be combined and administered to a subject suffering from a fungal infection or being at risk for developing a fungal infection (prophylactic vaccination or treatment). In a combination therapy, for example, a subject can first receive a vaccine of the invention to generate an immune response towards the fungi, then an antisense, siRNA and/or antibody that can target FTR of the fungi and further augment the fungal treatment. In one embodiment of the treatment, the vaccine of the invention is used in combination with an antisese, siRNA and/or antibody against FTR for treating or preventing a fungal condition such as, for example, mucormycosis. In another embodiment, the antibodies of the invention are used in combination with antisense and/or siRNA for treating the fungal condition.

The compositions of the inventions, either alone or in combination, can further be combined one or more methods or compositions available for fungal therapy. In one embodiment, the compositions of the invention can be used in concert with a surgical method to treat a fungal infection. In yet another embodiment, the compositions of the invention can be used in combination with a drug or radiation therapy for treating a fungal condition. Antifungal drugs that are useful for combination therapy with the compositions of the invention include, but are not limited to, amphotericin B, iron chelators such as, for example, deferasirox, deferiprone, POSACONAZOLE®, FLUCONAZOLE®, ITRACONAZOLE® and/or KETOCONAZOLE®. Radiations useful in combination therapies for treating fungal infections include electromagnetic radiations such as, for example, near infrared radiation with specific wavelength and energy useful for treating fungal infections. In combination therapy, chemotherapy or irradiation is typically followed by administration of the vaccine in such a way that the formation of an effective anti-fungal immune response is not compromised by potential residual effects of the prior treatment.

In a further embodiment of combination therapy, the compositions of the invention can be combined with immunocytokine treatments. Without wishing to be bound by theory, it is believed that, for example, a vaccine generates a more effective immune response against, for example, an infection when a cytokine promoting the immune response is present at the site of the infection. For example, useful immunocytokines are those that elicit Th1 response, such as IL-2 or IL-12. During a combination therapy, for example, a subject can first receive a vaccine of the invention to generate an immune response towards a fungal infection, then an immunocytokine that can target the fungi and support the immune response in fighting the infection. Preferred immunocytokines typically have, for example, an antibody moiety that recognizes a surface antigen characteristic of the fungi such as, for example, FTR. Immunocytokines typically also have a cytokine moiety such as IL-2, IL-12, or others that preferentially direct a Th1 response. Immunocytokines suitable for the invention are described in U.S. Pat. No. 5,650,150, the contents of which are hereby incorporated by reference.

In another embodiment of combination therapy, combinations of the compositions of the invention can be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second. In another specific embodiment, compositions of the invention are used in any combination with amphotericin B, deferasirox, deferiprone, POSACONAZOLE®, FLUCONAZOLE®, ITRACONAZOLE®, and/or KETOCONAZOLE® to prophylactically treat, prevent, and/or diagnose an opportunistic fungal infection.

The invention, therefore, provides methods of treatment, inhibition and prophylaxis by administration to a subject of an effective amount of one or more compounds or pharmaceutical compositions of the invention. In a preferred aspect, the compositions of the invention are substantially purified (e.g., substantially free from substances that limit their effect or produce undesired side-effects). The subject is preferably an animal, including but not limited to animals such as cows, pigs, horses, chickens, cats, dogs, etc., and is preferably a mammal, and most preferably human.

As discussed above, various delivery systems are known and can be used to administer the compositions of the invention. The compositions can be administered by any convenient route, for example by infusion or bolus injection, by absorption through epithelial or mucocutaneous linings (e.g., oral mucosa, rectal and intestinal mucosa, etc.) and can be administered together with other biologically active agents. Administration can be systemic or local.

In a specific embodiment, it can be desirable to administer the pharmaceutical compounds or compositions of the invention locally to the area in need of treatment; this can be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including a vaccine or antibody, of the invention, care must be taken to use materials to which the protein does not absorb. In another embodiment, the compound or composition can be delivered in liposomes. In yet another embodiment, the compounds or compositions can be delivered in a controlled release system.

In an embodiment, the compositions are formulated in accordance with routine procedures as a pharmaceutical composition adapted for intravenous administration to human beings. Typically, compositions for intravenous administration are solutions in sterile isotonic aqueous buffer. Where necessary, the composition can also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule indicating the quantity of active agent. Where the compositions are to be administered by infusion, they can be dispensed with an infusion bottle containing sterile pharmaceutical grade water or saline. Where the compositions are administered by injection, an ampoule of sterile water for injection or saline can be provided so that the ingredients can be mixed prior to administration.

The compounds of the invention can also be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of the compounds or compositions of the invention which will be effective in the treatment, inhibition and prevention of a fungal disease or condition can be determined by standard clinical techniques. In addition, in vitro assays can optionally be employed to help identify optimal dosage ranges. The precise dose to be employed in the formulation will also depend on the route of administration, and the seriousness of the disease or condition, and should be decided according to the judgment of the practitioner and each subject's circumstances. Effective doses can be extrapolated from dose-response curves derived from in vitro or animal model test systems.

The following Examples illustrate the therapeutic utility of the FTR as the basis for preventive measures or treatment of disseminated mucormycosis. Example 1 describes cloning and identification of FTR. Example 2 describes FTR expression in R. oryzae under iron-depleted condition. Example 3 describes FTR expression in S. cerevisiae ftr1 null mutant. Example 4 describes FTR function in S. cerevisiae ftr1 null mutant. Example 5, describes development of animal model of mucormycosis. Example describes the effect of serum iron availability on susceptibility of DKA mice to R. oryzae. Example 7 describes the expression of FTR in vivo in DKA mice infected with R. oryzae. Example 8 describes FTR polypeptide and its homology to other proteins. Example 9 describes the role of FTR gene product in virulence of R. oryzae in the DKA mouse model of hematogenous dissemination of mucormycosis.

It is understood that modifications which do not substantially affect the activity of the various embodiments of this invention are also included within the definition of the invention provided herein. Accordingly, the following examples are intended to illustrate but not limit the present invention.

Example 1

Cloning and Identification of FTR

This Example describes the cloning and identification of FTR of R. oryzae which showed considerable sequence homology to high affinity iron permeases of S. cerevisiae and C. albicans (FIG. 3).

The following describes materials and methods used in the procedures described in this example. In accordance with the present invention, there can be employed conventional molecular biology, microbiology and recombinant DNA techniques within the skill of the art. Such techniques are explained fully in the literature. See, e.g., Sambrook, Fitsch & Maniatis, *Molecular Cloning: A Laboratory Manual*, Second Edition Cold Spring Harbor Laboratory Press, Cold Spring Harbor, N.Y. (1989).

Rhizopus oryzae 99-880 was obtained from the Fungus Testing Laboratory (University of Texas Health Science Center at San Antonio). This strain was isolated from a brain abscess in a diabetic subject with rhinocerebral mucormycosis.

To clone the FTR of R. oryzae, we used degenerate primers designed from the conserved regions of the S. cerevisiae FTR to amplify a 0.6 kb fragment from R. oryzae genomic DNA. This fragment showed 43% homology to S. cerevisiae FTR and hybridized to a 2.0 kb fragment of R. oryzae genomic DNA cut with EcoRI. We used this PCR-generated fragment to screen an R. oryzae genomic library made in λ-phage. Five different plaques were isolated and each contained a 2 kb fragment upon treatment with different restriction enzymes. Sequence analysis of this 2.0 kb genomic clone revealed a single open reading frame of 1101 bp that lacked introns. Comparison of the putative FTR polypeptide with those of other proteins in GenBank data-base revealed 46% and 44% identity to known fungal high affinity iron permeases from C. albicans and S. cerevisiae, respectively (Fu et al. *FEMS Micorbiol. Lett.* 235:169-176 (2004)). Multiple regions of the predicted amino acid sequence of FTR polypeptide showed significant homology with putative transmembrane domains from S. cerevisiae and C. albicans FTR. Importantly, the putative REGLE motif (SEQ ID NO:3) in which the glutamic acid residue is believed to interact directly with iron was conserved in the predicted amino acid sequences of FTR polypeptide from the three organisms and was embedded in a hydrophobic region of the protein. Additionally, Southern blot analysis of R. oryzae genomic DNA cut with EcoRI, DraI, or EcoRI+DraI and probed with the ORF of FTR confirmed the gene map of the FTR. Southern blot analysis of R. oryzae gDNA using the ORF of FTR under low stringency did not reveal any other bands, thus indicating that the FTR is not a member of a gene family (data not shown).

Example 2

Expression of FTR in R. oryzae Under Iron-Depleted Conditions

This Example shows that FTR is expression at higher levels under iron-depleted conditions.

Figure 5:
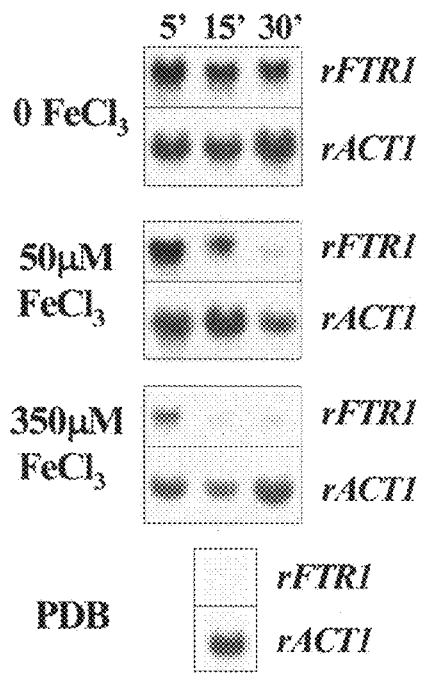
FIG. 5 shows the FTR expression in *R. oryzae* grown in media with varying concentrations of iron.

Expression of high affinity iron permeases is usually induced in iron-limited environments and suppressed in iron-rich environments. To verify that FTR polypeptide functions as a high-affinity iron permease, we examined FTR expression in response to different concentrations of $FeCl_3$. R. oryzae mycelia were collected by filtration and used to inoculate potato dextrose broth (PDB) supplemented with the iron chelators, 1 mM ferrozine and 100 µM of 2,2'bipyridyl, to induce iron starvation. The mycelia were transferred to PDB previously chelated for iron, and supplemented with varying concentrations of $FeCl_3$ and incubated at 37° C. for selected intervals. As expected, FTR expression was induced at all time points when the organism was exposed to media deficient in $FeCl_3$. The addition of $FeCl_3$ resulted in rapid suppression of FTR expression as early as 5 minutes after exposure. Further, this suppression of FTR expression appeared to be dose dependent, with a more marked, and rapid decrease in FTR mRNA at 350 µM $FeCl_3$ as compared with 50 µM $FeCl_3$. Consistent with these results, FTR expression was undetectable when mycelia were grown in the iron-rich medium, PDB. These results demonstrate that FTR is induced in iron-depleted environments, suppressed in iron-rich environments, and that its transcription is tightly regulated by the amount of iron in the medium (FIG. 5). This tight transcriptional regulation has been reported in yeast and is likely due to the sensitivity of transcriptional activation to changes in intracellular iron concentration. Such tight regulation likely allows the organism to avoid toxicity caused by excess iron. Of note, these results also demonstrate that FTR is likely to be expressed in vivo (see below) even in a host that has elevated available serum iron because free iron concentration in these hosts is still expected to be several orders of magnitude less than the highest concentration shown to induce expression of FTR (i.e. 50 µM). For example, we found that DKA mice have 7.29 µM available iron in their serum (see below). Additionally, Artis et al. demonstrated that sera collected from subjects in DKA contain 12.4 µM available iron (Artis et al., *Diabetes* 31(12):1109-14 (1982)).

Example 3

Expression of FTR in S. cerevisiae ftr1 Null Mutant

This Example shows that expression of R. oryzae FTR in S. cerevisiae ftr1 null mutant restores S. cerevisiae's ability to grow in iron-depleted environment.

Figure 6:
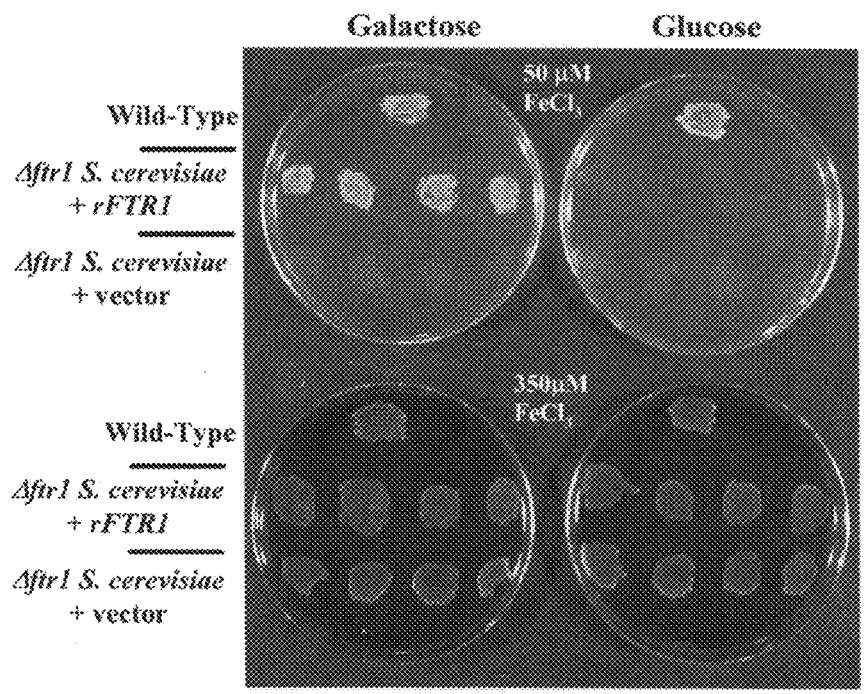
FIG. 6 shows the growth of *S. cerevisiae* ftr1 mutant transformed with vector expressing FTR.
Figure 8:
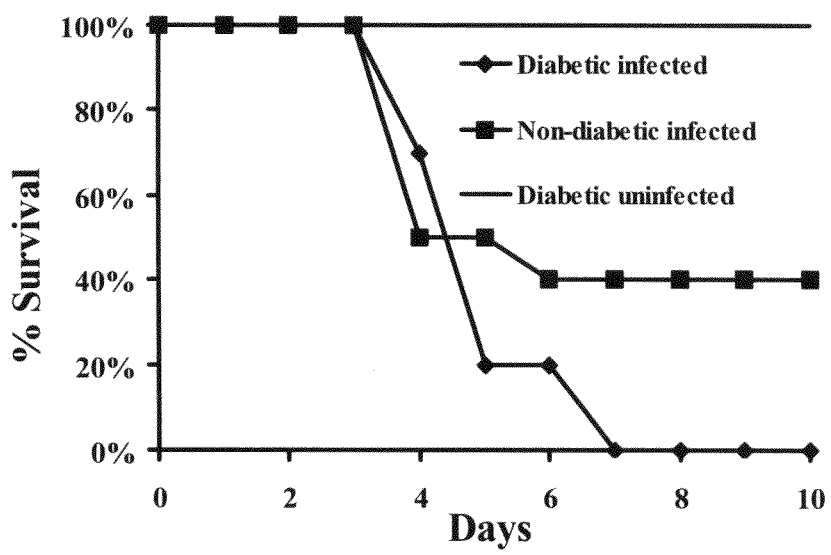
FIG. 8 shows the percent survival of diabetic mice (n=10) infected with *R. oryzae* as compared with non-diabetic infected and diabetic uninfected mice.

To determine whether FTR is functionally equivalent to S. cerevisiae FTR, we tested whether FTR could rescue the iron-dependent growth defect of a S. cerevisiae ftr1 null mutant. S. cerevisiae was transformed with a plasmid containing FTR under the control of the inducible GAL1 promoter (i.e. expression only in the presence of galactose). S. cerevisiae transformed with FTR grew when cultured on iron-limited medium (50 µM iron) containing galactose. In contrast, no growth was noted when the FTR-transformed cells were cultured on plates containing glucose, which failed to induce activation of the GAL1 promoter, and hence transcription of the FTR (FIG. 6). As expected, S. cerevisiae transformants carrying vector alone (negative control) did not grow on iron-depleted medium even in the presence of galactose. All S. cerevisiae transformants grew equally well on iron-rich plates (350 µM iron) containing either glucose or galactose, likely due to the presence of the low-affinity iron permease of S. cerevisiae, which is believed to function in iron-rich environments (FIG. 8).

Example 4

FTR Complements S. cerevisiae ftr1 Null Mutant Uptake of Iron

This example shows that R. oryzae FTR encodes a functional polypeptide in S. cerevisiae.

Figure 7:
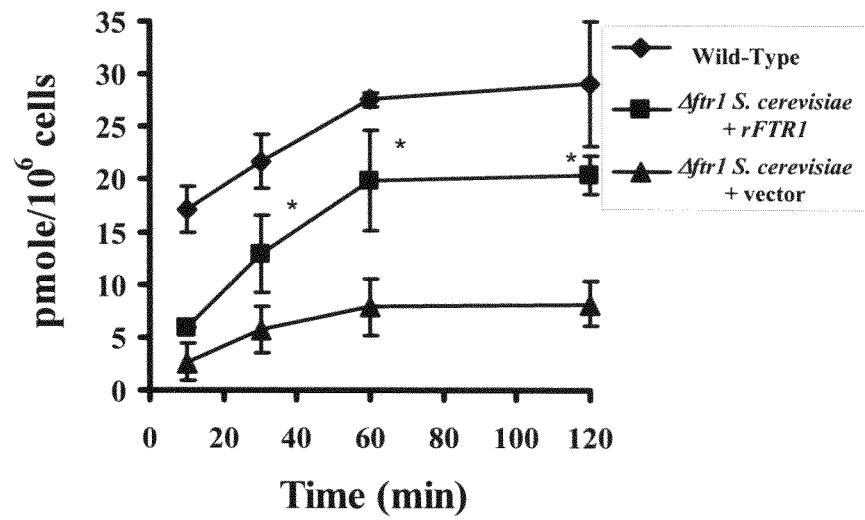
FIG. 7 shows high affinity iron uptake by *S. cerevisiae* ftr1 mutant transformed with vector expressing FTR as compared with iron uptake by wild-type *S. cerevisiae* and *S. cerevisiae* ftr1 mutant transformed with empty vector. *P<0.05.

To confirm that FTR-mediated growth rescue of the S. cerevisiae ftr1 mutant was due to increased iron uptake, we compared the kinetics of $^{59}Fe$ uptake of S. cerevisiae transformed with R. oryzae FTR under the GAL1 promoter to transformants containing the empty vector. The ftr1 null mutant cells transformed with the empty vector showed no intracellular iron accumulation when $^{59}FeCl_3$ was supplied at 0.1 µM (a concentration in which only high affinity iron permeases are active). In contrast, introduction of FTR into S. cerevisiae ftr1 null mutant restored the iron uptake to between 48-60% of the amount exhibited by the wild-type strain (FIG. 7).

In summary, in Examples 3 and 4 we showed that we have cloned a gene (FTR) that is expressed in R. oryzae in iron-depleted media, suppressed in iron-rich media, and complements the growth defect of high-affinity iron permease null mutant of S. cerevisiae by rescuing the mutant's ability to take up iron in iron-poor media. In aggregate, these data strongly indicate that FTR polypeptide encodes a high-affinity R. oryzae iron permease and also justifies the production of FTR polypeptide in S. cerevisiae because R. oryzae genes can be functionally expressed in S. cerevisiae.

Example 5

Development of Animal Model of Mucormycosis

To study the pathogenesis of any disease, it is essential to develop an animal model that recapitulates relevant clinical factors. This Example shows that we have developed an animal model relevant to mucormycosis, a DKA mouse model of hematogenously disseminated R. oryzae infection.

We successfully developed a DKA mouse model of hematogenously disseminated mucormycosis by using a single injection of streptozotocin given intraperitoneally. We chose this model because subjects with DKA are at high risk of developing mucormycosis. As expected, we found that mice with DKA are more susceptible to R. oryzae infection than normal mice. Seven days after intravenous challenge of $10^4$ spores, all mice with DKA died, whereas 40% of infected non-diabetic mice survived (FIG. 8).

Figure 9:
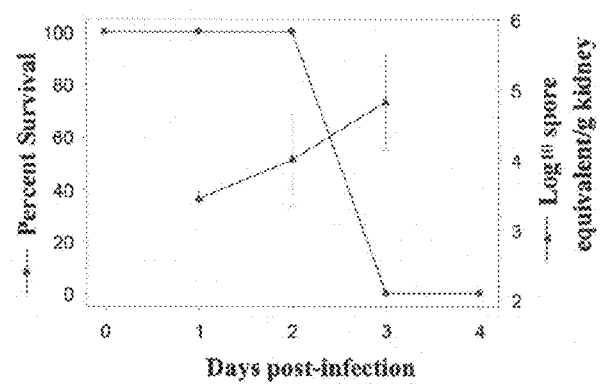
FIG. 9 shows a temporal link or an inverse correlation between percent survival and the kidney burden of *R. oryzae* ($5 \times 10^4$ spores) as determined by TAQMAN assay.

To assess the severity of infection, we compared tissue colony counts to a quantitative PCR-based (qPCR) (TAQ- MAN) assay that was developed originally to determine disease progression in animal models of *A. fumigatus*. The TAQMAN technique was developed because the colony count method is unreliable for determining tissue fungal burden of molds since hyphal structures are disrupted by tissue homogenization, resulting in death of the fungus and inaccurately low estimate of the organ fungal burden. Indeed, as anticipated, colony counts did not increase during infection with *R. oryzae* and did not correlate with mortality. In contrast, a temporal correlation between increase in tissue fungal burden and onset of mortality was found when a qPCR-based (TAQMAN) technique, using primers designed to amplify *R. oryzae* 18s rDNA, was used to quantify tissue *R. oryzae* burden (FIG. 9). These results were consistent with our preliminary results, in which mouse tissues spiked with varying inocula of *R. oryzae* showed a linear range of detection. Therefore, this qPCR-assay is a sensitive and reliable method for assessing the progression of mucormycosis in the DKA mouse model. This assay will be utilized to elucidate the role of iron metabolism in the pathogenesis of the disease.

Example 6

The Effects of Serum Iron Availability on Susceptibility of DKA Mice to *R. oryzae*

This Example shows that susceptibility of DKA mice to *R. oryzae* is due in part to elevated available serum iron.

To confirm that available iron renders diabetic mice more susceptible to *R. oryzae* infection, we compared levels of serum iron in DKA mice to those of normal mice by using the method of Artis et al. (1982, supra). In concordance with the results found in humans DKA mice (n=11) had approximately 5 fold higher levels of available serum iron than normal mice [median ($75^{th}$ quartile, $25^{th}$ quartile)]=7.29 (11.8, 4.3) µM vs. 1.69 (2.3, 1.3) µM, p=0.03 by Wilcoxon Rank Sum). These data underscore the clinical relevance of our DKA mouse model.

Figure 10:
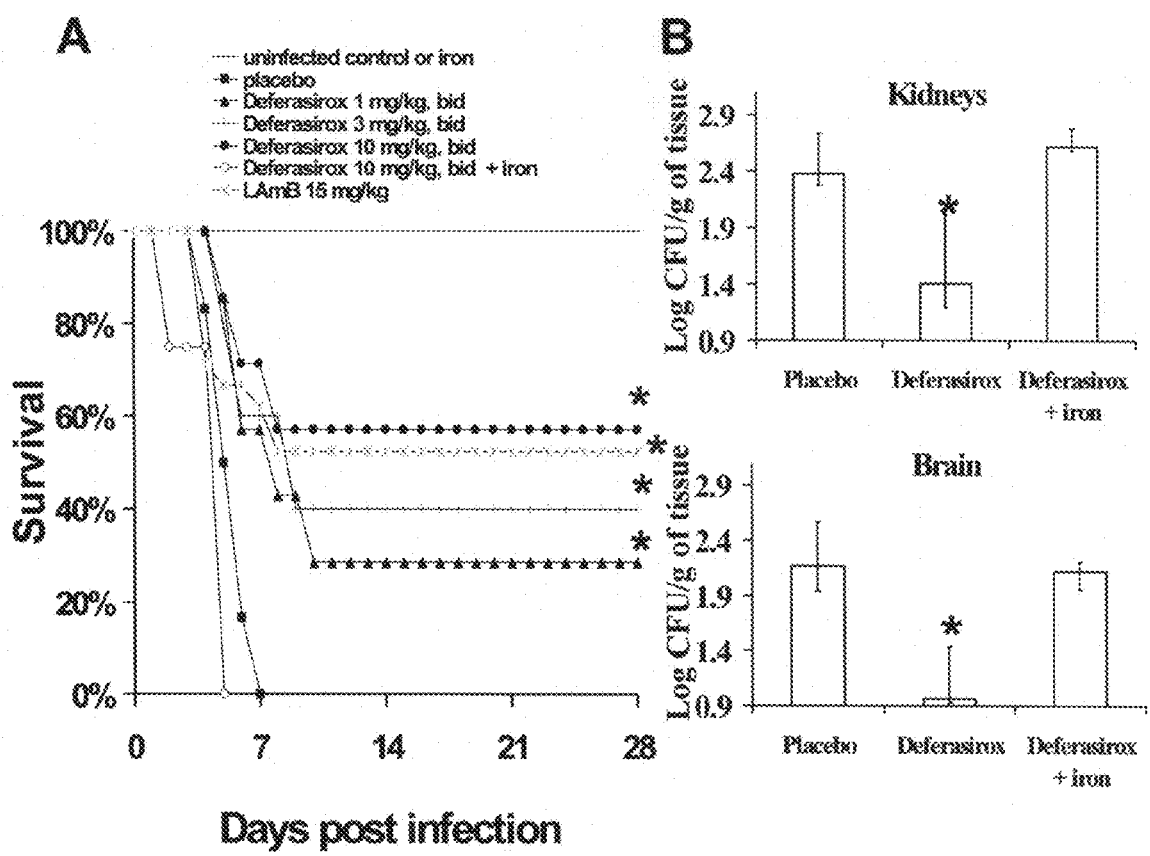
FIG. 10, panels A and B, show the percent survival of DKA mice (n=20) (FIG. 10A) and tissue fungal burden (n=11) (FIG. 10B) infected with $5 \times 10^3$ *R. oryzae* spores and treated with: 1) deferasirox (given orally); 2) deferasirox+saturating $FeCl_3$ (given i.p,); 3) intravenous LAmB for 4 days; and 4) placebo. Uninfected DKA mice and uninfected treated with $FeCl_3$ were included as negative controls. *p<0.05 vs. placebo or deferasirox+iron.

To confirm the role of elevated available serum iron in the pathogenicity of *R. oryzae* we investigated the effect of iron chelation on the susceptibility of DKA mice to *R. oryzae* infection. Mice were infected via the tail-vein with spores of *R. oryzae*. The mice were treated by oral gavage with 1, 3, or 10 mg/kg deferasirox (a newly FDA approved iron chelator to treat subjects with iron overload) in 0.5% hydroxypropylcellulose twice daily (bid) for seven days starting the day after infection. Negative control mice were treated with hydroxypropylcellulose carrier (placebo) or deferasirox plus saturating ferric chloride (administered i.p.). An additional negative control consisted of uninfected mice treated with ferric chloride. Deferasirox given at all doses significantly improved survival compared to controls (FIG. 10A). This improved survival paralleled the survival we get in this model when a high dose of liposomal amphotericin B (LAmB) is used to treat infection. To determine the impact of deferasirox on tissue fungal burden, DKA mice were infected i.v. as above. Mice were treated with deferasirox (10 mg/kg bid), deferasirox plus saturating ferric chloride, or placebo. Treatment was begun 16 h after infection and administered daily for 3 days. Kidneys and brains were removed on day four, homogenized, and quantitatively cultured. Deferasirox resulted in a greater than 10-fold decrease in both brain and kidney (primary target organs) fungal burden compared to mice treated with placebo or deferasirox plus saturating ferric chloride (FIG. 10B). By histopathology, kidneys of deferasirox-treated mice had no visible hyphae, whereas kidneys of mice treated with placebo or deferasirox plus saturating ferric chloride had extensively filamented fungi. Furthermore, mice treated with saturating iron had a striking absence of neutrophil influx to the sites of infection, while neutrophil influx was prominent in the kidneys of mice treated with deferasirox (data not shown). The reversal of protection when deferasirox was administered to mice with a saturating dose of $FeCl_3$ further proved that the mechanism of protection was due to iron chelation. Of note, these results are in agreement with our previous work showing that deferiprone (another chelating agent that is not used as a siderophore by *Rhizopus*) protected animals from *Rhizopus* infection and confirm the link between iron availability and *R. oryzae*. These results further confirmed the unique importance of iron in the pathogenesis of mucormycosis.

Example 7

Expression of FTR In Vivo in DKA Mice

This Example shows that *R. oryzae*'s FTR is expressed in vivo in DKA mice.

Figure 11:
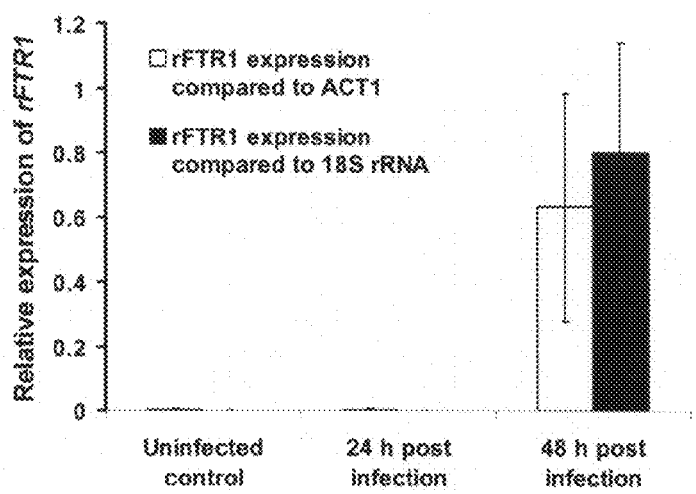
FIG. 11 shows the expression of FTR in the hematogenously disseminated mucormycosis model using DKA mice. Mice were infected with $10^5$ spores of *R. oryzae* 99-880 through the tail vein. At indicated time points infected brains were removed and total RNA was then used for real-time-RT-PCR analysis (n=4 mice per time point). Brains from uninfected mice served as a negative control. Values are expressed as average±SD.
Figure 12:
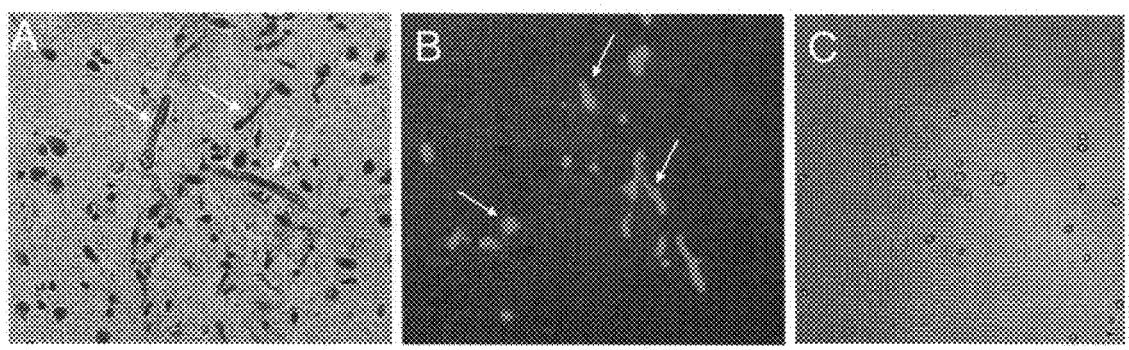
FIG. 12, panels A, B and C, show the expression of FTR in the brains of DKA mice infected with *R. oryzae* expressing GFP under the control of FTR promoter. Panel (A) H & E stain of brain infected with *R. oryzae*; Panel (B) brain section stained with rabbit polyclonal antibody to GFP then counter stained with FITC conjugated anti-rabbit antibody; and Panel (C) DIC confocal image showing non-fluorescent *R. oryzae* at the time of infection. Arrows denote fungal elements in infected brains. Magnification, ×400.

In order for FTR polypeptide to play a role in the pathogenesis of mucormycosis, it must be expressed during infection. We used a real time RT-PCR-based approach to investigate the expression of FTR polypeptide in the brains of diabetic ketoacidic (DKA) mice infected with $10^5$ spores of *R. oryzae* through tail vein injection. The brain was chosen because it is the primary target organ in this model. Mice were sacrificed 24 or 48 h post infection and brains were collected and immediately flash frozen in liquid nitrogen prior to grinding and RNA extraction with phenol. Brains collected from uninfected DKA mice were processed in parallel and served as negative controls. Following DNase treatment to eliminate contaminating genomic DNA, and reverse transcription (Ambion RETROscript® system), cDNA was analyzed by real-time PCR using the SYBR-Green method and an ABI® Prism 7000 cycler. Gene-expression was normalized to *R. oryzae* ACT1 or 18S rRNA-expression. FTR was found to have been expressed in the brains of 4 infected mice 48 h post infection but not after 24 h (FIG. 11). The lack of FTR expression after 24 h of infection cannot be attributed to the presence of lower fungal elements in the brains of infected mice since the expression of both 18S rRNA and ACT1 genes were detected in these tissues. The pattern of delayed FTR polypeptide expression (i.e. expression after 48 h but not 24 h of infection) can be explained by the fact that after 24 h fungal elements were not sufficiently iron-starved because spores had been grown on iron-rich medium during preparation of the inoculum. Forty eight hours following infection, as the fungal spores started to proliferate in the brain, *R. oryzae* started to express FTR polypeptide to scavenge iron from the host. As expected, brains from uninfected mice did not show any expression of FTR polypeptide.

These results clearly demonstrate that FTR polypeptide is expressed during infection and is involved in the pathogenesis of mucormycosis.

Figure 14:
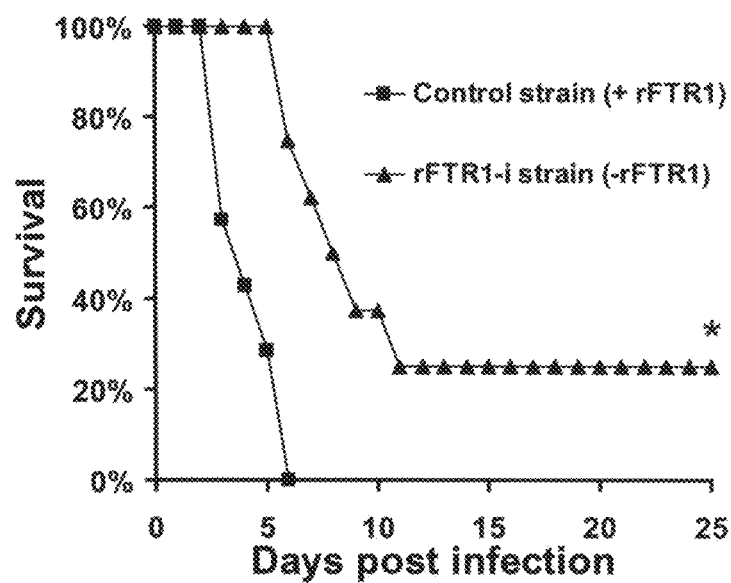
FIG. 14 shows the percent survival of DKA mice (n=8) infected i.v. with *R. oryzae* transformed with empty plasmid (control strain, $2.9 \times 10^3$ spores) or with RNAi plasmid targeting expression of FTR (FTR-i, $4.1 \times 10^3$ spores). *, P<0.001 by Log Rank test.

To confirm the expression of FTR in vivo during active infection, we used GFP as a reporter system for FTR expression. *R. oryzae* was transformed with a plasmid containing GFP cloned down stream of a 2 kb fragment containing FTR promoter. This strain fluoresced green when grown in iron-depleted but not in iron-rich environments in vitro (data not shown). DKA mice were infected with $1 \times 10^5$ spores of this *R. oryzae* strain grown under iron-rich conditions. Forty eight hours post infection mice were sacrificed and brains were collected, and fixed in 10% zinc formalin. Paraffin sections of the brains were stained with anti-GFP polyclonal rabbit Ab and counter stained with anti-rabbit FITC conjugated Ab. As shown in FIG. 14, fungal elements in the brains of mice infected with *R. oryzae* expressing GFP under the control of the FTRp fluoresced green, therefore confirming our earlier findings that FTR polypeptide is expressed during active infection an is involved in pathogenesis of the mucormycosis.

Example 8

FTR Polypeptide and its Homology to known Proteins

This Example shows that *R. oryzae* FTR polypeptide little or no homology with any known human proteins.

In order to minimize the potential for induction of autoimmune responses, it is desirable that a protein vaccine being utilized as a human vaccine not have significant homology to numerous human proteins. To investigate the potential for homology between the FTR polypeptide and human proteins, a PubMed BLAST search was performed comparing the amino acids 16-368 of the FTR polypeptide (i.e. the amino acids in the intended FTR polypeptide vaccine) to the human proteome. The search identified five open reading frames with extremely limited homology with an alignment score of 30.4, e=9.0 for all of the five proteins. Three of these proteins are coiled-coil domain containing 82 (i.e., EAW66982; AAH33726.1; and NP_079001.2), one is a CCDC82 protein (i.e., AAH18663.1) and an unnamed protein (i.e., BAB 15683.1). As a benchmark, the standard BLAST search e-value for identification of unique sequences from fungi compared to other organisms has been set at $10^{-8}$, indicating that *R. oryzae* FTR has no significant homology to the human proteome.

Example 9

The Role of FTR Gene Product in Virulence of *R. oryzae* in the DKA Mouse Model of Hematogenous Dissemination or Mucormycosis This Example shows that FTR gene product (e.g., mRNA or polypeptide) is required for full virulence of *R. oryzae* in the DKA mouse model mucormycosis.

Figure 13:
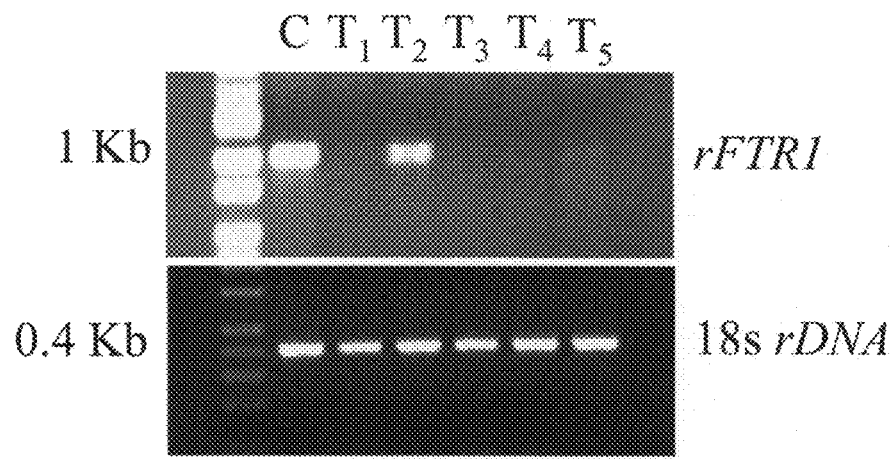
FIG. 13 shows the agarose gel electrophoresis result of an RT-PCR assay showing lack of expression of FTR in *R. oryzae* transformed with RNA-interference plasmid ($T_1$ and $T_3$-$T_5$) as compared to *R. oryzae* transformed with empty plasmid (C). Primers amplifying the 18s rDNA served as a control to demonstrate the specificity of RNA interference in targeting FTR.

We have utilized RNA interference (RNAi) technology to inhibit the expression of FTR in *R. oryzae*. A 400 bp fragment of FTR ORF containing the REGLE (SEQ ID NO: 3) motif (believed to interact with iron during uptake) was cloned in plasmid pRNAi-pdc upstream of an intron segment. The reverse complement sequence of the same fragment was cloned downstream of the intron. The generated plasmid was transformed into *R. oryzae* pyrf mutant using the Biolistic® delivery system (BioRad®) and transformants were selected on minimal medium lacking uracil. Southern blot analysis showed that all obtained transformants maintained the transformed plasmid episomally (data not shown). RT-PCR was used to compare expression of FTR by five selected transformants to a control strain, which was transformed with the empty plasmid. FTR expression was almost completely inhibited in 4 of the 5 transformants tested and reduced in one transformant compared to control strain (FIG. 13). The expression of 18s rDNA was not altered in any transformant indicating the specificity of RNAi in inhibiting expression of FTR.

The virulence of one of the RNAi transformants was compared to the control strain in the DKA mouse model of hematogenously disseminated mucormycosis. Mice were infected with the control strain transformed or with a transformant harboring the RNAi plasmid (FTR-i strain). There was delayed and reduced virulence of the RNAi-transformant compared to the control strain. Interestingly, we found that *R. oryzae* recovered from brains and kidneys of moribund mice infected with the FTR-i strain lost the RNAi plasmid since *R. oryzae* failed to grow on minimal medium without uracil but did grow on rich medium (potato dextrose agar). In contrast, *R. oryzae* recovered from the two mice that survived the infection for 25 days (with no signs of disease) was able to grow on both minimal medium without uracil and on rich medium, indicating that the RNAi plasmid was still present in these spores and that inhibiting of FTR expression during infection inhibits virulence of *R. oryzae* (FIG. 14).

These data demonstrate that the FTR is a pivotal virulence factor for *R. oryzae* in the DKA mouse model, and provide additional rational in support of development of an FTR vaccine to prevent mucormycosis infections.

Example 10

Figure 19:
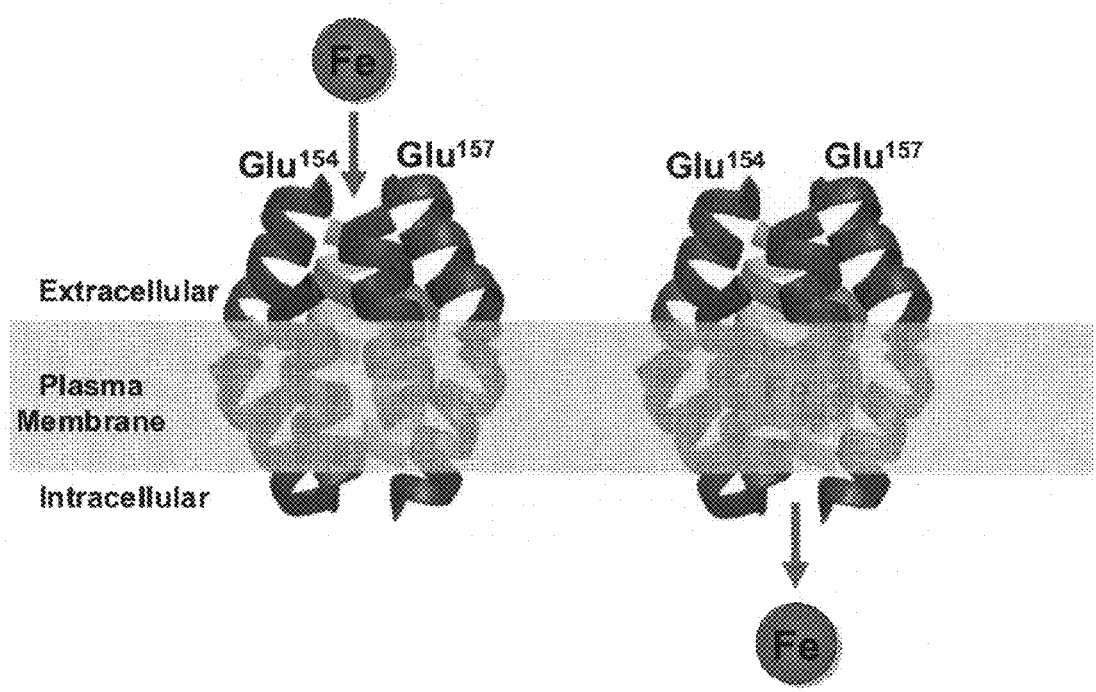
FIG. 19 shows a conceptual model of the *Rhizopus* rFtr1p helical bundle protein and translocation of iron from the extracellular setting into the cytoplasm of *Rhizopus* species.

The rFtr1p is Exposed Extracellularly and has Limited Homology to Known Human Proteins but is Conserved Among Other Mucorales Homology modeling predicts rFtr1p to have a poly-helical bundle structure which is the hallmark of ion-binding or transport proteins found in other microorganisms. In the most robust models, the crucial Glu154 and Glu157 residues of the REGLE (SEQ ID NO: 3) iron-binding motif are exposed upon the extracellular facet of the protein, making them accessible to potential binding and inhibition by antibodies (FIG. 19).

In order to minimize the potential for induction of autoimmune responses, it is desirable that a protein vaccine being utilized as a human vaccine not have significant homology to numerous human proteins. To investigate the potential for homology between the rFtr1p and human proteins, a PubMed BLAST search was performed comparing the amino acids 16-368 of the rFtr1p (i.e. the amino acids in the intended rFtr1p vaccine) to the human proteome. The search identified five open reading frames with extremely limited homology with an alignment score of 30.4, e=9.0 for all of the five proteins. Three of these proteins are coiled-coil domain containing 82 (i.e. EAW66982; AAH33726.1; and NP_079001.2), one is a CCDC82 protein (i.e. AAH18663.1) and an unnamed protein (i.e. BAB15683.1). As a benchmark, the standard BLAST search e value for identification of unique sequences from fungi compared to other organisms has been set at $10^{-8}$, (Jones et al., *Proc Natl Acad Sci USA* 2004; 101:7329-34 (2004)) indicating that rFtr1p has no significant homology to the human proteome. By comparison, a PubMed BLAST search of the Hepatitis B Surface Antigen, which is utilized as an extremely safe vaccine in humans against the Hepatitis B Virus, revealed 18 hits, one of which was significant (score 75.9, e=$3 \times 10^{-14}$), with the remainder ranging from scores of 27 to 29, with e values of 5 to 10. Hence, the proposed rFtr1p vaccine has comparable or less homology to the human proteome as does the widely utilized HBSAg vaccine.

In contrast, a recent publication demonstrated that rFTR1 is highly conserved among other pathogenic Mucorales including *R. microsporus, R. niveus, R. stolonifer, Rhizomucor miehei, Rhizomucor pusillus, Mucor circinelloides, M. racemosus, M rouxii,* and *M. plumbeus,* with nucleotide homology of >70%. Interestingly, the putative REGLE (SEQ ID NO: 3) iron-binding functional motif is 100% conserved among all Mucorales. Nyilasi et al., Clin Microbiol Infect.

(2008). This indicates that the proposed vaccine will be cross-immunogenic against other agents of mucormycosis. Moreover, it is expected that cross-genera protection will occur because R. oryzae rFtr1p has a high degree of identity with high iron permeases from a very diverse array of fungi, even beyond molds, including Aspergillus spp., C. albicans, and Cryptococcus neoformans. In all of these fungi, the core REGLE (SEQ ID NO: 3) iron-binding functional motif is 100% conserved.

Example 11

Figure 20:
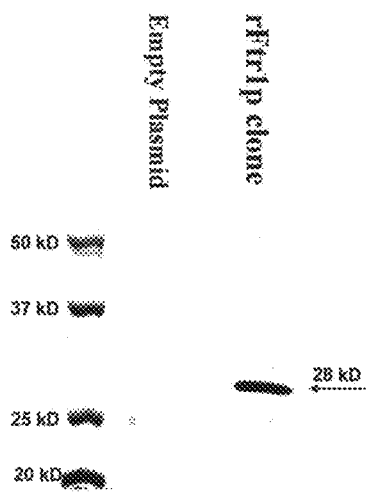
FIG. 20 shows results of an SDS-PAGE demonstrating purified synthetic/recombinant rFtr1p. *E. coli* was transformed with a plasmid expressing 6X-His tagged synthetic rFTR1 or with empty plasmid. rFtr1p was purified by Ni-agrose column and detected at the expected size of 28 kD in the rFtr1p clone but not when *E. coli* was transformed with empty plasmid.

Passive Immunization with Sera Collected from Mice Vaccinated with rFtr1p Protects Mice from R. oryzae Infection To maximize protein production a gene was synthesized (Genscript) encoding a more hydrophilic protein by removing the signal peptide and 6 transmembrane domains that direct localization of the protein to the cell membrane. While the synthesized gene had sequence elements removed, none of the remaining sequence was altered, so as to avoid altering potential epitopes in the exposed, hydrophilic regions of the protein. The synthetic gene also included a 6X-His-tag (SEQ ID NO:4) to affinity purify the expressed protein. This gene was cloned into pQE32 expression vector and transformed into E. coli. Log phase bacterial cells were induced with IPTG and the cells were harvested and the recombinant protein was purified over a Ni-agrose affinity column according to the manufacturer instructions (Qiagen) with a production of ~1-1.3 mg of purified protein per liter of culture (FIG. 20). The generated protein was used to raise murine antibodies as described below.

Figure 21:
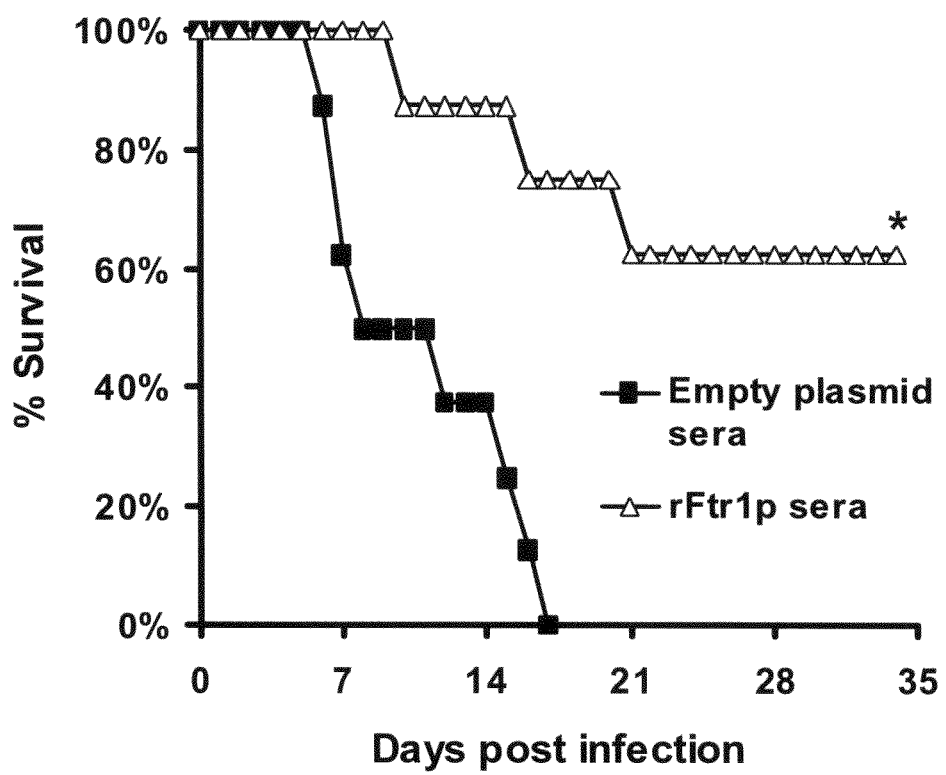
FIG. 21 shows survival of DKA mice (n=8) infected with *R. oryzae* ($2.5 \times 10^7$ spores) and treated with serum collected from mice immunized with either rFtr1p or empty plasmid.*, P<0.007 by Log Rank test.

To generate immune serum for passive immunization, Balb/c mice were immunized by SQ injection of rFtr1p (20 µg) mixed with complete Freund's adjuvant (CFA) at day 0, boosted with another dose of the antigen with incomplete Freund's adjuvant (IFA) at day 21, and bled for serum collection two weeks later. Pooled sera collected from vaccinated mice demonstrated Ab titer against rFtr1p of >1:800,000, whereas pooled sera collected from mice vaccinated with empty plasmid had an Ab titer of 1:200. Immune or control sera (0.25 ml) were administered i.p. to DKA recipient mice 2 h before intranasal infection with R. oryzae. Sera doses were repeated 3 days post infection. Infected mice treated with immune serum improved survival compared to mice treated with control serum (FIG. 21). These studies clearly demonstrate the feasibility of using passive immunization targeting rFtr1p to improve survival during mucormycosis.

Example 12

FTR1 is Expressed by R. oryzae during Infection in DKA Mice

For FTR1 to play a role in the pathogenesis of mucormycosis, it must be expressed during infection. Quantitative real time PCR (qPCR) was used to investigate the expression of FTR1 in the brains of DKA mice infected intravenously with $10^5$ spores of R. oryzae, an inoculum that causes a 100% mortality within 2-3 days (Ibrahim et al., Antimicrob Agents Chemother 49: 721-727 (2005). The brain was chosen for analysis because it is a primary target organ in this model (Ibrahim et al., Antimicrob Agents Chemother 49: 721-727 (2005)). Expression of FTR1 from mice (n=5) sacrificed 24 h post infection increased by 4 fold [median ($25^{th}$ quartile, $75^{th}$ quartile)=4.12 (1.03, 0.27), p=0.03 by Wilcoxon Rank Sum)] relative to the constitutive ACT1 gene. As expected, brains from uninfected mice did not show any expression of FTR1.

The non-parametric log-rank test was used to determine differences in survival times, whereas differences in kidney fungal burden, iron uptake, growth rate and in vivo FTR1 expression were compared by the non-parametric Wilcoxon Rank Sum test.

To directly visualize expression of FTR1 in vivo during infection, R. oryzae was transformed with a plasmid containing GFP under the control of the FTR1 promoter. R. oryzae strains used in this study are listed in Table 1. Briefly, organisms were grown on potato dextrose agar (PDA) or on YPD plates [1% yeast extract (Difco Laboratories), 2% bacto-peptone (Difco), and 2% D-glucose] for 4 days at 37° C. For R. oryzae M16 (a pyrF null mutant that is unable to synthesize its own uracil), PDA was supplemented with 100 µg/ml uracil. An 815 bp partial pyrF PCR fragment (pyrF P11/P13) was used to restore R. oryzae M16 to prototrophy. This fragment overlaps the pyrF mutation present in M16 (i.e. point mutation at nt+205 of G to A) (Skory and Ibrahim, Curr Genet. 52: 23-33 (2007)) and is capable of restoring functionality through gene replacement. In some experiments, R. oryzae was starved for iron by growth on yeast nitrogen base (YNB) (Difco/Becton Dickinson, Sparks, Md.) supplemented with complete supplemental media without uracil (CSM−URA) (Q-Biogene), (YNB+CSM−URA) [formulation/100 ml, 1.7 g YNB without amino acids, 20 g glucose, 0.77 g CSM-URA] in the presence of 1 mM of ascorbic acid and ferrozine. The sporangiospores were collected in endotoxin free PBS containing 0.01% TWEEN 80, washed with PBS, and counted with a hemacytometer to prepare the final inocula.

TABLE 1

Strains used in this study

| Strain | Genotype | Description and Source |
|---|---|---|
| R. oryzae 99-880 | Wild-type | Clinical isolate (Ibrahim et al., J Clin Invest 117: 2649-2657 (2007)). |
| R. oryzae M16 | pyrF205 | Uracil deficient (Skory and Ibrahim, Curr Genet 52: 23-33 (2007)). |
| R. oryzae PyrF complemented | pyrF205::PyrF | M16 complemented with a wild-type copy of PyrF at its original locus, this work |
| R. oryzae GFP1 | M16 (pP$_{Ftr-1}$-GFP) | M16 transformed with a plasmid containing a FTR1 promoter driven GFP (Ibrahim et al., J Clin Invest 117: 2649-2657 (2007)). |
| R. oryzae FTR1Ko | pyrF205, ftr1::PyrF | ftr1 knock out, this work |

TABLE 1-continued

Strains used in this study

| Strain | Genotype | Description and Source |
|---|---|---|
| R. oryzae FTR1Inh | M16 (pFTRi-pdc intron) | FTR1 inhibited by RNAi, this work |
| R. oryzae Empty | M16 (pRNAi-pdc intron) | M16 transformed with empty plasmid, this work |

Figure 22A:
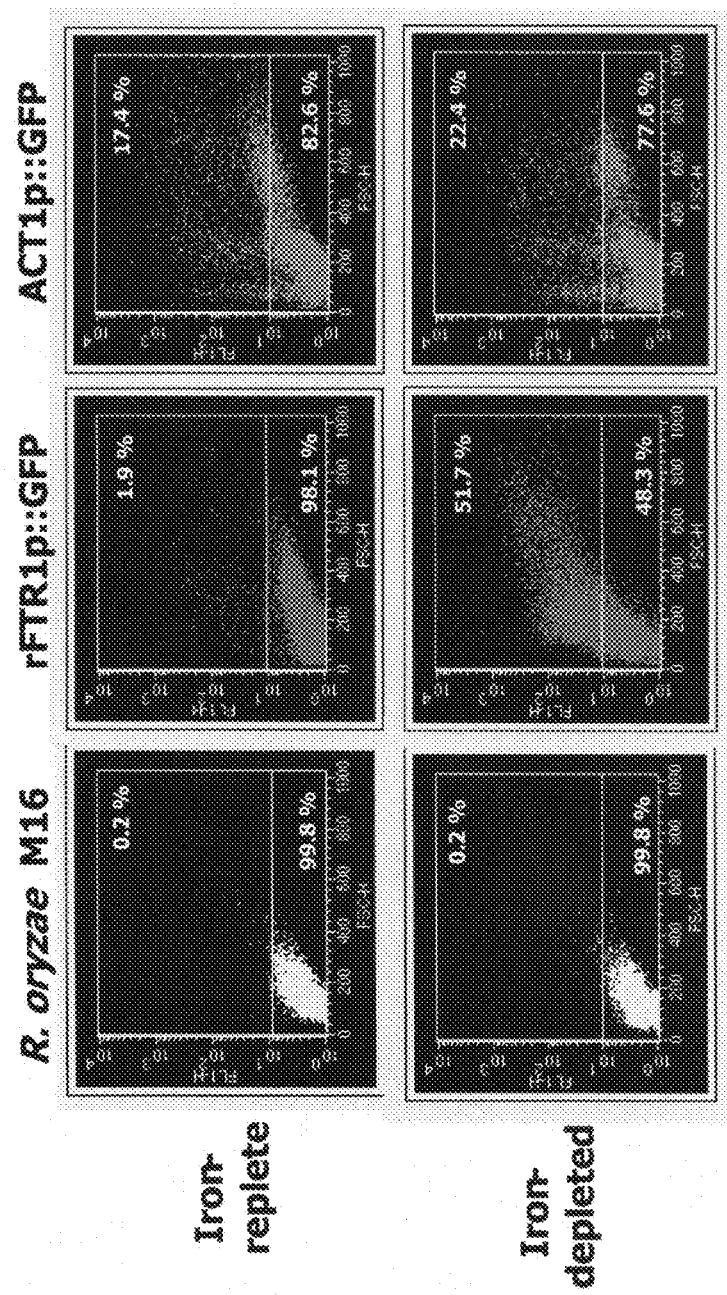
FIG. 22, panels A and B, show that FTR1 is expressed in DKA mice infected intravenously with *R. oryzae*. Panel (A) shows FACS analysis of *R. oryzae* transformed with plasmid containing the reporter gene GFP driven by either the FTR1 promoter or the constitutively expressed ACT1 promoter and grown in iron-rich or iron-depleted conditions. *R. oryzae* M16 transformed with an empty plasmid was used as a negative control. Panel (B) shows FTR1 is expressed in the brains of DKA mice infected with *R. oryzae* expressing GFP under the control of FTR1p. For anti-GFP Ab stain, tissue section was stained with rabbit polyclonal antibody to GFP then counter stained with FITC conjugated anti-rabbit antibody. For DIC, confocal image showing non-fluorescent *R. oryzae* at the time of infection. Arrows denote fungal elements in infected brains. Magnification, ×400.

This strain fluoresced green when grown in iron-depleted but not iron-rich media in vitro, whereas R. oryzae transformed with GFP under the control of the constitutive actin promoter (positive control) fluoresced regardless of the iron concentration in the medium (FIG. 22A). DKA mice were infected with the GFP reporter strain or PyrF-complemented R. oryzae grown under iron-rich conditions to suppress GFP expression prior to infection. Twenty four or 48 h post infection brains were collected and processed for histopathology. Because the paraffin embedding process abrogated the intrinsic fluorescence of the GFP protein, the sections were stained with fluorescent anti-GFP antibody. Samples taken 24 h post infection did not show any fungal elements, which was expected since 48 h post infection is the earliest time point that fungal elements can be detected histopathologically in infected tissues (Ibrahim et al., *Antimicrob Agents Chemother* 49: 721-727 (2005)). At 48 h of infection in the brain, the FTR1 reporter strain of R. oryzae expressed GFP, whereas the negative control, PyrF-complemented R. oryzae did not (FIG. 22B). Additionally, GFP expression was induced by low iron levels in the host environment since spores used for infecting mice were grown in iron-rich medium (condition that suppresses the expression of FTR1) and did not fluoresce green when used to infect mice (FIG. 22B, DIC overlaid with fluorescence).

Example 13

Figure 23B:
FIG. 23, panels A, B, C and D, show that the disruption cassette integrates in FTR1 locus but complete elimination of FTR1 could not be achieved. Panel (A) A diagram summarizing the strategy we used to achieve FTR1 disruption. PyrF (998 bp) was used as a selectable marker flanked by 606 and 710 bp fragments of FTR1-5' UTR and FTR1-3' UTR, respectively. Panel (B) Gel electrophoresis showing integration of the disruption cassette in a representative putative ftr1 null mutant (KO) but not in the wild-type (WT) (see 5'UTR and 3'UTR). Primers FTR1 P11 and FTR1P12 were used to amplify 503 bp from the FTR1 ORF only from the wild-type but not from the putative ftr1 null mutant (see FTR1). Primers PyrF P9 and PyrF P18 to test for possible reciculization of the transformed plasmid with expected band of 2094 bp were also used (see self ligation). Panel (C) Comparison of growth rate of *R. oryzae* wild-type, *R. oryzae* PyrF-complemented, or putative ftr1 null mutants grown on different sources of iron on iron-limited or iron-rich media. Growth was measured after 48 h for media containing 10 or 1000 μM (iron-rich) of FeCl3 or FeSO4 or 100 μM of ferrioxamine, while growth was measured after 72 h for medium supplemented with 100 μM heme. Values are expressed as increase in mycelial diameter growth on solid growth medium in cm/h. * $P<0.05$ compared to wild-type or *R. oryzae* PyrF-complemented strains. Panel (D) Gel electrophoresis showing lack of amplification of FTR1 after one round of purification of the putative null mutants on iron-rich medium (1000 μM FeCl3) and amplification of the FTR1 from the same isolate following growth on iron-depleted medium (i.e. 100 μM ferrioxamine) for 96 h. Amplification of actin (600 bp) was used to control for DNA loading.

Isolation of a Homokarvotic ftr1 Null could not be Achieved in Multinucleated R. oryzae Despite Integration of the Disruption Cassette at the FTR1 Locus The expression of FTR1 during active infection suggested a role for FTR1 in the pathogenicity of R. oryzae. The effect of FTR1 gene disruption on the ability of R. oryzae to take up iron in vitro and cause disease in vivo was studied. Isolates obtained from two separate transformations were purified with one round of sporulation and single colony isolation. To achieve single colony isolation, transformants were grown on chemically defined medium (YNB+CSM−URA) supplemented with 1 mM $FeCl_3$ (iron rich) to favor the segregation of the ftr1 null allele, since FTR1 is poorly expressed in concentrations ≧350 µM of $FeCl_3$ (Fu et al., *FEMS Microbiol Lett* 235: 169-176 (2004)). Isolates were screened for integration of the disruption cassette with PCR primer pairs FTR1-P3/PyrF-P9 (expected 1054 bp) and PyrF-P18/FTR1-P4 (expected 1140 bp). Disruption of the FTR1 locus was tested by the absence of a PCR amplification product using primers FTR1-P5/FTR1-P6 (expected 503), which amplified a segment from the ORF of FTR1 (Table 2 and FIG. 23A). PCR confirmed integration of the disruption cassette in the FTR1 locus, and absence of FTR1 ORF from several putative null mutant strains (FIG. 23B). Furthermore, these amplification products were also sequenced to demonstrate that the disruption cassette had integrated into the FTR1 locus by homologous recombination (data not shown). Finally, integration of the disruption cassette in the FTR1 locus was confirmed by Southern blotting (see below).

To study the expression of FTR1, we utilized GFP as a reporter system for FTR1 promoter expression. R. oryzae M16 was transformed with a plasmid containing the reporter gene GFP driven by the FTR1 promoter (R. oryzae GFP1) as previously described (Ibrahim et al., *J Clin Invest* 117: 2649-2657 (2007)). GFP was also cloned under the constitutively expressed actin promoter (Act1p) then transformed into R. oryzae M16 to serve as a positive control. Prior to studying the expression of FTR1 in vivo we examined the expression of FTR1 in vitro using FACS analysis. Briefly, R. oryzae transformed with either GFP driven by Ftr1p or Act1p were grown in YNB+CSM−URA with (iron-depleted conditions) or without (iron-replete conditions) 1 mM of ascorbic acid and ferrozine at 37° C. for 12 h. These conditions produced germlings of R. oryzae rather than hyphae. Fluorescence of 1 ml of germlings was determined using a FACSCaliber (Becton Dickinson) instrument equipped with an argon laser emitting at 488 nm. Fluorescence emission was read with 515/40 bandpass filter. Fluorescence data were collected with logarithmic amplifiers. The mean fluorescence intensities of 104 events were calculated using CELLQUEST software.

For in vivo infection, BALB/c male mice (>20 g) were rendered diabetic with a single i.p. injection of 190 mg/kg streptozotocin in 0.2 ml citrate buffer 10 days prior to fungal challenge (Ibrahim et al. *Antimicrob Agents Chemother* 47: 3343-3344 (2003)). Glycosuria and ketonuria were confirmed in all mice 7 days after streptozotocin treatment. Diabetic ketoacidotic mice were infected with fungal spores by tail vein injection with a target inoculum of 5×103 spores. To confirm the inoculum, dilutions were streaked on PDA plates containing 0.1% TRITON and colonies were counted following a 24 h incubation period at 37° C. For the intranasal infection, 107 spores in 20 µl of 0.01% TWEEN 80 in PBS were placed on the nostrils of ketamine (100 mg/kg) sedated mice ((Waldorf et al, *Journal of Clinical Investigation* 74: 150-160 (1984)). To confirm the inoculum, mice were sacrificed immediately after inhaling R. oryzae spores, and lungs were homogenized, plated on PDA containing 0.1% triton and colonies were counted following incubation at 37° C. For both models, the primary efficacy endpoint was time to death. In some experiments, as a secondary endpoint, brain and kidney fungal burden (primary target organs) (Ibrahim et al., *Antimicrob Agents Chemother* 49: 721-727 (2005)) was determined by homogenization by rolling a pipette on organs placed in Whirl-Pak bags (Nasco, Fort Atkinson, Wis.) containing 1 ml saline. The homogenate was serially diluted in 0.85% saline and then quantitatively cultured on PDA plates containing 0.1% triton. Values were expressed as log 10 cfu g-1 tissue. To detect GFP expression, anti-GFP rabbit polyclonal antibody (Novus) was used to stain the histopathological samples then counter stained with FITC conjugated anti-rabbit antibody.

To quantify the expression of FTR1 in infected tissues, brains of BALB/C mice infected with *R. oryzae* wild type (99-880) through tail vein injection were collected 24 or 48 hr post infection and immediately flash frozen in liquid nitrogen prior to grinding and RNA extraction with phenol. Brains collected from uninfected DKA mice were processed in parallel and served as negative controls. Frozen brains were then ground under liquid nitrogen and total RNA was then isolated using the hot phenol method (Gravelat et al. *Infect Immun* 76: 3632-3639 (2008)). Contaminating genomic DNA was removed from RNA samples by treatment with 1 µl of Turbo-DNase (Ambion) for 30 min at room temperature. DNase was then removed using an RNA Clean-Up kit (Zymo Research). First-strand cDNA synthesis was performed using the Retroscript first-strand synthesis kit (Ambion). FTR1 specific primers (listed in Table 2) were designed with the assistance of online primer design software (Genscript). The amplification efficiency was determined by serial dilution experiments, and the resulting efficiency coefficient was used for the quantification of the products (Pfaffl et al., *Nucleic Acids Res* 29: e45 (2001)).

Gene expression was analyzed by an ABI Prism 7000 Sequence Detection System (Applied Biosystems) using the QuantiTect Sybr Green PCR kit (Qiagen). PCR conditions were were 10 min at 90° C. and 40 cycles of 15 s at 95° C. and 1 min at 60° C. Single PCR products were confirmed with the heat dissociation protocol at the end of the PCR cycles. The amount of FTR1 expression in infected brains was normalized to either 18S rRNA or ACT1 (Table 2) and the quantified using the $2(-\Delta\Delta C(T))$ method (Livak and Schmittgen, (2001) Methods 25: 402-408 (2001)). All reactions were performed in duplicate, and the mixture included a negative no-reverse transcription (RT) control in which reverse transcriptase was omitted.

TABLE 2

Oligonucleotides used in this study.

| Primers | Sequence | Description |
|---|---|---|
| Primers used for detecting in vivo expression of FTR1 | | |
| FTR1-RT5' | GGTGGTGTCTCCTTGGGTAT (SEQ ID NO: 5) | 5' primer |
| FTR1-RT3' | AAGGAAACCGACCAAACAAC (SEQ ID NO: 6) | 3' primer |
| 18S-RT5' | CCAGACTGGCTTGTCTGTAATC (SEQ ID NO: 7) | 5' primer annealing to r-RNA |
| 18S-RT3' | AAGTCAAATTGTCGTTGGCA (SEQ ID NO: 8) | 3' primer annealing to r-RNA |
| ACT1-RT5' | TGAACAAGAAATGCAAACTGC (SEQ ID NO: 9) | 5' primer |
| ACT1-RT3' | CAGTAATGACTTGACCATCAGGA (SEQ ID NO: 10) | 3' primer |
| Primers used for making the ftr1 disruption cassette and confirming integration in the FTR1 locus | | |
| FTR1 P1 | TTCGAAAAGACCGTCAGGATTAGC (SEQ ID NO: 11) | Annealing to FTR1-5' UTR |
| FTR1 P2 | GAGGGACACAAGCAAGCAGAAAGT (SEQ ID NO: 12) | Annealing to FTR1-3' UTR |
| FTR1 P3 | CACTTACGGCCATTTTCCATTGAC (SEQ ID NO: 13) | Annealing to FTR1-5' UTR upstream of the disruption cassette |
| FTR1 P4 | CGCGCTAAATGAACAAAGAAT (SEQ ID NO: 14) | Annealing to FTR1-3' UTR downstream of the disruption cassette |
| FTR1 P5 | ATGTCTCAAGATCTCTTCAACCGTACC (SEQ ID NO: 15) | 5' primer testing for the entire FTR1 ORF (1100 bp) |
| FTR1 P6 | TTAAGCCTTAATAGCATCAGATTCG (SEQ ID NO: 16) | 3' primer testing for the entire FTR1 ORF (1100 bp) |
| FTR1 P11 | GATCACTGCCATGGGTCTTGCTAT (SEQ ID NO: 17) | 5' primer to test for 503 by of FTR1 ORF |
| FTR1 P12 | TATCATGTTGGCTTCTGGGTCTC (SEQ ID NO: 18) | 3' primer to test for 503 by of FTR1 ORF |

TABLE 2-continued

Oligonucleotides used in this study.

| Primers | Sequence | Description |
|---|---|---|
| PyrF P9 | GCCGTGGCGCAGACAAGAG (SEQ ID NO: 19) | 3' primer annealing to pyrF |
| PyrF P18 | GTGCCGAAATCGCTCCAGA (SEQ ID NO: 20) | 5' primer annealing to pyrF |
| ACT1 P1 | GTCTTTCCTTCTATTGTTGGTC (SEQ ID NO: 21) | 5' primer to test for functional template DNA (600 bp) |
| ACT1-P2 | CCATCAGGAAGTTCATAAGAC (SEQ ID NO: 22) | 3' primer to test for functional template DNA (600 bp) |

Primers used in making PyrF-complemented *R. oryzae*

| PyrF P11 | CAAAGCCAATTCAGCCTCAAATG (SEQ ID NO: 23) | 5' primer to amplify partial PyrF (815 bp) |
| PyrF P13 | CTTGGATCAGGGTGGACTCGTAG (SEQ ID NO: 24) | 3' primer to amplify partial PyrF (815 bp) |

Primers used to determine FTR1 copy number

| FTR1 P9 | CCAACAGTGAAAAGTCATCCTTT (SEQ ID NO: 25) | 5' primer to amplify FTR1 (250 bp) |
| FTR1 P10 | GCAATAGGAATTGATTTTCCTTG (SEQ ID NO: 26) | 3' primer to amplify FTR1 (250 bp) |
| ACT1 P3 | TATCGTTCTTGACTCTGGTGATG (SEQ ID NO: 27) | 5' primer to amplify actin (250 bp) |
| ACT1 P4 | GAAAGAGTGACCACGTTCAGC (SEQ ID NO: 28) | 3' primer to amplify actin (250 bp) |

Primers used for making RNAi strain

| PyrF14 | CTCGAGGCTTTAGGTCAAATTGTGG (SEQ ID NO: 29) | 5' primer to amplify 1641 bp of PyrF to clone in pRNAi-pdc |
| PyrF15 | CCCGGGTTATTGCTTGATACCATAT-TGTG (SEQ ID NO: 30) | 3' primer to amplify 1641 bp of PyrF to clone in pRNAi-pdc |
| FTR1 P7 | GCGGCCGCGCTAGCGCATGCAT-GTCTCA AGATCTCTTCAACGTACCGATC (SEQ ID NO: 31) | 5' primer to amplify 450 bp of FTR1 to clone in pRNAi-pdc |
| FTR1 P8 | GACGTCCCGCGGGGCGCGCCGGTGATAA AAGGCAAGACAAAGAACGCGTA (SEQ ID NO: 32) | 3' primer to amplify 450 bp of FTR1 to clone in pRNAi-pdc |
| 18S rRNA P1 | CATGGTTGAGATTGTAAGATAG (SEQ ID NO: 33) | 5' primer to amplify 18S rRNA |
| 18S rRNA P2 | AGTCAATGGACGTGGAGTC (SEQ ID NO: 34) | 3' primer to amplify 18S rRNA |

Primers used for making synthetic FTR1p in *E. coli*

| SynFtr1p P5 | CATCACCATGGGATCAAAAGAAT GTTTAATACTGAATCTCCA (SEQ ID NO: 35) | 5' primer to amplify synthetic Ftr1p |

TABLE 2-continued

Oligonucleotides used in this study.

| Primers | Sequence | Description |
| --- | --- | --- |
| SynFtr1p P6 | CTAATTAAGCTTGGCTTAAGCTTT AATAGCATCAGATTCAATTTTTC (SEQ ID NO: 36) | 3' primer to amplify synthetic Ftr1p |

To disrupt the FTR1, we constructed a gene disruption cassette encompassing a functional PyrF copy (998 bp) amplified from R. oryzae wild-type flanked by 606 and 710 bp fragments of FTR1-5' UTR and FTR1-3' UTR, respectively (FIG. 23A). The gene disruption construct was PCR amplified using primers FTR1 P1/P2 (Table 2) in order to obtain a 2.3 kb disruption fragment containing only the pyrF flanked by homologous FTR1 UTR sequence (FIG. 23A). This was then used to transform R. oryzae M16 (pyrF mutant) with biolistic bombardment (Skory, Mol Genet Genomics 268: 397-406 (2002)). The disruption cassette replaces the entire FTR1 coding region from −16 to the stop codon, with the pyrF gene fragment. Isolates obtained from two separate transformations were purified with one round of sporulation and single colony isolation on chemically defined medium (YNB+CSM−URA) supplemented with 1 mM FeCl3 (iron rich) to favor the segregation of the FTR1 null allele, since FTR1 expression in this iron concentration is suppressed (Fu et al., FEMS Microbiol Lett 235: 169-176 (2004)). Isolates were tested for integration of the disruption cassette with PCR primer pairs FTR1-P3/PyrF-P9 (expected 1054 bp) and PyrF-P18/FTR1-P4 (expected 1140 bp). Disruption of FTR1 was confirmed by the absence of a PCR amplification product using primers FTR1-P5/FTR1-P6 (expected 503) to amplify the ORF of FTR1 and by Southern blot analysis. In an effort to obtain a homokaryotic isolate containing the FTR1 null allele, transformants with confirmed integration in the FTR1 locus were further taken through 14 rounds of sporulation and single colony isolation on YNB+CSM−URA supplemented with 1 mM FeCl3.

Figure 23C:
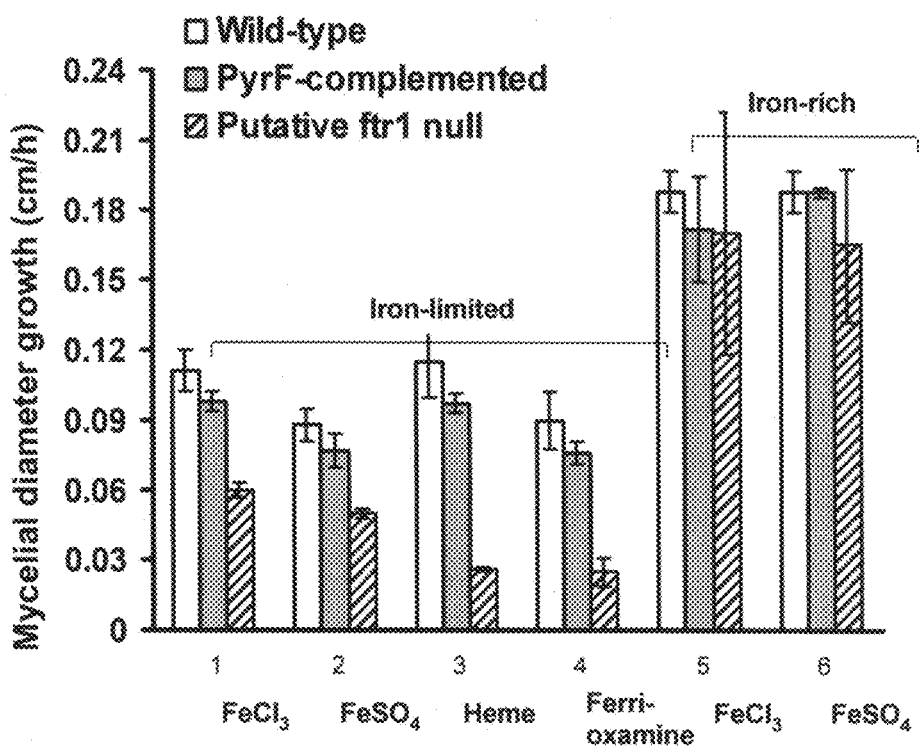
Figure 23:
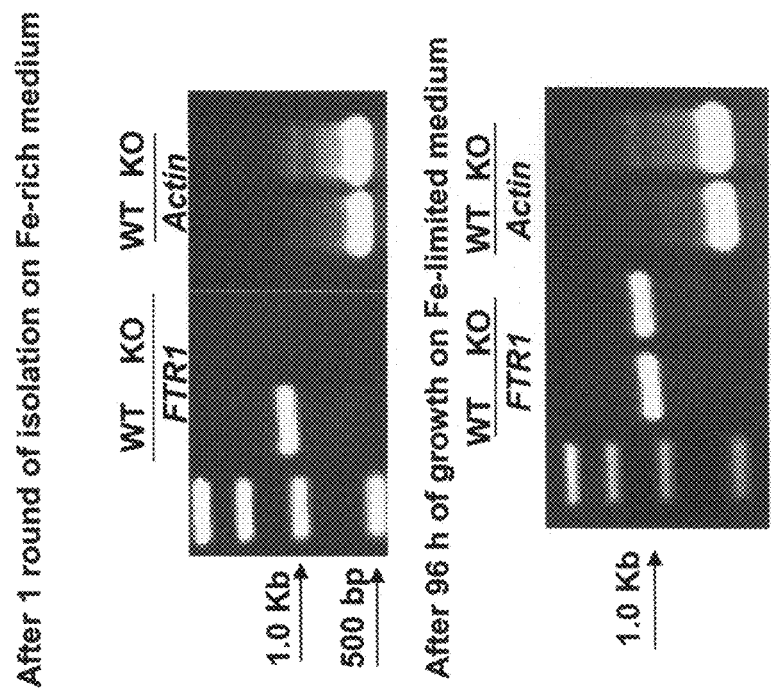

We previously found that FTR1 is expressed in vitro in iron-depleted conditions ($FeCl_3$ concentration between 0-50 $\mu M$) and suppressed in iron replete media ($FeCl_3$ concentrations of $\geq 350$ $\mu M$) (Fu et al., FEMS Microbiol Lett 235: 169-176 (2004)). To investigate if FTR1 disruption had an effect on the ability of R. oryzae to grow in media with different sources and concentration of iron, we compared growth of several putative null mutant strains to growth of wild-type or PyrF-complemented R. oryzae. Growth was compared on media (CSM−URA) which had been previously chelated for iron and then supplemented with defined concentrations of free iron (i.e. $FeCl_3$ or $FeSO_4$) or iron complexed to deferoxamine [ferrioxamine] or heme. Compared to wild-type or PyrF-complemented R. oryzae, putative ftr1 null mutant strains had significantly less growth at 48 h in iron-depleted media (i.e. free iron at 10 $\mu M$) (FIG. 23C). Ferrioxamine or iron complexed with heme at 100 $\mu M$ (relatively depleted because iron is complexed) supported the growth of the wild-type and PyrF-complemented strains better than the putative ftr1 null mutant. However, free iron at 1000 $\mu M$ (iron-rich media) supported the growth of all strains equally (FIG. 23C) consistent with our previous findings that ftr1 is primarily expressed in iron-depleted environments.

Growth of the putative ftr1 disruption mutants were compared to R. oryzae wild-type or R. oryzae PyrF-complemented strain by growing on plates YNB+CSM−URA supplemented with 10 or 1000 $\mu M$ of FeCl3, FeSO4, or with 100 $\mu M$ of heme, or ferroxamine as a source of iron. Additionally, putative ftr1 null or RNAi mutants were compared to their corresponding control strains for their growth on YPD or chemically defined medium (i.e. YNB+CSM−URA). Briefly, ten microliters of 105 spores of R. oryzae spores were spotted in the center of plates and the mycelial diameter was measured after 48 h of growth for medium containing FeCl3, FeSO4, or ferroxamine or for 72 h for plates supplemented with heme. The experiment was repeated three times on different days and growth rate was expressed as increase in mycelial diameter of the fungus per hour.

Interestingly, growth of the putative ftr1 null mutants increased to levels similar to the wild-type and PyrF-complemented strains after 96 h on iron-depleted media (data not shown). Furthermore, PCR analysis of these cultures after 96 h of growth confirmed that the FTR1 ORF was once again detectable in all of the putative ftr1 null mutant transformants (FIG. 23D). Similar results were obtained with several other putative ftr1 null mutants and it was concluded that one round of sporulation and single colony isolation was not sufficient to purify an ftr1 homokaryotic null allele strain.

R. oryzae is known to be coenocytic and it is generally presumed that sporangiospores are multinucleated, although the number of nuclei has not been previously described (Ma et al., PLoS Genet 5: e1000549 (2009)). Gene disruption appeared to be complicated by the presence of heterokaryotic nuclei in both the mycelium and sporangiospores, and the number of nuclei present in swollen spores using DAPI staining was determined. Briefly, to determine the number of nuclei present in R. oryzae spores, spores in YPD medium were pregerminated for 2 h at 37° C. Swollen spores were washed once with cold PBS then suspended at a concentration of 5×105/ml in PBS. One µl of 50 µg/ml of 4'6-diamidino-2-phenylindole (DAPI, Sigma) were added and the cells were electroporated (BioRad) according to the manufacturer instructions. The swollen spores were washed five times using cold PBS prior to resuspending in 100 µl PBS. Ten µl sample was placed on a glass slide and covered with a coverslip. The stained cells were visualized using an epifluorescence microscope.

Figure 24A:
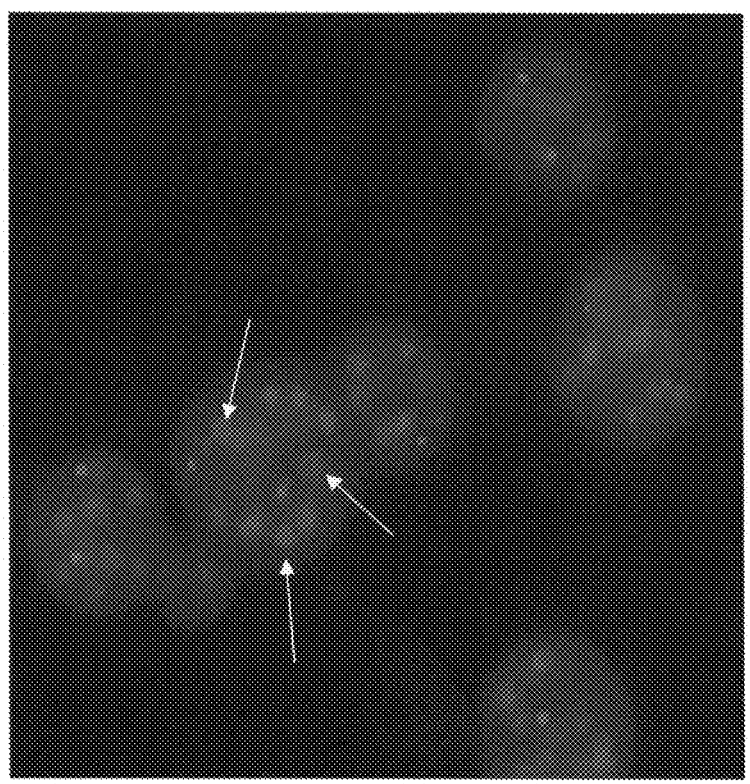
FIG. 24, panels A, B and C, show confirmation of the lack of complete disruption of FTR1 in the multinucleated *R. oryzae*. Panel (A) DAPI stain of swollen *R. oryzae* spores showing the presence of multiple nuclei with a single spore. Arrows denote nuclei. Original magnification, ×1000. Panel (B) Gel electrophoresis showing lack of amplification of FTR1 after 14 passages of the putative null mutants on iron-rich medium (1000 μM FeCl3) and amplification of the FTR1 from the same isolate following growth on iron-depleted medium (i.e. 100 μM ferrioxamine) for 96 h. Amplification of actin (600 bp) was used to confirm the integrity of DNA used as template and the absence of PCR inhibitors. Panel (C) Southern blot confirming the integration of the disruption cassette in the putative ftr1 (7380 bp band is present only in DNA sample extracted from putative ftr1 grown in iron-rich medium) and almost complete elimination of the FTR1 copy (lack of 1960 bp in DNA sample extracted from putative ftr1 grown in iron-rich medium).
Figure 24B:
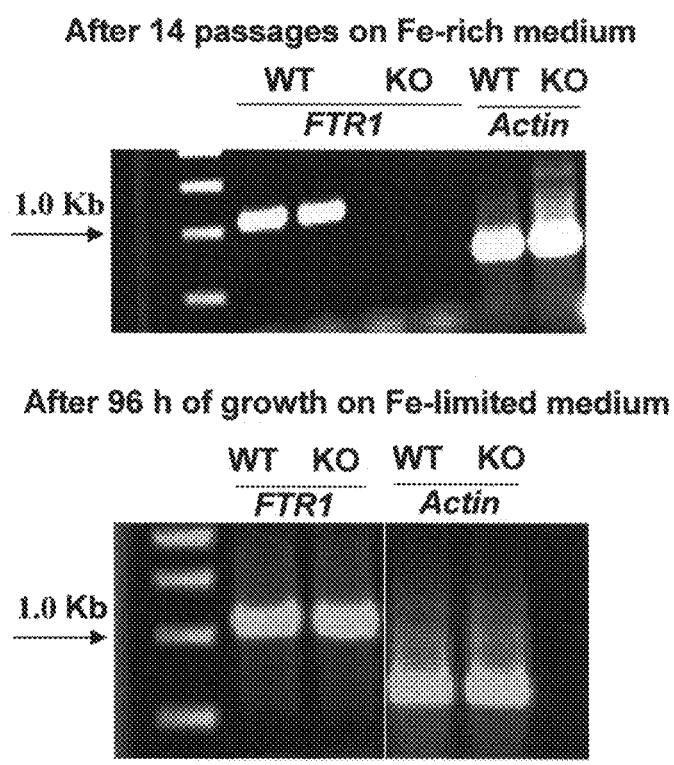
Figure 24C:
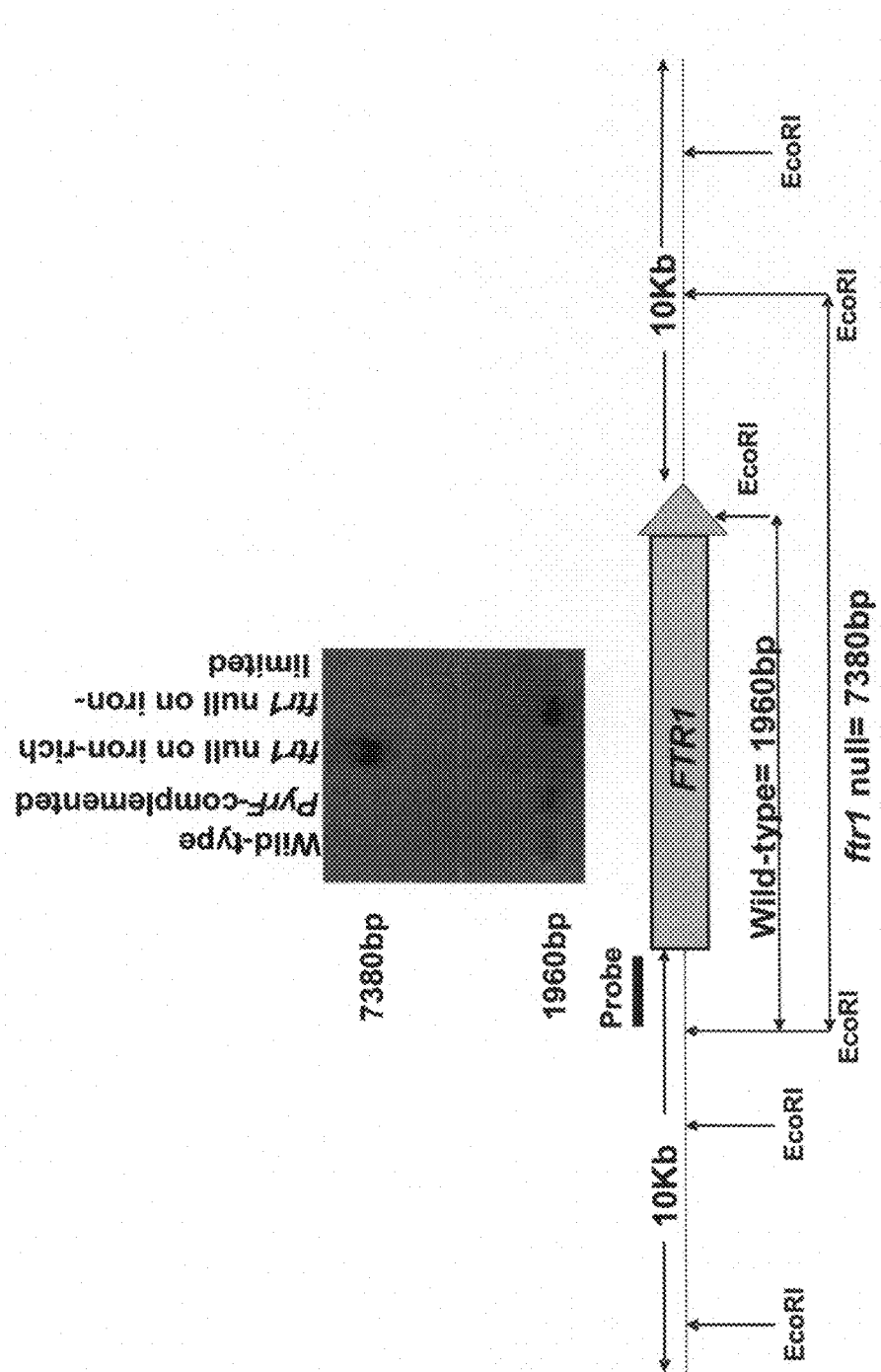

It was found that R. oryzae strain M16 had more than 10 nuclei per swollen spore (FIG. 24A). Given the high number of nuclei present, 14 rounds of sporulation and single colony isolation of putative ftr1 null mutants on iron-rich medium (i.e. medium containing 1000 µM of $FeCl_3$) were performed to segregate the null alleles by relieving the selective pressure for maintaining FTR1 (since FTR1 is poorly expressed in iron-rich conditions) (Fu et al., FEMS Microbiol Lett 235: 169-176 (2004)). PCR analysis of the putative null mutants after 14 rounds of selection demonstrated lack of amplification of FTR1 ORF (FIG. 24B). Similar to the results in FIG. 23C, the null mutant had defective growth on iron limited sources for the first 48 h compared to wild-type or PyrF-complemented strains. However, after growth of the same putative null mutants in iron-depleted environment (100 µM ferrioxamine), the FTR1 ORF was once again amplified by PCR. These results were confirmed with Southern blot analysis (FIG. 24C). The Southern blot demonstrated almost complete elimination of the FTR1 band (1960 kb) from gDNA of the putative ftr1 null mutants grown on iron-rich medium, but return of the FTR1 band after growth of the same strain on iron-depleted medium (FIG. 24C). Additionally, Southern hybridization analysis confirmed the site-specific integration of the disruption cassette into the ftr1 locus only when the putative ftr1 null mutant was grown in iron-rich medium. Finally, there was no evidence of ectopic integration or extrachromosomal replication, consistent with the fact that the relative copy number of the ftr1 null allele was dependent on the ratio of heterokaryotic nuclei.

Figure 25A:
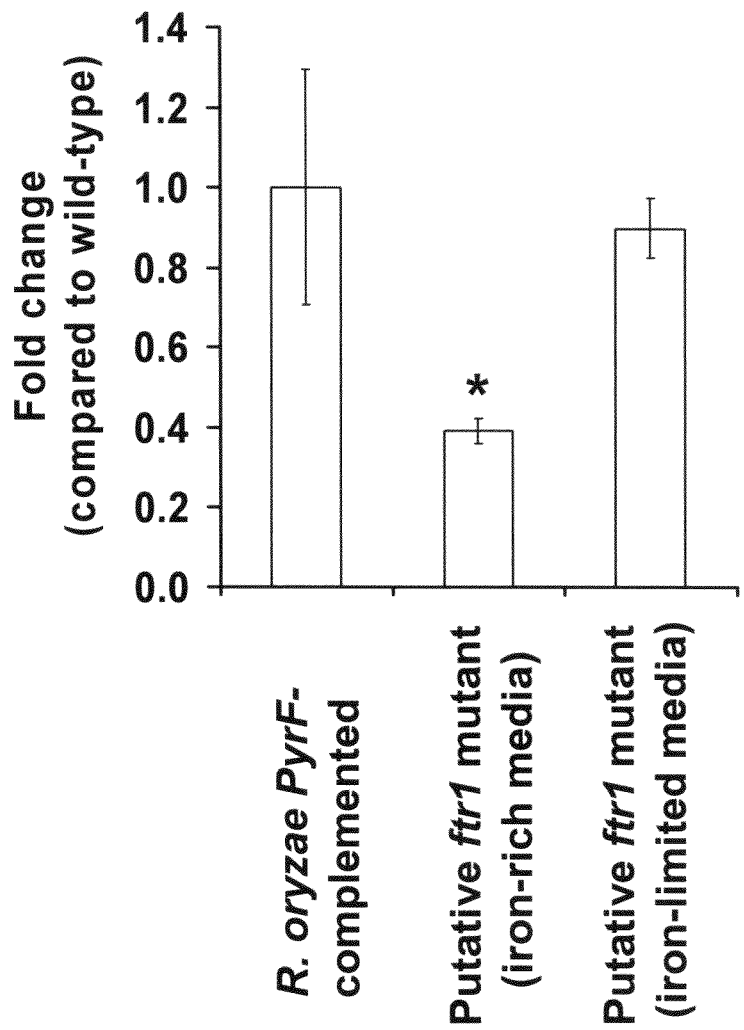
FIG. 25, panels A, B and C, show that reduced copy number results in compromised ability of *R. oryzae* to take up iron. Panel (A) Quantitative PCR demonstrating reduced copy number in the putative ftr1 null mutant compared to *R. oryzae* PyrF-complemented strain or to the same mutant grown in iron-depleted medium. Panel (B) Gel electrophoresis of samples taken from the qPCR tube showing the amplification specificity for the FTR1 product. Panel (C) The putative ftr1 mutant demonstrated reduced ability to acquire 59Fe compared to *R. oryzae* wild-type or *R. oryzae* PyrF-complemented strains. 59Fe uptake by wild-type, *R. oryzae* PyrF-complemented, or putative ftr1 mutant. Germinated spores were incubated with 0.1 μM 59FeCl3 (a concentration in which high-affinity iron permeases are induced (Fu et al., *FEMS Microbiol Lett* 235: 169-176 (2004)). *$P<0.05$ when compared with *R. oryzae* wild-type or *R. oryzae* PyrF-complemented strains. Data (n=9 from three separate experiments) are expressed as medians+interquartile ranges.
Figure 25B:
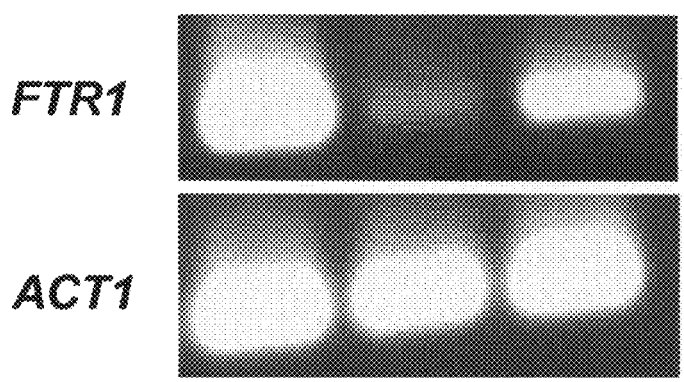

To compare the copy number of FTR1 in the putative ftr1 null mutant grown on iron-rich or iron-limited media or to those of PyrF-complemented strain, qPCR was used. Briefly, genomic DNA was extracted with the OmniPrep lysis buffer (GBiosciences) from PyrF-complemented $R.$ $oryzae$ grown in YNB+CSM–URA supplemented with 1 mM FeCl3 or putative ftr1 null mutant grown in either YNB+CSM–URA supplemented with 1 mM FeCl3 or 100 μM ferrioxamine. FTR1 copy number in each sample was determined by qPCR using an ABI Prism 7000 Sequence Detection System (Applied Biosystems) and amplification products were detected with Power Sybr Green Cells-to-CTTM kit (Applied Biosystems). PCR conditions were as follows: denaturing at 95° C. for 15 s min and amplification 40 cycles with annealing/extension carried out at 60° C. for 1 min. FTR1 copy numbers were then normalized to $R.$ $oryzae$ ACT1, and relative copy number was estimated using the formula $2^{-\Delta\Delta CT}$, where $\Delta CT=[Ct_{target\ gene}-Ct_{ACT1}/]$ and $\Delta\Delta CT=[ACT$ of mutant–ACT of PyrF-complmented strain].

qPCR was used to quantify the copy number of FTR1 in a putative ftr1 null mutant that was passed through 14 rounds of sporulation and single colony isolation on iron-rich media, as well as the same strain after growth in iron-depleted media, and the $R.$ $oryzae$ PyrF-complemented strain. The putative ftr1 null mutant strain grown in iron-rich media had a 60% reduction in the relative copy number of FTR1 (normalized to ACT1 gene) compared to the same strain grown in iron-depleted media or to the $R.$ $oryzae$ PyrF-complemented strain (FIGS. 25A and 25B). Thus, while it was possible to significantly decrease the relative copy number of functional FTR1 in multinucleated $R.$ $oryzae$, a homokaryotic isolate of this mutant allele was not obtained.

Example 14

Figure 25C:
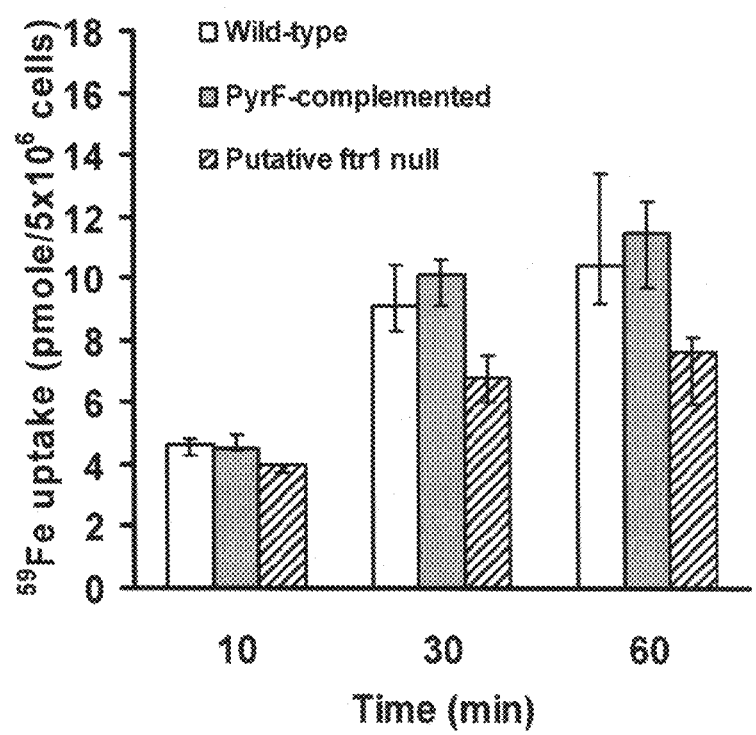

Reduction of the FTR1 Copy Number Attenuates Iron Uptake In Vitro and Reduces Virulence In Vivo As shown herein, reduction of the relative copy number of functional FTR1 in $R.$ $oryzae$ is sufficient to decrease iron uptake and therefore reduce virulence. The putative ftr1 null mutant had a ~35% reduction in $^{59}Fe$ uptake compared to wild-type or $R.$ $oryzae$ PyrF-complemented strain (FIG. 25C).

Figure 26A:
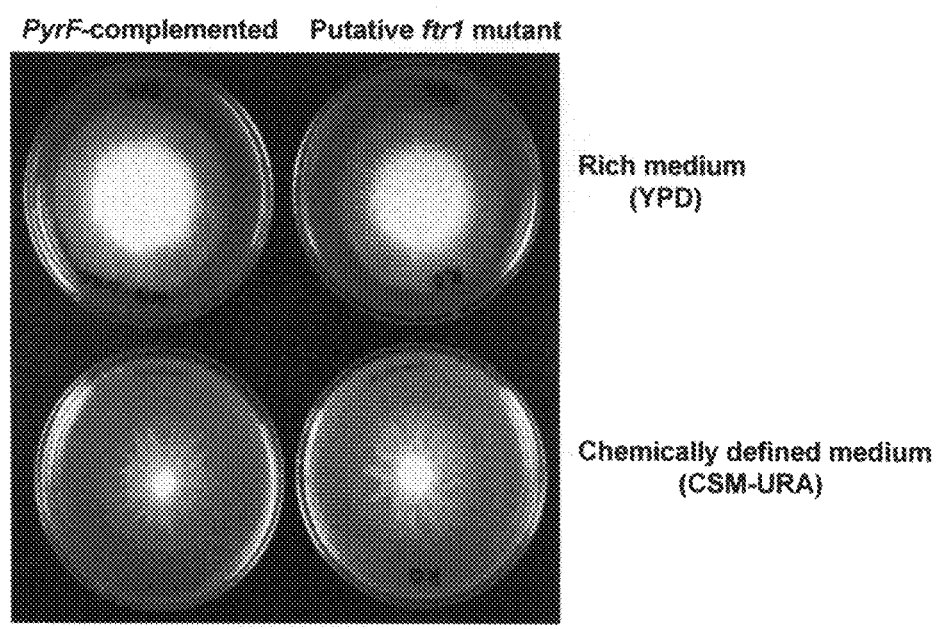
FIG. 26, panels A, B and C, show how the reduction of FTR1 copy number reduces *R. oryzae* virulence in the DKA mouse models. Panel (A) a representative of the putative ftr1 null mutant demonstrated comparable growth to *R. oryzae* PyrF-complemented strain on YPD or CSM-URA media. Panel (B) Survival of mice (n=8) infected i.v. with *R. oryzae* wild-type ($4.3\times10^3$), *R. oryzae* PyrF-complemented strain ($4.8\times10^3$ spores) or with putative ftr1 null mutant ($3.0\times10^3$ spores). *, $P<0.0005$ compared to wild-type or PyrF-complemented strains. Panel (C) Survival of mice (n=9) infected intranasally with *R. oryzae* wild-type ($4.3\times10^3$ spores), *R. oryzae* PyrF-complemented strain ($5.1\times10^3$ spores) or putative ftr1 null mutant ($5.3\times10^3$ spores). *, $P=0.04$ compared to wild-type or PyrF-complemented strains.
Figure 26B:
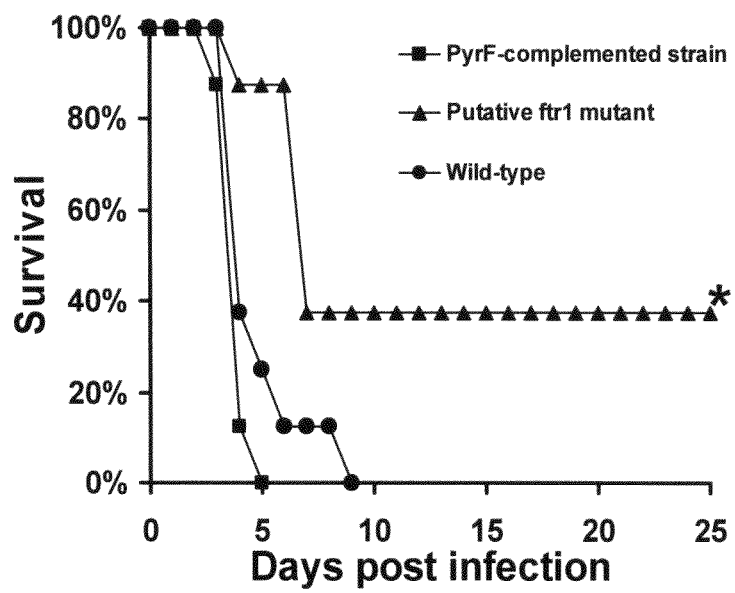
Figure 26C:
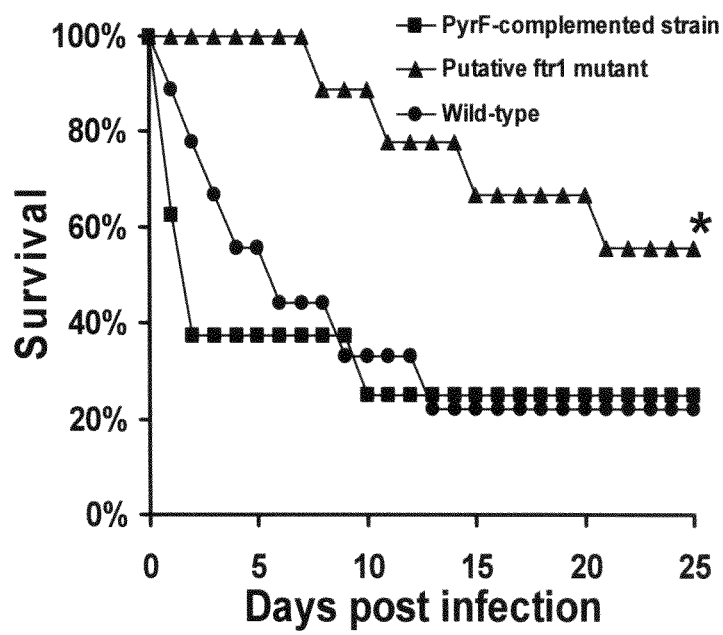

To determine the in vivo relevance of the diminished in vitro iron uptake of the putative ftr1 null mutant, its virulence was compared to $R.$ $oryzae$ wild-type or PyrF-complemented strains during infection in mice with DKA. Mice were infected intravenously (i.v.) or intranasally (i.n.) with strains that demonstrated similar growth in vitro on iron-rich environment of YPD or CSM–URA (0.185±0.005 or 0.257±0.003 cm/h for the putative ftr1 null vs. 0.188±0.008 or 0.260±0.0051 cm/h for the PyrF-complemented on iron rich CSM–URA or YPD medium, respectively) (FIG. 26A). In both models, the putative ftr1 null mutant showed reduced virulence compared to the wild-type or PyrF-complemented strain (62% vs. 100% mortality for mutant vs. control strains in mice with disseminated infection, and 44% vs. 75% mortality for mutant vs. control strains in the intranasal model) (FIG. 26B,C). As expected colonies retrieved from moribund animals infected with the putative ftr1 null mutant strain demonstrated similar copy numbers of FTR1 compared to the pyrF-complemented strain (data not shown), indicative of restoration of FTR1 copy number as was seen after growth in iron-depleted environments in vitro. Additionally, in both models the pyrF-complemented strain had similar virulence to the wild-type $R.$ $oryzae$, demonstrating that restoration of the pyrF gene in its original locus does not affect virulence.

Example 15

Inhibition of FTR1 Gene Expression by RNAi Reduces Iron Uptake and Diminishes Virulence of $R.$ $oryzae$ To confirm the phenotypes seen after gene disruption, RNA interference (RNAi) was used to diminish FTR1 expression in $R.$ $oryzae.$ RNA interference (RNAi) technology was utilized to inhibit the expression of FTR1 in $R.$ $oryzae.$ A 450 bp fragment of FTR1 ORF containing the REGLE motif (SEQ ID NO:3) believed to interact with iron during uptake (Stearman et al., *Science* 271: 1552-1557 (1996)) was PCR amplified and cloned as an inverted repeat under control of the *Rhizopus* expression vector pPdcA-Ex (Mertens et al., *Archives of microbiology* 186: 41-50 (2006)). Additionally, an intron from the *Rhizopus* pdcA gene (Skory, *Curr Microbiol* 47: 59-64 (2003)) was included between repeat to serve as a linker for stabilization of the intended dsRNA structure (Nakayashiki et al., *Fungal Genet Biol* 42: 275-283 (2005); Wesley et al. *Plant J* 27: 581-590 (2001)). The generated plasmid was transformed into $R.$ $oryzae$ pyrF mutant using the biolistic delivery system (BioRad) and transformants were selected on minimal medium lacking uracil.

Figure 27A:
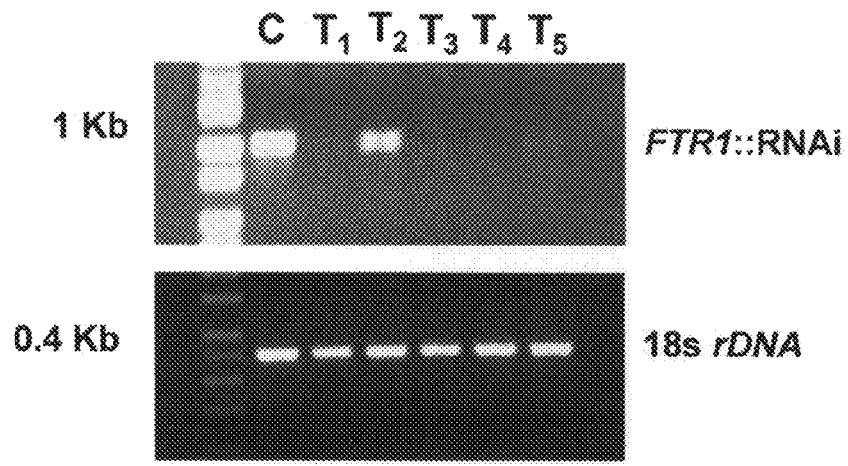
FIG. 27, panels A, B and C, show how inhibition of FTR1 expression reduces *R. oryzae* ability to take up $^{59}$Fe in vitro. Panel (A) RT-PCR showing lack of expression of FTR1 in *R. oryzae* transformed with RNA-interference plasmid ($T_1$ and $T_3$-$T_5$) compared to *R. oryzae* transformed with empty plasmid (C, control). Primers amplifying the 18s rDNA served as a control to demonstrate the integrity of starting sample and lack of PCR inhibitors. Panel (B) a representative of the RNAi transformants demonstrated comparable growth to the *R. oryzae* M16 transformed with empty plasmid on YPD or CSM-URA media. Panel (C) $^{59}$Fe uptake by wild-type, *R. oryzae* M16 transformed with the empty plasmid, or one of the RNAi transformants. Germinated spores were incubated with 0.1 μM $^{59}$FeCl$_3$ (a concentration in which high-affinity iron permeases are induced (Fu et al., *FEMS Microbiol Lett* 235: 169-176 (2004)). *$P<0.05$ when compared with *R. oryzae* wild-type or *R. oryzae* M16 transformed with empty plasmid. Data (n=9 from three separate experiments) are expressed as medians+interquartile ranges.
Figure 27B:
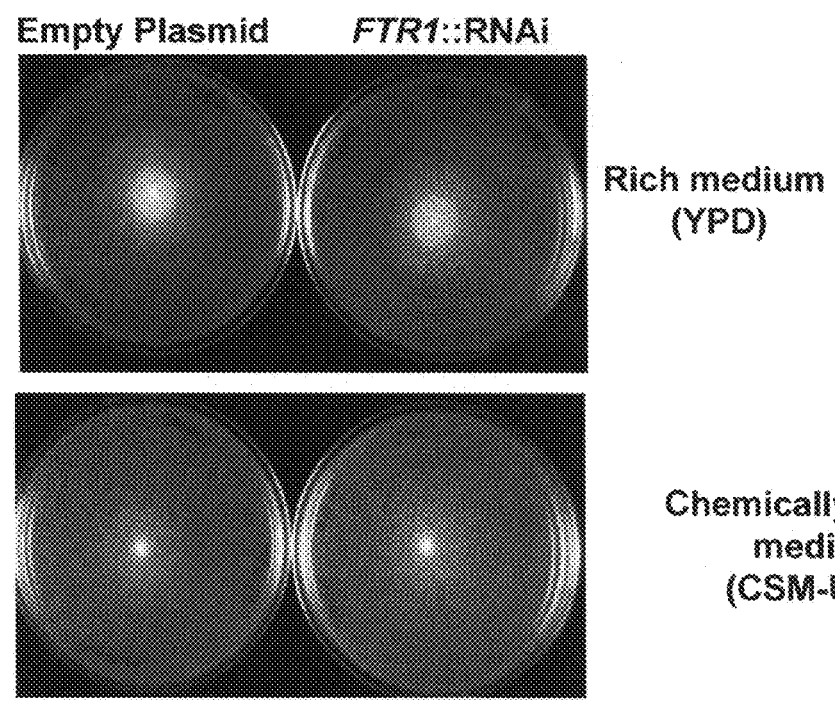

Southern blot analysis (data not shown) revealed that all RNAi transformants maintained the transformed plasmid extrachromosomally, consistent with the fact that we did not linearize the plasmid during transformation (Skory, *Mol Genet Genomics* 268: 397-406 (2002)). FTR1 expression was compared by end-point RT-PCR in five transformants vs. the control strain (i.e. $R.$ $oryzae$ pyrf null mutant [M16] transformed with empty-plasmid). FTR1 expression was almost completely blocked in 4 transformants, while readily detected in the control strain (FIG. 27A). Amplification of 18s rDNA with the same RT templates demonstrated the integrity of the starting sample and the lack of PCR inhibitors Inhibition of FTR1 expression by RNAi was specific, with no apparent reduction in off-site gene expression. A representative RNAi transformant demonstrated similar growth to control strain when grown on either iron rich YPD or CSM–URA media (0.193±0.082 or 0.205±0.016 cm/h for the transformant vs. 0.201±0.087 or 0.211±0.011 cm/h for the control strain on iron rich CSM–URA or YPD medium, respectively) (FIG. 27B).

Figure 27C:
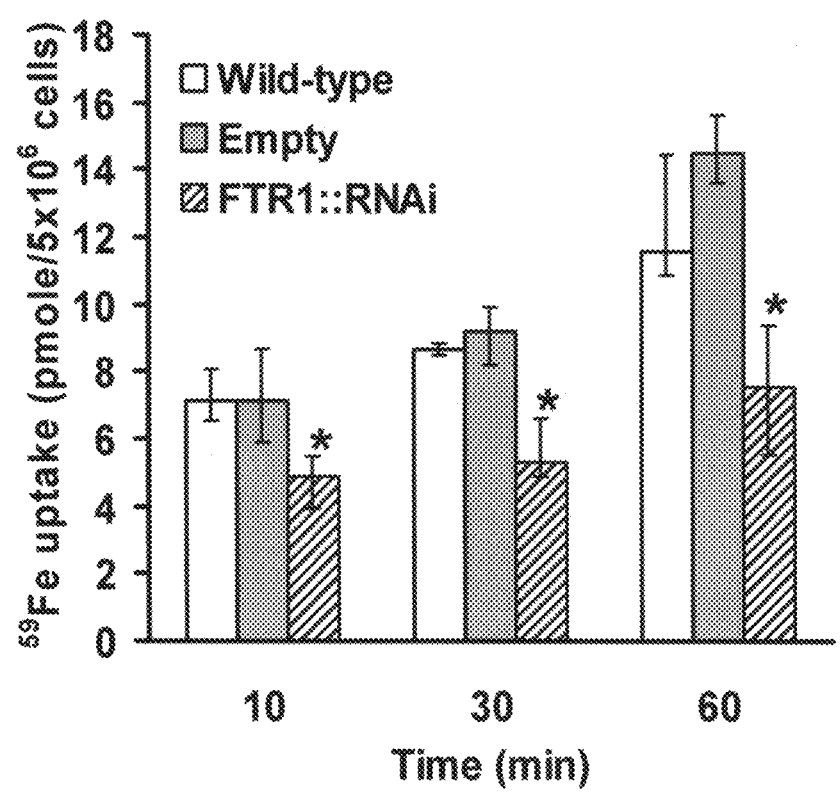

The ability to take up iron was tested in vitro of the transformant with near complete inhibition of FTR1 expression and similar growth to the control strain. Interestingly, RNAi decreased $^{59}Fe$ uptake by $R.$ $oryzae$ more effectively than did gene disruption, with ~50% inhibition of iron uptake at all times tested (FIG. 27C). Briefly, to characterize the effect of FTR1 manipulation on the ability of R. oryzae to take up iron in vitro, ftr1 putative disruption mutant or the RNAi mutant were compared to wild-type or R. oryzae PyrF-complemented strains in their ability to accumulate intracellular $^{59}$FeCl3 (Amersham Pharmacia Biotech) using a modification of our published method (Fu et al., FEMS Microbiol Lett 235: 169-176 (2004)). Spores were pre-germinated for 3 h YPD medium supplemented with 1 mM ferrozine and 1 mM ascorbic acid at 37° C. with shaking. Cells were harvested by centrifugation, washed twice with ice cold assay buffer pH 6.1 (minimal medium+10 mM 4-morpholinepropanesulfonic acid+1 mM ferrozine), and then resuspended in assay buffer without any ferrozine to give a concentration of 108 cells per ml. To measure uptake of $^{59}$Fe, 50 µl of the cell suspension was added to 450 µl of chilled assay buffer without ferrozine but supplemented with 0.1 1M 59FeCl3, and incubated in a shaking water bath at 30° C. After selected time points, the assay samples were chilled on ice, vortexed, vacuum filtered through Whatman GF/C filters and washed with 10 ml ice cold SSW (1 mM EDTA, 20 mM Na3-citrate pH 4.2, 1 mMKH2PO4, 1 mM CaCl2, 5 mM MgSO4, 1 mM NaCl). Filters were removed and placed in glass scintillation vials containing 10 ml scintillation fluid (Filter-count). Cell-associated $^{59}$Fe was counted in a Packard 2200CA liquid scintillation counter (Packard Instrument Co., Downers Grove, Ill.). Nonspecific uptake due to cell surface adsorption was determined by preparing parallel assays that were held on ice for 10 min before filtration and washing. The background levels of $^{59}$Fe were subtracted before calculation of uptake rates. The experiment was carried out in triplicate and repeated three times on different days. The data is presented as specific uptake in pmole/5×10$^6$ germinated spores.

Figure 28A:
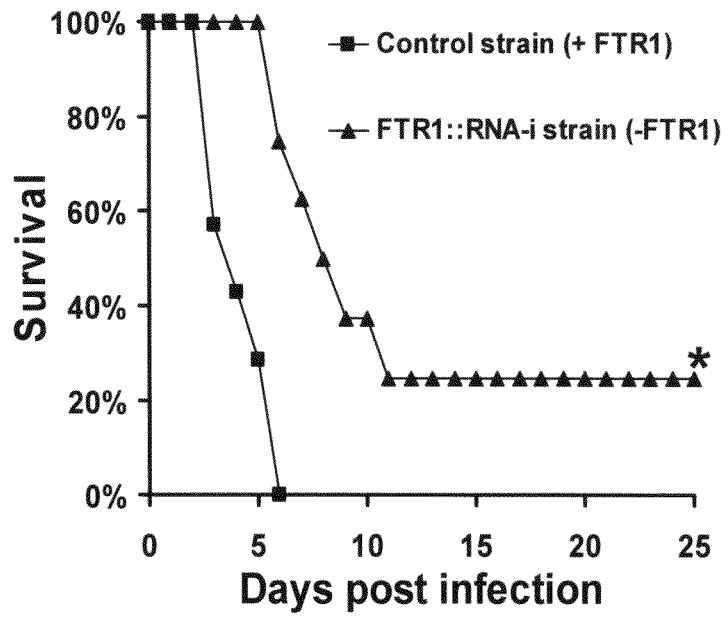
FIG. 28, panels A, B, C and D, show how inhibition of FTR1 expression reduces virulence of *R. oryzae* in the DKA mouse models and passive immunization with anti-Ftr1p sera protects DKA mice from *R. oryzae* infection. Panel (A) Survival of mice (n=8) infected i.v. with *R. oryzae* transformed with empty plasmid (control strain, $2.9\times10^3$ spores) or with RNA-i plasmid targeting expression of FTR1 (FTR1-i, $4.1\times10^3$ spores). *, $P<0.001$. Panel (B) Survival of mice (n=9) infected intranasally with *R. oryzae* transformed with empty plasmid (control strain, $2.8\times10^3$ spores) or with RNAi plasmid targeting expression of FTR1 (FTR1-i, $7.6\times10^3$ spores). *, $P<0.02$. Panel (C) Kidney or brain Fungal burden of mice (n=8) infected i.v. with *R. oryzae* transformed with empty plasmid (control strain, $4.2\times10^3$ spores) or with RNAi plasmid targeting expression of FTR1 (FTR1-i, $5.1\times10^3$ spores). *, $P<0.0006$ and ¥, $P<0.04$ compared to control strain. Data are expressed as medians+interquartile ranges. The y-axes reflect lower limits of detection of the assay. Panel (D) Survival of mice (n=8) infected intranasally with *R. oryzae* (intended inoculum of $2.5\times10^7$ spores and actual inhaled inoculum of $9\times10^3$ spores) and treated with serum collected from mice immunized with either Ftr1p or proteins collected form empty plasmid clone. *, $P<0.007$.
Figure 28B:
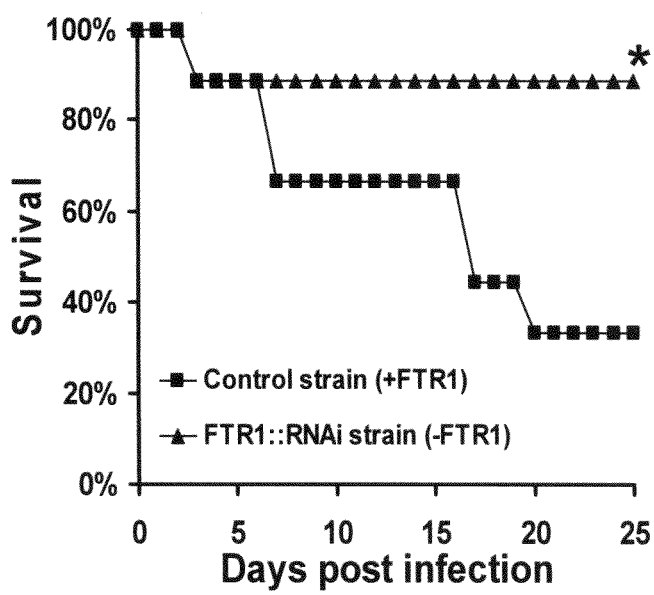
Figure 28C:
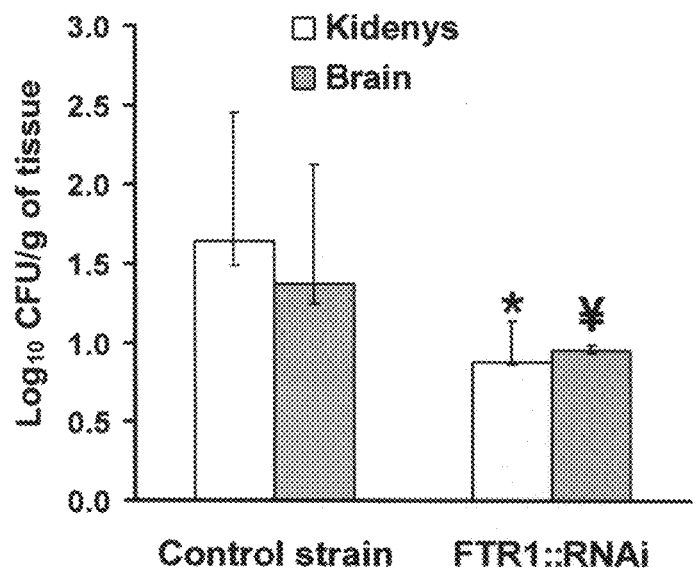

Next, the virulence of the RNAi transformant was compared to the control strain in the DKA mouse models of hematogenously disseminated or intranasal mucormycosis. The RNAi-transformant demonstrated reduced virulence compared to the control strain in both models (75% vs. 100% mortality for RNAi transformant vs. control strain in mice with disseminated infection, and 11% vs. 67% mortality for RNAi transformant vs. control in the intranasal model, p<0.02 for both comparisons by Log Rand test) (FIG. 28A, B). Interestingly, strains recovered from kidneys of mice that died of infection with the RNAi transformant had lost the RNAi plasmid as evident by growth of R. oryzae colonies on YPD plates and not YNB+CSM−URA (data not shown), and hence had regained ability to express FTR1. In contrast, strains recovered from kidneys of mice that survived the infection through day 25, when the experiment was terminated, had not lost their RNAi plasmid. Additionally, mice infected intravenously with the RNAi transformant had a ~6- and 3-fold reduction in kidney and brain fungal burden compared to mice infected with control strain, respectively (FIG. 28C). These data demonstrate that the FTR1 gene product is a pivotal virulence factor for R. oryzae in DKA mice.

Example 16

Passive Immunization with Sera Collected from Mice Vaccinated with Ftr1p Protects Mice from R. oryzae Infection This example demonstrates that passive immunization targeting FTR1 would protect against mucormycosis.

Figure 28D:
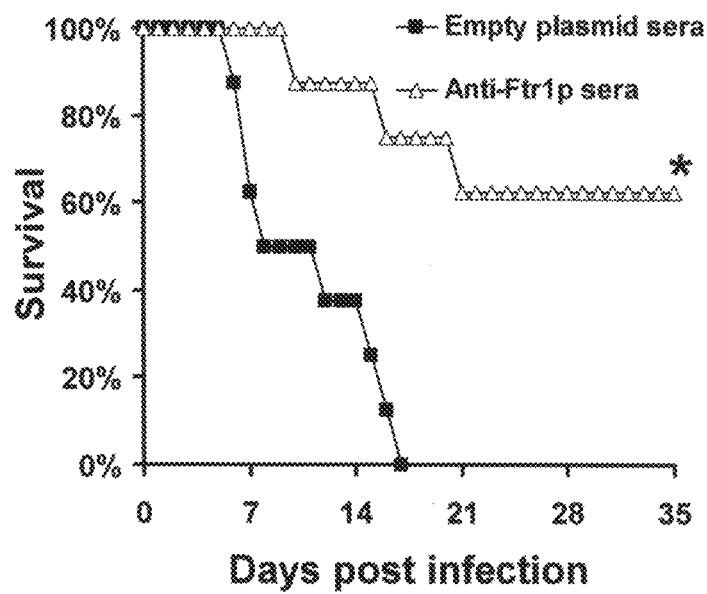

To generate immune serum for passive immunization, mice were immunized by SQ injection of Ftr1p mixed with complete Freund's adjuvant (CFA) followed by a boost with another dose of the antigen with incomplete Freund's adjuvant (IFA) at day 21, and bled for serum collection two weeks later. Another set of mice were vaccinated with supernatants collected from E. coli transformed with empty plasmid to generate non-immune control serum. Antibody titers were determined using ELISA plates coated with 5 µg of synthetic recombinant Ftr1p as we previously described (Ibrahim et al., Infect Immun 73: 999-1005 (2005)). Immune or control sera (0.25 ml) were administered i.p. to diabetic ketoacidosis recipient mice 2 h before intranasal infection with 2.5×107 R. oryzae 99-880 spores. Sera doses were repeated 3 days post infection and survival of mice was followed for 35 days post infection. Pooled sera collected from vaccinated mice had anti-Ftr1p IgG titers of >1:800,000, whereas pooled sera collected from negative control mice vaccinated with purified supernatant from an empty plasmid transformed clone had an anti-Ftr1p IgG titer of 1:200. Administration of immune sera to DKA mice subsequently infected intranasally with R. oryzae significantly improved survival compared to mice treated with control serum (63% vs. 0% survival for immune sera vs. non-immune sera, p<0.001) (FIG. 28D).

Throughout this application various publications have been referenced. The disclosures of these publications in their entireties are hereby incorporated by reference in this application in order to more fully describe the state of the art to which this invention pertains.

Although the invention has been described with reference to the disclosed embodiments, those skilled in the art will readily appreciate that the specific examples and studies detailed above are only illustrative of the invention. It should be understood that various modifications can be made without departing from the spirit of the invention. Accordingly, the invention is limited only by the following claims.

What is claimed is:

1. A pharmaceutical composition comprising a pharmaceutically acceptable excipient or carrier and an inhibitor of a high affinity iron permease (FTR) polypeptide of *Rhizopus oryzae*, wherein the inhibitor is an antibody or a fragment of said antibody that specifically binds to an immunogenic FTR polypeptide fragment comprising a hydrophilic extracellular region of an FTR polypeptide of *Rhizopus oryzae* and lacking the signal peptide and six transmembrane domains of said FTR polypeptide that direct localization of the polypeptide to the cell membrane.

2. The pharmaceutical composition of claim 1, wherein said FTR polypeptide of *Rhizopus oryzae* comprises the amino acid sequence encoded by the nucleic acid sequence of SEQ ID NO: 1.

3. The pharmaceutical composition of claim 1, wherein said immunogenic FTR polypeptide fragment comprises the amino acid sequence of REGLE (SEQ ID NO: 3).

* * * * *

SEQUENCE LISTING

<160> NUMBER OF SEQ ID NOS: 45

<210> SEQ ID NO 1
<211> LENGTH: 1107
<212> TYPE: DNA
<213> ORGANISM: Rhizopus oryzae

<400> SEQUENCE: 1

```
atgtctcaag atctcttcaa cgtaccgatc ttctttatcc tttttcgtga aacgactgag      60
gcagccatca ttatttctgt cctcttgtca ttcttgaaga gaatgtttaa tacagaatct     120 cctgttata aacgtctcag aaatcaagtc tggattggtg gtgcagctgg tctgtttatc     180
```

```
tgtttatgta tcggtgctgc cttcattgcc gtttactaca ctgtccttaa tgacttgtgg      240
ggaaattctg aagatatctg ggaaggtgtc ttctctctgg ttgctgtgat catgatcact      300
gccatgggtc ttgctatgct caagactgaa cgtatgcaag aaaagtggaa ggtcaagttg      360
gctaaagcaa tgcaaaagtc aacagtgaaa agtcatcct ttaaagaaaa acttcaaaaa       420
tacgcgttct ttgtcttgcc ttttatcacc gttctcagag aaggacttga agctgttgtc      480
tttattggtg gtgtctcctt gggtatccaa ggaaaatcaa ttcctattgc tgccatcatg      540
ggtatcatct gtggtgtttt ggtcggtttc cttatttacc gtggtggttc cttgattcaa      600
cttcgttggt tctttgtgtt ctctactgtc gttctttacc ttgtcgctgc tggtttgatg      660
gctaaaggtg ttggttacct tgaacaaaat gcttggaatc aagtcattgg tggtgaagct      720
gctgatgtca ttagttacag agtctcaacc gctgtctggc acgtttcttg gggagaccca      780
gaagccaaca atgataccte tggtggttgg caaatctta acgccattct tggttggaac       840
aatacggcta cttatggttc tatcatcagt tactgtctct actggctctt tgtctgctgt      900
tatcttgtct ttagttactt taaggaaaag cgtgctgcta tccgtaaagc cgaggctggt      960
gaatgggatg atggtgatga agctttggag aatgccaaac aatacattgg taatgatggt     1020
gaattcatcg ttgaagacaa agaatctgat gaagaagcca acaatcatcc caaggaaaaa     1080
atcgaatctg atgctattaa ggcttaa                                         1107
```

<210> SEQ ID NO 2
<211> LENGTH: 368
<212> TYPE: PRT
<213> ORGANISM: Rhizopus oryzae

<400> SEQUENCE: 2

Met Ser Gln Asp Leu Phe Asn Val Pro Ile Phe Ile Leu Phe Arg
1               5                   10                  15

Glu Thr Thr Glu Ala Ala Ile Ile Ile Ser Val Leu Leu Ser Phe Leu
            20                  25                  30

Lys Arg Met Phe Asn Thr Glu Ser Pro Val Tyr Lys Arg Leu Arg Asn
        35                  40                  45

Gln Val Trp Ile Gly Gly Ala Ala Gly Leu Phe Ile Cys Leu Cys Ile
    50                  55                  60

Gly Ala Ala Phe Ile Ala Val Tyr Tyr Thr Val Leu Asn Asp Leu Trp
65                  70                  75                  80

Gly Asn Ser Glu Asp Ile Trp Glu Gly Val Phe Ser Leu Val Ala Val
                85                  90                  95

Ile Met Ile Thr Ala Met Gly Leu Ala Met Leu Lys Thr Glu Arg Met
            100                 105                 110

Gln Glu Lys Trp Lys Val Lys Leu Ala Lys Ala Met Gln Lys Ser Asn
        115                 120                 125

Ser Glu Lys Ser Ser Phe Lys Glu Lys Leu Gln Lys Tyr Ala Phe Phe
    130                 135                 140

Val Leu Pro Phe Ile Thr Val Leu Arg Glu Gly Leu Glu Ala Val Val
145                 150                 155                 160

Phe Ile Gly Gly Val Ser Leu Gly Ile Gln Gly Lys Ser Ile Pro Ile
                165                 170                 175

Ala Ala Ile Met Gly Ile Ile Cys Gly Cys Leu Val Gly Phe Leu Ile
            180                 185                 190

Tyr Arg Gly Gly Ser Leu Ile Gln Leu Arg Trp Phe Phe Val Phe Ser
        195                 200                 205

```
          Thr Val Val Leu Tyr Leu Val Ala Ala Gly Leu Met Ala Lys Gly Val
              210                 215                 220

Gly Tyr Leu Glu Gln Asn Ala Trp Asn Gln Val Ile Gly Gly Glu Ala
          225                 230                 235                 240

Ala Asp Val Ile Ser Tyr Arg Val Ser Thr Ala Val Trp His Val Ser
                          245                 250                 255

Trp Gly Asp Pro Glu Ala Asn Asn Asp Thr Ser Gly Gly Trp Gln Ile
                      260                 265                 270

Phe Asn Ala Ile Leu Gly Trp Asn Asn Thr Ala Thr Tyr Gly Ser Ile
                  275                 280                 285

Ile Ser Tyr Cys Leu Tyr Trp Leu Phe Val Cys Cys Tyr Leu Val Phe
              290                 295                 300

Ser Tyr Phe Lys Glu Lys Arg Ala Ala Ile Arg Lys Ala Glu Ala Gly
          305                 310                 315                 320

Glu Trp Asp Asp Gly Asp Glu Ala Leu Glu Asn Ala Lys Gln Tyr Ile
                          325                 330                 335

Gly Asn Asp Gly Glu Phe Ile Val Glu Asp Lys Glu Ser Asp Glu Glu
                      340                 345                 350

Ala Asn Asn His Pro Lys Glu Lys Ile Glu Ser Asp Ala Ile Lys Ala
                  355                 360                 365

<210> SEQ ID NO 3
<211> LENGTH: 5
<212> TYPE: PRT
<213> ORGANISM: Unknown
<220> FEATURE:
<223> OTHER INFORMATION: Description of Unknown: Conserved motif
      sequence derived from multiple organisms

<400> SEQUENCE: 3

Arg Glu Gly Leu Glu
1               5

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 4

His His His His His His
1               5

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ggtggtgtct ccttgggtat                                              20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 6
aaggaaaccg accaaacaac                                              20

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ccagactggc ttgtctgtaa tc                                           22

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
aagtcaaatt gtcgttggca                                              20

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tgaacaagaa atgcaaactg c                                            21

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
cagtaatgac ttgaccatca gga                                          23

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ttcgaaaaga ccgtcaggat tagc                                         24

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
```
gagggacaca agcaagcaga aagt                                              24

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
cacttacggc cattttccat tgac                                              24

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cgcgctaaat gaacaaagaa t                                                 21

<210> SEQ ID NO 15
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
atgtctcaag atctcttcaa ccgtacc                                           27

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ttaagcctta atagcatcag attcg                                             25

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gatcactgcc atgggtcttg ctat                                              24

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
tatcatgttg gcttctgggt ctc                                               23

<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gccgtggcgc agacaagag                                                   19

<210> SEQ ID NO 20
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gtgccgaaat cgctccaga                                                   19

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gtctttcctt ctattgttgg tc                                               22

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ccatcaggaa gttcataaga c                                                21

<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
caaagccaat tcagcctcaa atg                                              23

<210> SEQ ID NO 24
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
cttggatcag ggtggactcg tag                                              23

<210> SEQ ID NO 25

```
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
ccaacagtga aaagtcatcc ttt                                            23

<210> SEQ ID NO 26
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gcaataggaa ttgattttcc ttg                                            23

<210> SEQ ID NO 27
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
tatcgttctt gactctggtg atg                                            23

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gaaagagtga ccacgttcag c                                              21

<210> SEQ ID NO 29
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
ctcgaggctt taggtcaaat tgtgg                                          25

<210> SEQ ID NO 30
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
cccgggttat tgcttgatac catattgtg                                      29

<210> SEQ ID NO 31
<211> LENGTH: 50
<212> TYPE: DNA
```

-continued

<213> ORGANISM: Artificial Sequence
<220> FEATURE:
<223> OTHER INFORMATION: Description of Artificial Sequence: Synthetic
      primer

<400> SEQUENCE: 31
gcggccgcgc tagcgcatgc atgtctcaag atctcttcaa cgtaccgatc          50

<210> SEQ ID NO 32
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gacgtcccgc ggggcgcgcc ggtgataaaa ggcaagacaa agaacgcgta          50

<210> SEQ ID NO 33
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
catggttgag attgtaagat ag                                       22

<210> SEQ ID NO 34
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
agtcaatgga cgtggagtc                                           19

<210> SEQ ID NO 35
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
catcaccatg ggatcaaaag aatgtttaat actgaatctc ca                 42

<210> SEQ ID NO 36
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
ctaattaagc ttggcttaag ctttaatagc atcagattca attttttc           48

<210> SEQ ID NO 37
<211> LENGTH: 368
<212> TYPE: PRT
<213> ORGANISM: Rhizopus oryzae -continued

<400> SEQUENCE: 37

Met Ser Gln Asp Leu Phe Asn Val Pro Ile Phe Phe Ile Leu Phe Arg
1               5                   10                  15

Glu Thr Thr Glu Ala Ala Ile Ile Ile Ser Val Leu Leu Ser Phe Leu
            20                  25                  30

Lys Arg Met Phe Asn Thr Glu Ser Pro Val Tyr Lys Arg Leu Arg Asn
        35                  40                  45

Gln Val Trp Ile Gly Gly Ala Ala Gly Leu Phe Ile Cys Leu Cys Ile
    50                  55                  60

Gly Ala Ala Phe Ile Ala Val Tyr Tyr Thr Val Leu Asn Asp Leu Trp
65                  70                  75                  80

Gly Asn Ser Glu Asp Ile Trp Glu Gly Val Phe Ser Leu Val Ala Val
            85                  90                  95

Ile Met Ile Thr Ala Met Gly Leu Ala Met Leu Lys Thr Glu Arg Met
            100                 105                 110

Gln Glu Lys Trp Lys Val Lys Leu Ala Lys Ala Met Gln Lys Ser Asn
        115                 120                 125

Ser Glu Lys Ser Ser Phe Lys Glu Lys Leu Gln Lys Tyr Ala Phe Phe
130                 135                 140

Val Leu Pro Phe Ile Thr Val Leu Arg Glu Gly Leu Glu Ala Val Val
145                 150                 155                 160

Phe Ile Gly Gly Val Ser Leu Gly Ile Gln Gly Lys Ser Ile Pro Ile
                165                 170                 175

Ala Ala Ile Met Gly Ile Ile Cys Gly Cys Leu Val Gly Phe Leu Ile
            180                 185                 190

Tyr Arg Gly Gly Ser Leu Ile Gln Leu Arg Trp Phe Phe Val Phe Ser
        195                 200                 205

Thr Val Val Leu Tyr Leu Val Ala Ala Gly Leu Met Ala Lys Gly Val
210                 215                 220

Gly Tyr Leu Glu Gln Asn Ala Trp Asn Gln Val Ile Gly Gly Glu Ala
225                 230                 235                 240

Ala Asp Val Ile Ser Tyr Arg Val Ser Thr Ala Val Trp His Val Ser
                245                 250                 255

Trp Gly Asp Pro Glu Ala Asn Asn Asp Thr Ser Gly Gly Trp Gln Ile
            260                 265                 270

Phe Asn Ala Ile Leu Gly Trp Asn Asn Thr Ala Thr Tyr Gly Ser Ile
        275                 280                 285

Ile Ser Tyr Cys Leu Tyr Trp Leu Phe Val Cys Cys Tyr Leu Val Phe
290                 295                 300

Ser Tyr Phe Lys Glu Lys Arg Ala Ala Ile Arg Lys Ala Glu Ala Gly
305                 310                 315                 320

Glu Trp Asp Asp Gly Asp Glu Ala Leu Glu Asn Ala Lys Gln Tyr Ile
                325                 330                 335

Gly Asn Asp Gly Glu Phe Ile Val Glu Asp Lys Glu Ser Asp Glu Glu
            340                 345                 350

Ala Asn Asn His Pro Lys Glu Lys Ile Glu Ser Asp Ala Ile Lys Ala
        355                 360                 365

<210> SEQ ID NO 38
<211> LENGTH: 381
<212> TYPE: PRT
<213> ORGANISM: Candida albicans

<400> SEQUENCE: 38

Met Val Asp Val Phe Asn Val Gln Ile Phe Phe Ile Val Phe Arg Glu

```
            1               5                  10                 15
        Ser Leu Glu Ala Ile Ile Val Val Ser Val Leu Leu Ala Phe Val Lys
                        20                  25                  30

Gln Ser Met Gly Gly Ser Ser Asp Pro Gln Leu Lys Lys Arg Leu Tyr
                        35                  40                  45

Arg Gln Ile Trp Leu Gly Ala Gly Leu Gly Val Leu Val Cys Leu Tyr
                        50                  55                  60

Gly Val Leu Ser Ile Gly Ala Ser Tyr Gly Leu Gly Lys Asp Ile Phe
        65                      70                  75                  80

Gly Val Ile Ser Glu Asp Leu Trp Glu Gly Ile Phe Cys Ile Ile Ala
                        85                  90                  95

Thr Val Leu Ile Thr Ala Met Gly Ile Pro Met Leu Arg Ile Asn Lys
                        100                 105                 110

Met Lys Glu Lys Trp Arg Val Lys Leu Ala Gln Ala Leu Ile Lys Ser
                        115                 120                 125

Pro Thr Asn Lys Lys Asp Arg Phe Lys Leu Gly Tyr Leu Gly Lys Lys
                        130                 135                 140

Tyr Ala Leu Phe Ile Leu Pro Phe Leu Gln Val Leu Arg Glu Gly Leu
        145                     150                 155                 160

Glu Ala Val Val Phe Val Gly Gly Val Gly Leu Asn Ser Pro Ala Thr
                        165                 170                 175

Ser Phe Pro Ile Pro Val Ile Val Gly Leu Ile Ala Gly Ile Val Val
                        180                 185                 190

Gly Ala Leu Leu Tyr Tyr Phe Gly Ser Ser Met Ser Met Gln Ile Phe
                        195                 200                 205

Leu Ile Ile Ser Thr Cys Ile Leu Tyr Leu Ile Ala Ala Gly Leu Phe
                        210                 215                 220

Ser Arg Gly Ile Trp Tyr Phe Glu Thr Asn Thr Tyr Asn Lys Lys Thr
        225                     230                 235                 240

Gly Gly Asp Ala Ser Glu Asn Gly Ser Gly Pro Gly Thr Tyr Asp Ile
                        245                 250                 255

Ser Lys Ser Val Trp His Val Asn Cys Arg Asn Pro Glu Thr Asp Asn
                        260                 265                 270

Gly Trp Asp Ile Phe Asn Ala Ile Leu Gly Trp Gln Asn Ser Ala Thr
                        275                 280                 285

Tyr Gly Ser Val Ile Ser Tyr Asn Ile Tyr Trp Leu Phe Ile Ile Cys
                        290                 295                 300

Val Leu Leu Leu Met Val Tyr Glu Glu Lys His Gly His Leu Pro Phe
        305                     310                 315                 320

Thr Lys Asn Leu Thr Leu Val Gln Leu Asn Pro Met Tyr His Ile Lys
                        325                 330                 335

Gly Lys Lys Lys Leu Glu Leu Asn Lys Ala Glu Lys Asp Glu Leu Phe
                        340                 345                 350

Thr Lys Leu Gln Gln Gln Asn Phe Gly Gln Ala Ala Glu Val Asp Glu
                        355                 360                 365

Thr Ser Ser Asn Lys Gln Met Asp Ser Gln Glu Asn Ser
                        370                 375                 380

<210> SEQ ID NO 39
<211> LENGTH: 404
<212> TYPE: PRT
<213> ORGANISM: Saccharomyces cerevisiae

<400> SEQUENCE: 39

Met Pro Asn Lys Val Phe Asn Val Ala Val Phe Phe Val Val Phe Arg
```

```
  1               5                  10                 15
Glu Cys Leu Glu Ala Val Ile Val Ile Ser Val Leu Leu Ser Phe Leu
                20                  25                 30
Lys Gln Ala Ile Gly Glu His Asp Arg Ala Leu Tyr Arg Lys Leu Arg
                35                  40                 45
Ile Gln Val Trp Val Gly Val Leu Leu Gly Phe Ile Ile Cys Leu Ala
                50                  55                 60
Ile Gly Ala Gly Phe Ile Gly Ala Tyr Tyr Ser Leu Gln Lys Asp Ile
 65                  70                 75                 80
Phe Gly Ser Ala Glu Asp Leu Trp Gly Ile Phe Cys Met Ile Ala
                85                  90                 95
Thr Ile Met Ile Ser Met Met Gly Ile Pro Met Leu Arg Met Asn Lys
                100                 105                110
Met Gln Ser Lys Trp Arg Val Lys Ile Ala Arg Ser Leu Val Glu Ile
                115                 120                125
Pro His Arg Lys Arg Asp Tyr Phe Lys Ile Gly Phe Leu Ser Arg Arg
                130                 135                140
Tyr Ala Met Phe Leu Leu Pro Phe Ile Thr Val Leu Arg Glu Gly Leu
145                 150                 155                160
Glu Ala Val Val Phe Val Ala Gly Ala Gly Ile Thr Thr Gln Gly Ser
                165                 170                175
His Ala Ser Ala Tyr Pro Leu Pro Val Val Gly Leu Ile Cys Gly
                180                 185                190
Gly Leu Val Gly Tyr Leu Leu Tyr Gly Ala Ser Lys Ser Ser Leu
                195                 200                205
Gln Ile Phe Leu Ile Leu Ser Thr Ser Ile Leu Tyr Leu Ile Ser Ala
                210                 215                220
Gly Leu Phe Ser Arg Gly Ala Trp Tyr Phe Glu Asn Tyr Arg Phe Asn
225                 230                 235                240
Leu Ala Ser Gly Gly Asp Ala Ser Glu Gly Gly Asp Gly Asn Gly Ser
                245                 250                255
Tyr Asn Ile Arg Lys Ala Val Tyr His Val Asn Cys Cys Asn Pro Glu
                260                 265                270
Leu Asp Asn Gly Trp Asp Ile Phe Asn Ala Leu Leu Gly Trp Gln Asn
                275                 280                285
Thr Gly Tyr Leu Ser Ser Met Leu Cys Tyr Asn Ile Tyr Trp Leu Val
                290                 295                300
Leu Ile Ile Val Leu Ser Leu Met Ile Phe Glu Glu Arg Arg Gly His
305                 310                 315                320
Leu Pro Phe Thr Lys Asn Leu Gln Leu Lys His Leu Asn Pro Gly Tyr
                325                 330                335
Trp Ile Lys Asn Lys Lys Gln Glu Leu Thr Glu Glu Gln Lys Arg
                340                 345                350
Gln Leu Phe Ala Lys Met Glu Asn Ile Asn Phe Asn Glu Asp Gly Glu
                355                 360                365
Ile Asn Val Gln Glu Asn Tyr Glu Leu Pro Glu Gln Thr Thr Ser His
                370                 375                380
Ser Ser Ser Gln Asn Val Ala Thr Asp Lys Glu Val Leu His Val Lys
385                 390                 395                400
Ala Asp Ser Leu
```

<210> SEQ ID NO 40
<211> LENGTH: 969
<212> TYPE: DNA

<213> ORGANISM: Aspergillus fumigatus

<400> SEQUENCE: 40

| | | | | | |
|---|---|---|---|---|---|
| atgatcggag | cgttctatgg | atatggtaag | gatcacttcg | ctagcacgga | ggacctgtgg | 60 |
| gagggcatct | tctccctgat | cgccagtgtc | atcatcacca | ttatgggtgc | tgccctgctt | 120 |
| cgtgtcacca | agttgcagga | gaagtggcgc | gtcaagctag | ctcaagccct | ggaagcaaag | 180 |
| ccgttgactg | gcggcacatt | caaaaacaac | ctcaaacttt | gggcggagaa | atacgccatg | 240 |
| tttctcctcc | ccttcatcac | cgttctccga | gaaggcctgg | aagcagtggt | gttcattgga | 300 |
| ggcgtcagtc | tcagttttcc | tgcaactgcc | ttccctctac | ctgtttttac | tggcattctc | 360 |
| gcaggagtgg | ccattgggta | cctactgtat | cggtatgttg | aaacccctga | tcagctgtc | 420 |
| tttctcaaat | agaccaccat | gctgatggtc | tgcagaggag | gaaaccaagc | ctccctccag | 480 |
| atcttcctga | tcatctccac | ttgcatcctc | tacctggttg | ctgccggcct | cttctcccga | 540 |
| ggcgtctggt | atctggagaa | caatacttgg | aaccacgtaa | ttggtggtga | tgctgccgag | 600 |
| acaggtgccg | gtccgggatc | gtatgacatc | cgacagagcg | tctggcatgt | caactgctgt | 660 |
| agtcctctcg | ttaatggtgg | cgggggatgg | ggtatcttca | acgccatcct | tggctggaca | 720 |
| aactcggcaa | cctatggctc | cgttctttca | tacaaccttt | actggattgc | ggtgatcgtc | 780 |
| tggtttgtgg | ctatgcgtca | caaggaacgc | catggacgat | tgcctgtggt | cgaccctctg | 840 |
| ctgaatcggc | tgcgaggccg | aaagtctgcc | gaacctggga | atggagagca | agatgtcgag | 900 |
| gtcagcacga | taccatctga | tttgcagacg | gagtccaaaa | taccgaaaag | cggagcatcc | 960 |
| cttgtctga | | | | | | 969 |

<210> SEQ ID NO 41
<211> LENGTH: 1089
<212> TYPE: DNA
<213> ORGANISM: Candida guilliermondii

<400> SEQUENCE: 41

| | | | | | |
|---|---|---|---|---|---|
| atgaactttg | aagactactt | ctcggttcaa | atcttcttta | taatcctccg | agaaacgttg | 60 |
| gagaccgcta | tagtgatttc | ggttcttctt | tcgttcatca | atcaaagaag | ccaagaagca | 120 |
| aatgaccgag | gaaattctgc | taatgaagct | gctcatactc | gaggattgcg | ggtccaggta | 180 |
| tgggccgggg | ccttaatggg | atttgttgtg | tgttttgcca | tcggagtggc | atttgtggtt | 240 |
| gcattttatg | tcattggaga | gaactactgg | ctgtatgctg | aaagactctg | ggagggtatt | 300 |
| ttctcgcttc | tttcgagtat | aataatcaca | gtgatgggta | tcggattgct | acgtataaac | 360 |
| cgcgtgatga | agttaagtg | gtttgctaag | ttgggtgatg | cctttgatct | gcattcgcac | 420 |
| ggtagaggcc | ataaaaagaa | gtactttctt | gcattattac | catttataac | cacactcaga | 480 |
| gaaggcttgg | aggccgtggt | attcgtgggt | ggaattggtc | tttcgctgcc | agtttcttcc | 540 |
| atcccatttt | ccattctcag | tggaatctgt | gtgggatcca | caatcggtta | cacttttgtac | 600 |
| aaaggaggca | acaagctttc | tctccaatac | ttcctcatct | tgctgacctg | cttttttgtac | 660 |
| atagttctgg | cagggcttat | gagtagagga | gtatggtttt | tggaactcga | gctgtatgtg | 720 |
| agaaaatgtg | gaggactcga | cgttagcgaa | acaggtagtg | gacctggatc | ttatgatcct | 780 |
| gctacaagcg | tgtggcatgt | caattgctgt | aacggactca | cagatggctg | gtggatggtt | 840 |
| ttaaatgctc | ttgttggctg | gaccaattcc | gcaacttatg | gcagcgtagg | tgcttattgt | 900 |
| gcctattgga | tattggtcat | ttcatggctt | gagatccgct | tgtacgaaga | gcatcatgga | 960 |
| ctcttaccct | ttgttcctgt | gcgttggcag | ttgaagcgta | tcagaaaaaa | aatcaaatta | 1020 |

```
tacgaagccc gggccaaaca tggcgctgca atagaggctg aaacagaggc agaattactc    1080
atggaataa                                                             1089

<210> SEQ ID NO 42
<211> LENGTH: 996
<212> TYPE: DNA
<213> ORGANISM: Aspergillus flavus

<400> SEQUENCE: 42
agccctcttt cattcctttc tgaagcctct accttccact caacatggca accgatgtat      60
ttgcagttcc cagtatgcat tcttttcttg ttatgcccca tctattaatc aggaactaac     120
ttagtttgac taacttatcg aagtattctt catctgcttt cgagaatgcg ttgagaccag     180
catcattgtt tcggtattac ttgccttcat caagcagacg ctggggtcgg acacggatgc     240
ctttactcgc aaaaggctta tcaaacaggt tactaccatc ttctcattcc gtccccaccc     300
tatagagaca acattgacga tcaataggtc tggtggggag ttgcggtcgg ctgtttata      360 tgcctctgta ttggaggtgg tatgattggg ccttctacg ggtatggcaa ggaccatttt     420
gccagcacgg aggatttatg ggaaggcatc tttgctttag tcgccgccgt catcatcaca     480
gtcatgggag cagcccttct gcgggtgaat aaactgcagg agaaatggcg tgtcaagctg     540
gcccaggcat tggcggcaaa acctcaacct caagggagaa tgacagacaa gatcaagcaa     600
tggtcacaga agtatttcat gttcatctta cccttcatta cggtacttcg ggagggtcta     660
gaggctgtgg tgtttatcgg gggtgttagt ctcagcttcc ccgcaagcgc gttccctctc     720
cctgtattca cgggactctt ggctggtgtg gtagttggtt atatcattta ccggtgagtg     780
tgatatgggc ggcattgaaa ctgaatccca atgctgatag tagtctttgc gatttatcat     840
aggggcggga atcaaacctc acttcagata ttcatggtca tctcgacatg tctgctctac     900
ttggtcgctg ctggacttt tgtcccgagg c gtctggttct tggagaacaa cacttggagc     960
aacctcatcg gtggcgatgc ctcagaaacg ggagct                                996

<210> SEQ ID NO 43
<211> LENGTH: 1341
<212> TYPE: DNA
<213> ORGANISM: Aspergillus flavus

<400> SEQUENCE: 43
atggcaaatc aagtctttgc agtcactggt aactctcatt atactctctg agtctgcttt      60
tgtacaagac gaccgttgct gaccgtgtat agtcttttc atttgcttcc gagaatgtct     120
cgaaagcagt atcattgtat cggtgcttct tgccttcctc acccaaactt ggggtgctga     180
aggagacaag gcagctctga agagattgcg aatacaggtg agtgtccttc cctatttctt     240 tataccttg tttatcatga acatcattcg ataatgagct gctaacaata acaggtatgg     300
tgtggagtag gtttaggtct attcttgtgc ctatgtatcg gtgcaggtat gatcggagct     360
ttctacgggt tggaaaaaga taccttcacg aacacagagg atatctggga aggcattttt     420
ggctttatag catccatcat tatttctatc atggggcgg ccttttgcg tgtgaacaaa     480 atgcgcgaga atggcgcgt caagctctcc cgtgccttgg agaaaaagga aaagtctacg     540
accataatgg gtcgtctgaa ggactggtcc gagaaatatg tcatgttcat cttgccattc     600
gttaccgttc ttcgagaggg acttgaggct atcgtttatg tcggtggtgt gggactggga     660
ttgccagcgt cttcattccc cttggccgtg ttctgtggcc ttttggctgg tgttgcagta     720
ggctatgtga tgtatcggta agtcttgtgc gttacattct gtctactta agaatcatta     780
```

```
tctgcacagt atcgttcgac ggtggctaac gaatcttgat gcaggggtgg aagctcaact      840
tccttacagt actttctgat tatatctact tgcttcctct acttggtcgc cgcaggcttg      900
ttttcccgcg ctgtctggta cctggagaat aatacctgga accatgtcat tggtggagat      960
gcttctgaga ccggctcagg ccctggatct tacgatattc gccagagtgt ctggcatgta     1020
aactgctgta acccagagct tggcggtggt ggtggttggg gtatcttcaa cgctctgttt     1080
gggtggacca attccgccac ctatggatca gtgctatctt acaaccttta ctgggtagtg     1140
atcattacct catacgtctg catgaggtac aatgagaagc acggctacat tcccgtctta     1200
acaccgatcg caaggaagct gaagcttggt cgattcaaga agggctctga ggaagaacat     1260
gtccccgagg ttgtcgaaga gaggaaggag gttaaccatc tggcccggca aattgttacc     1320
agaacaatga gtgaagcata g                                               1341

<210> SEQ ID NO 44
<211> LENGTH: 1437
<212> TYPE: DNA
<213> ORGANISM: Candida tropicalis

<400> SEQUENCE: 44
atggcacaga tcgaggagta ctttttctgtt cagatattct ttatcattct cagagagact     60
cttgaaacag ctatcatcat ctcggtgttg ctatccttca tcaaccaacg ttcgcacaag    120
catggctccc agtctcagaa catagcagta tcatcgtcat caccatcgac atcatcacct    180
ggttcagtgg accccgccga tgagccacta ccttcgagtt caaccactgt caccccggga    240
cagacatccc atttggagaa agtgcatcgt aagcttaaac ttcaagtatg ggtgggcgcc    300
cttcttgggc ttttcatttg ttttgtcatc gggatggtat ttacgttgat gttttatttt    360
gtgggacagg actactgggc atacacggaa cgagtatggg aaggtgtgtt ctgcatattg    420
tcaagtgtga tcatcactgt gatggggatt gggcttttga gaatcaacaa agttatgaag    480
atcaaatggt ggatcaagtt gggagatgcg tacaataatg aagaatacgc agaagacgaa    540
gaggcagaag gcgaggaaga gattgccaag ttaggagacg acgatgtgat gtatgaggat    600
agtatggcta attatggagg caccaggtcg agctcagagt caaacaccgt ggaggagaac    660
atcccattaa ccggtacgcc tgctactcct gcaacagcta gaaccacaac cacaaagaag    720
aacacaccaa ggaaacaggg gttcaccaag aaatactacc ttgctatttt accattggtc    780
accacattga gagaagggtt agaagcggtt gtgttcattg gtggctcagc catgacgtcc    840
acggtatttt cgatcattgt gtctgttgtc tgcggaattg catttggttc cttgattggg    900
tacttgcttt accaaggggg gaacaaactc tcccttcagt attttcttat tgctcaaca     960 tgttttcttt acatggtcag cgctggggtt atcagtcgtg gtgtctggtt tatggagctt    1020
gaaagatatg tccgtgcatg tgggggcatg gacgttagtg aaacgggaag tgggccaggt    1080
tcatatgata tcgcaaccag tgtgtggcat gtcaactgtt gtaacggact aactgacggt    1140
tggtggatgg tgttgaacgc aattgtcggc tggaccaatt cggctacata tggcagtgtg    1200
attagttata tggcatactg gttgttggta attgtgtggt gaaagttaa gttgtatgaa     1260 gagagggaag tgtgttgcc ttggattccc gtaagatggc aactcaagag aattagaaag    1320
aagattagat tgtatgaatt gaggacccgt cagcaagagc aacaggagca acagagaggt    1380
ggtagtggta gtggtaatga attgccagaa tcgcaaggat tgttgcaaca ggattga       1437

<210> SEQ ID NO 45
<211> LENGTH: 4
<212> TYPE: PRT
```

```
<213> ORGANISM: Saccharomyces cerevisiae
<220> FEATURE:
<223> OTHER INFORMATION: cell surface motif of FTR required for full
      function of FTR in Saccharomyces cerevisiae
<220> FEATURE:
<221> NAME/KEY: VARIANT
<222> LOCATION: (2)...(3)
<223> OTHER INFORMATION: Xaa = any amino acid

<400> SEQUENCE: 45

Glu Xaa Xaa Glu
1
```